United States Patent [19]

Ring

[11] Patent Number: 5,705,614
[45] Date of Patent: Jan. 6, 1998

[54] METHODS OF PRODUCING ANTIGEN FORKS

[75] Inventor: David B. Ring, Palo Alto, Calif.

[73] Assignee: Chiron Corporation, Emeryville, Calif.

[21] Appl. No.: 396,595

[22] Filed: Mar. 1, 1995

Related U.S. Application Data

[63] Continuation-in-part of Ser. No. 311,210, Sep. 21, 1994, abandoned, which is a continuation of Ser. No. 163,988, Dec. 7, 1993, abandoned, which is a continuation-in-part of Ser. No. 45,969, Apr. 9, 1993, abandoned.

[51] Int. Cl.$^6$ ............................ C07K 16/46; C12N 5/12
[52] U.S. Cl. .................. 530/387.3; 530/388.2; 530/388.22; 530/388.8; 530/388.85; 435/240.26; 435/240.27
[58] Field of Search .................. 530/387.3, 388.2, 530/388.22, 388.8, 388.85; 435/240.26, 240.27

[56] References Cited

U.S. PATENT DOCUMENTS 4,474,893  10/1984  Reading.
4,676,980  6/1987  Segal et al..
5,283,323  2/1994  Barzousky et al. .................. 530/387.1

FOREIGN PATENT DOCUMENTS 0 468 637-B1  1/1992  European Pat. Off..

OTHER PUBLICATIONS

Debrin et al., *Oncogene* (1988) 2:387–394.
Hudziak et al., *Mol. & Cellular Biol.*, (1989) 9(3):1165–1172.
Shepard et al., *J. of Clin. Immun.* (1991) 11(3):117–127.
Yu, et al., *Cancer Research* (1990) 50:3231–3238.
Ring et al., Canc. Immunol. Immunother., 1994, 39:41.

*Primary Examiner*—Frank C. Eisenschenk
*Attorney, Agent, or Firm*—Paul B. Savereide; Robert P. Blackburn

[57] ABSTRACT

The present invention relates to a class of molecules called "antigen forks" that inhibit cell growth. These antigen forks possess separate binding elements for two different cell surface antigens and are believed to heterologously crosslink the antigens by binding to them. The two antigens recognized by an antigen fork differ in at least one cellular functional quality, but are simultaneously expressed on the surface of at least one cell type targeted for killing or growth inhibition. The present invention also relates to a method of assay to determine which antibodies may be useful in the preparation of antigen forks.

1 Claim, 46 Drawing Sheets

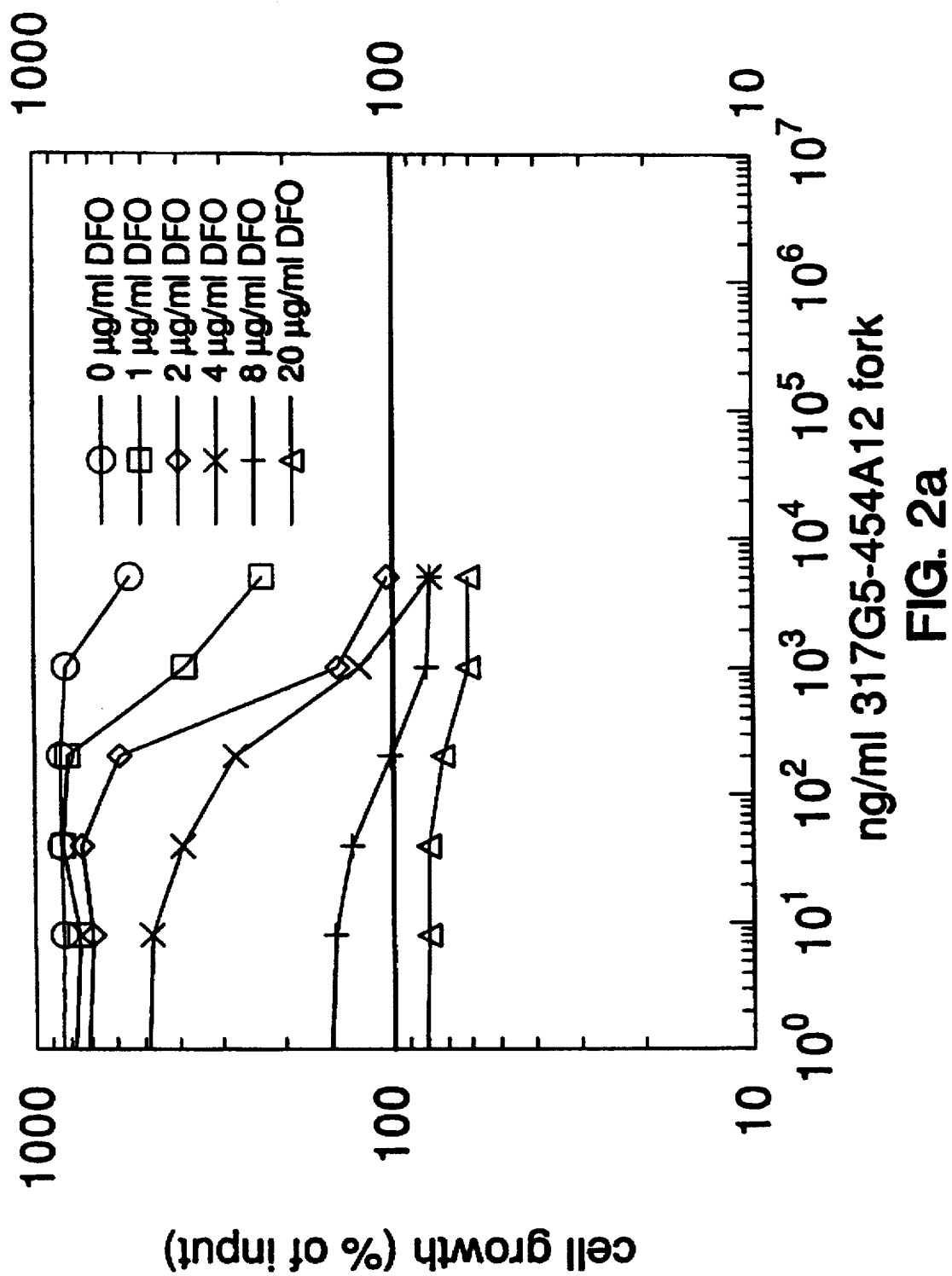

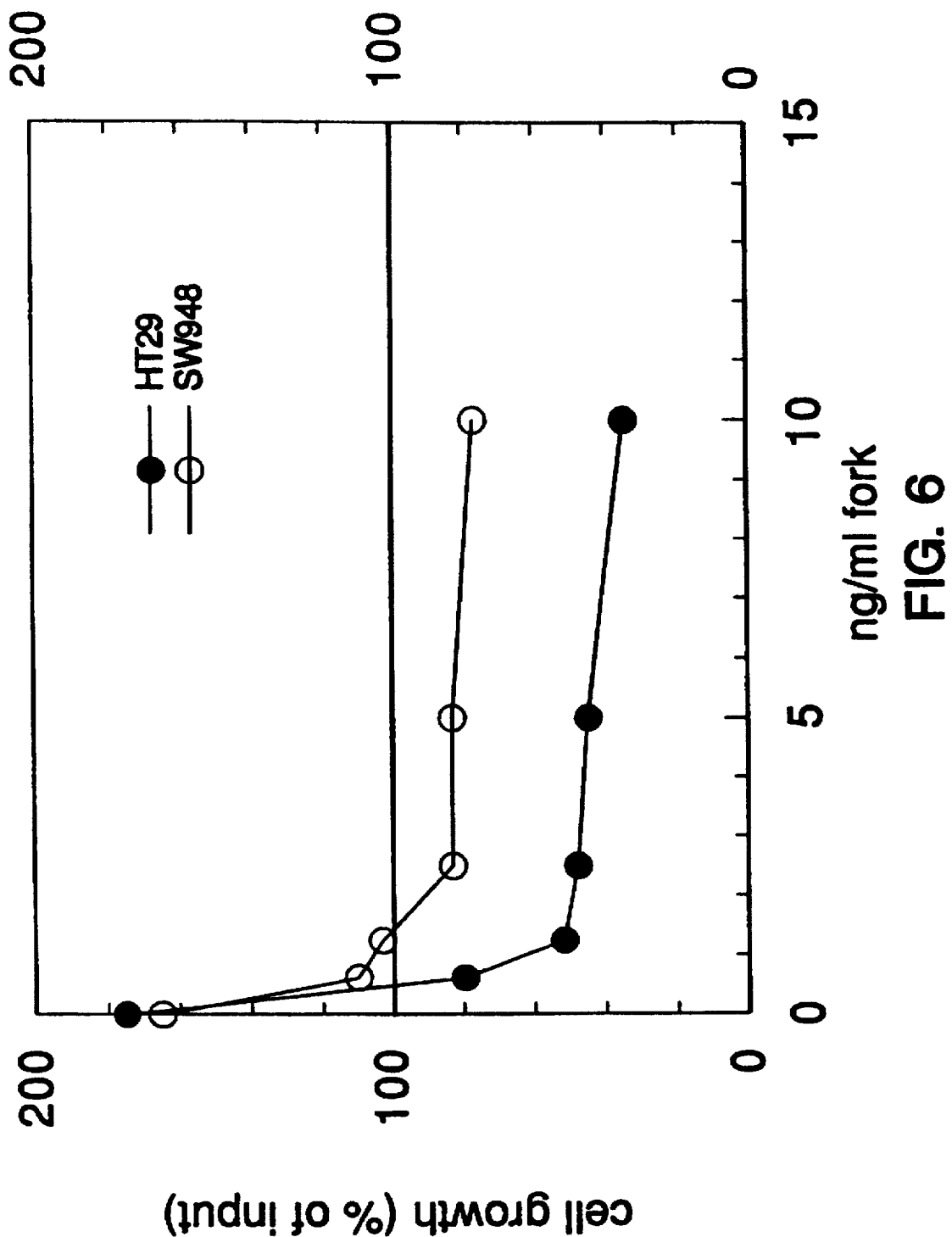

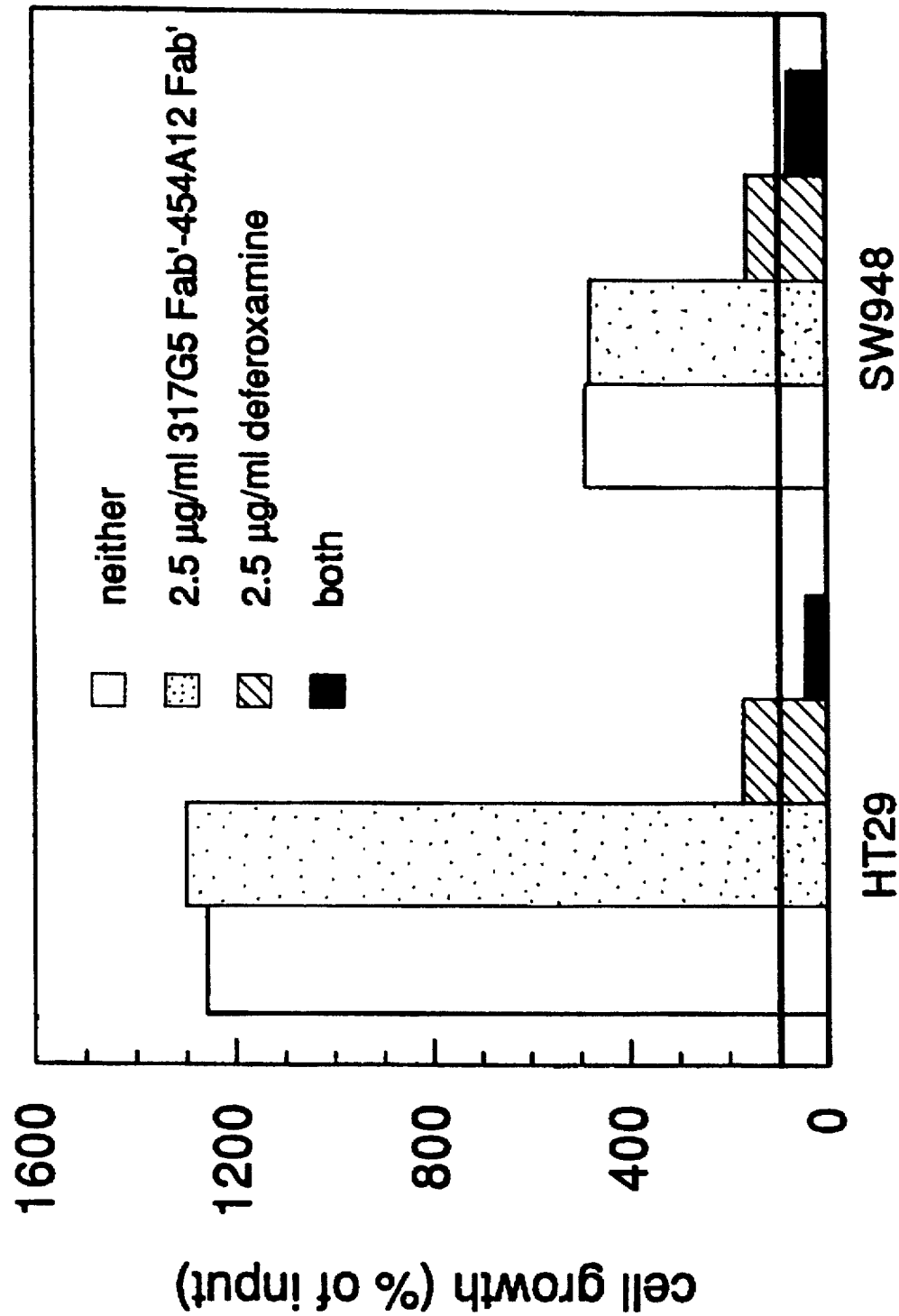

| | 2G3 | 15D3 | 32A1 | 33F8 | 34F2 | 34F3 | 44F4 | 113F1 | 219F3 | 260F9 | 280D11 | 310B7 | 310F3 | 387H9 | 388D4 | 398D6 | 421E8 | 454A12 | 520C9 | 735B11 | 788G6 |
|---|---|---|---|---|---|---|---|---|---|---|---|---|---|---|---|---|---|---|---|---|---|
| 788G6 | | | | | | | | | | | | | | | | | | | | | |
| 735B11 | | | | | | | | | | | | | | | | | | | | | |
| 520C9 | | | | | | | | | | | | | | | | | | | | | |
| 454A12 | | | | | | | | | | | | | | | | | | | | | |
| 421E8 | | | | | | | | | | | | | | | | | | | | | |
| 398D6 | | | | | | | | | | | | | | | | | | | | | |
| 388D4 | | | | | | | | | | | | | | | | | | | | | |
| 387H9 | | | | | | | | | | | | | | | | | | | | | |
| 310F3 | | | | | | | | | | | | | | | | | | | | | |
| 310B7 | | | | | | | | | | | | | | | | | | | | | |
| 280D11 | | | | | | | | | | | | | | | | | | | | | |
| 260F9 | | | | | | | | | | | | | | | | | | | | | |
| 219F3 | | | | | | | | | | | | | | | | | | | | | |
| 113F1 | | | | | | | | | | | | | | | | | | | | | |
| 44F4 | | | | | | | | | | | | | | | | | | | | | |
| 34F3 | | | | | | | | | | | | | | | | | | | | | |
| 34F2 | | | | | | | | | | | | | | | | | | | | | |
| 33F8 | | | | | | | | | | | | | | | | | | | | | |
| 32A1 | | | | | | | | | | | | | | | | | | | | | |
| 15D3 | | | | | | | | | | | | | | | | | | | | | |
| 2G3 | | | | | | | | | | | | | | | | | | | | | |

FIG. 3I

SKBR3 cells

FIG. 32

METHODS OF PRODUCING ANTIGEN FORKS

CROSS-REFERENCE TO RELATED APPLICATIONS

The present application is a continuation-in-part of U.S. Ser. No. 08/311,210, filed Sep. 21, 1994, now abandoned, which is a continuation of U.S. Ser. No. 08/163,988, now abandoned, filed Dec. 7, 1993, which is a continuation-in-part of U.S. Ser. No. 08/045,969 filed Apr. 9, 1993, now abandoned.

FIELD OF THE INVENTION

This invention relates to novel methods of restricting cell growth and treating disease using molecules that inhibit cellular function. In particular, this invention relates to methods of inhibiting cellular function with an "antigen fork", a molecule possessing two separate binding elements where one binding element recognizes a different cell surface antigen than a second binding element, and where the two different antigens have distinct functional properties. This invention, thus, also relates to the antigen fork, and to a hybrid hybridoma that produces one embodiment of the antigen fork.

BACKGROUND OF THE INVENTION

Antibodies that bind to cell surface antigens are well-known in the art. The actual binding of such antibodies to their cell surface antigens can have varying effects. The binding may have no apparent effect, may initiate or block signal transduction (leading to a change in cell state), or may alter antigen turnover rate by enhancing or inhibiting endocytosis or by changing the route of intracellular processing. The effect of antibody binding may depend on the valency of the antibody. Monovalent antibodies often have little or no effect, suggesting that antigen crosslinking may be important in mediating the effect of binding.

Monospecific antibodies recognize only a single antigenic determinant. Although some monospecific antibodies that bind to cell surface antigens inhibit growth upon binding, the availability of highly tumor-selective monospecific antibodies with effective anti-growth properties is limited. Therefore, it would be desirable to develop agents that are more likely to inhibit tumor cell growth than monospecific antibodies, and that are also more selective than monospecific antibodies in affecting only the growth of tumor cells and not of normal cells.

Bispecific antibodies (or heteroantibodies) are multivalent antibodies containing binding sites specific for two different antigenic determinants. Bispecific antibodies may be chemically synthesized as antibody heteroconjugates (AHCs) by covalently attaching two whole monoclonal antibodies ("whole AHCs") (B. Karpovsky, et al. (1984) *J. Exp. Med.* 160(6):1686–1701) or by attaching two monoclonal antibody Fab or Fab' fragments ("monovalent AHCs") (M. Brennan, et al., *Science* (1985) 229:(1708):81–83), where each antibody or antibody fragment has a different antigenic specificity.

Alternatively, bispecific antibodies may be produced from a "hybrid hybridoma," a cell fusion of two monoclonal antibody-producing cells, as shown, for example, in U.S. Pat. No. 4,474,893 to Reading; C. L. Reading, in HYBRIDOMAS AND CELLULAR IMMORTALITY, B. H. Tom et al., eds., 1984, (New York: Plenum Press), p. 235; U. D. Staerz et al., *Proc. Natl. Acad. Sci.* (1986) 83: 1453–1457; A. Lanzavecchia et al., *Eur. J. Immunol.* (1987)17:105–111; D. B. Ring et al., in BREAST EPITHELIAL ANTIGENS: MOLECULAR BIOLOGY TO CLINICAL APPLICATIONS, R. Cedani, ed., 1991, (New York: Plenum Press), pp. 91–104. Bispecific antibodies where one recognized antigenic determinant is a cell surface receptor on a cytotoxic cell and the other determinant is located on a different cell, targeted to be killed by the cytotoxic cell can be made by the method shown in U.S. Pat. No. 4,676,980.

Prior to the present application, no one has constructed a molecule (1) containing two binding sites that recognize two antigenic determinants located on the surface of a single cell; (2) where the two recognized antigenic determinants differ in at least one cellular functional quality; and (3) where the binding of the molecule to the cell surface inhibits cell growth. The present invention relates to "antigen forks" which possess the above-described properties.

SUMMARY OF THE INVENTION

It is an object of the present invention to provide a method for the inhibition of growth of a targeted cell such as a cancer cell or a virus-infected cell. It is also an object of the present invention to provide an agent for the inhibition of such cell growth. It is a further object of the present invention to provide a method for treatment of cancer and other diseases characterized by expression of a disease-related antigen on the surface of an infected cell, such as a virus-infected cell, by application of the agent and method of inhibition of cell growth.

In accordance with one of the objects of the present invention, there is provided an agent, i.e., an antigen fork, that contains a first binding element which specifically binds to a first antigen and a second binding element which specifically binds to a second antigen, where the first antigen differs from the second antigen in at least one cellular functional quality, the first and second antigens being capable of being simultaneously expressed on the surface of a cell, and where the binding of the antigen fork to the first and second antigens inhibit growth of the cell.

In accordance with another object of the present invention, there is provided a hybrid hybridoma that is capable of producing the antigen fork described above.

In accordance with a further object of the present invention, there is provided a method of inhibition of cell growth by contacting a cell targeted for inhibition of growth with the antigen fork described above.

In accordance with yet another object of the present invention, there is provided the method of inhibition of cell growth as described above, in conjunction with contacting the targeted cell with an anti-viral agent, or a cytotoxic, or cytostatic agent conventional in the art, such as deferoxamine or cisplatin, either sequentially or simultaneously with the antigen fork.

In accordance with still another object of the present invention, there is provided a method of treatment of cancer or other diseases as mentioned above in which the inhibition of cell growth is desired, by administering the antigen fork described above, either alone or in conjunction with an antiviral agent or, a cytostatic or cytotoxic agent, either sequentially or simultaneously.

The present invention, thus, relates to the recognition that one can inhibit cell growth and/or cause cell death by heterodimerizing and crosslinking cell surface antigens using the antigen fork described above.

BRIEF DESCRIPTION OF THE DRAWINGS

FIGS. 2a and 2b show the growth inhibitory effects of various concentrations of the 317G5-454A12 antigen fork and deferoxamine on the human colorectal cancer cell line SW948.

FIG. 6 shows the effects of monovalent antigen fork heterodimer (MAFHD) 317G5 Fab'-454A12 Fab' plus deferoxamine on two colorectal cancer cell lines, HT29 and SW948.

FIGS. 7a and 7b show the results of two experiments depicting the cytotoxic effects of deferoxamine and/or monovalent antigen fork heterodimer 317G5 Fab'-454A12 Fab' on HT29 and SW948 cells.

FIG. 31 shows the effects of the cross-linked MAb pairs on viability of SKBR3 cells.

FIG. 32 shows the effects of the cross-linked MAb pairs on viability of SW948 cells.

DETAILED DESCRIPTION OF THE INVENTION

Figure 1A:
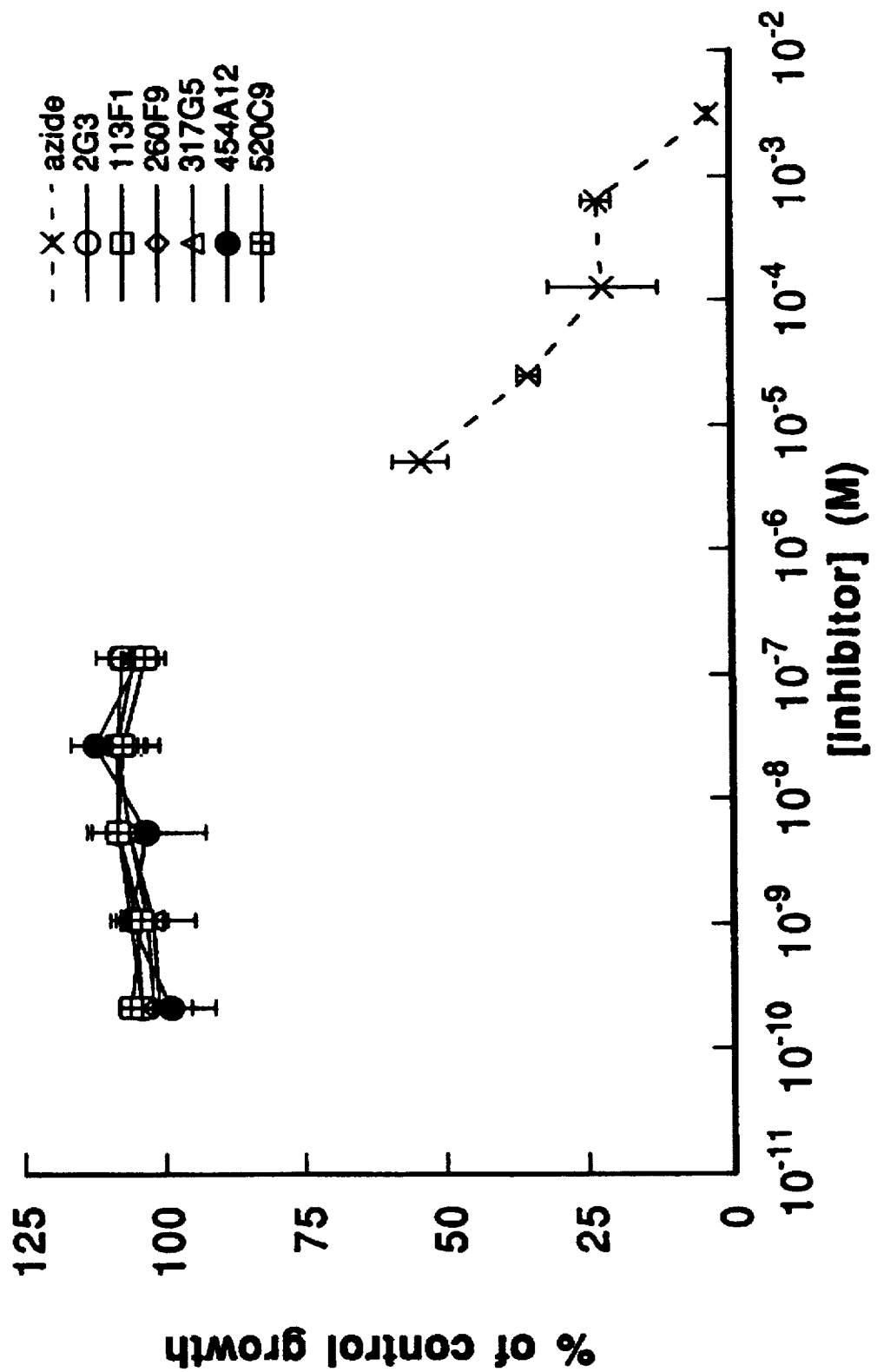
FIG. 1a through 1h show the growth inhibitory effects of various concentrations of monoclonal antibodies and bispecific antibodies on mammary epithelial cell line HBL-100 (FIGS. 1a and 1b), breast cancer cell line SK-Br-3 (FIGS. 1f, 1g and 1h) and colorectal cancer cell line HT29 (FIGS. 1c, 1d and 1e), with varying concentrations of sodium azide used as a control.

The present invention relates to antigen forks that inhibit cell growth and cause cell death, perhaps as a result of heterodimerizing and crosslinking of cell surface antigens. Antigen forks are molecules having at least two separate binding elements, each binding element being directed to a different antigen. The antigens to which the antigen fork binds are capable of being simultaneously expressed on the surface of at least one target cell type and differ from each other in at least one cellular functional quality.

The antigen forks of the present invention may be constructed from any two binding elements where each binding element specifically binds to a different cell surface antigen. In a preferred embodiment of the present invention, the binding elements of the antigen fork are derived from monoclonal antibodies. Such antigen forks are considered a type of bispecific antibody. However, not all bispecific antibodies are antigen forks as defined herein because not all bispecific antibodies bind to two distinct antigens on the surface of one target cell or inhibit cell growth of the target cell by binding to the cell.

Moreover, antigen forks need not be constructed from antibodies. The binding capabilities of the antigen fork may be formed from components that are not limited to antibody-related binding, including, but not limited to, ligand or receptor subunits, and peptides or polypeptides and other molecules having binding capabilities to cell surfaces. Binding of the antigen fork to the cell leads to heterodimerization and crosslinking of cell surface antigens. This crosslinking, as opposed to monovalent binding of surface antigens, frequently leads to effects on signal transduction and antigen turnover. Furthermore, if the antigens crosslinked by the antigen fork have different biological functions, one or both of these function may be impaired by the crosslinking, leading to cell death or to inhibition of cell growth.

The types of cells affected by the antigen fork of the present invention, are determined by the particular cell surface antigens targeted, since antigen crosslinking by the antigen fork herein will only occur on cells in which both cell surface antigens are present. It is preferred that the antigen fork of the present invention be designed such that the two binding elements do not bind to surface antigens that are simultaneously expressed on the surface of normal cells. Moreover, the antigen forks of the present invention do not affect bystander cells exhibiting only one of the cell surface antigens. Such targeted cells include, but are not limited to, tumor cells and virus-infected cells.

The effect of the antigen fork on cell growth can be greatly enhanced by administering a cytotoxic or cytostatic agent with the antigen fork, either sequentially or simultaneously.

It is preferred that at least one of the cell surface antigens be a cell surface glycoprotein. It is also preferred that at least one of the antigens specifically bind to either 113F1, 317G5 or 454A12 monoclonal antibodies. It is further preferred that the other antigen of the antigen fork bind to a monoclonal antibody selected from the group consisting of 113F1, 317G5, 454A12, 2G3, 260F9, 520C9, 34F2 and 15D3, provided that the two antigens are different.

In a further embodiment of the present invention, at least one cell surface antigen binds to a monoclonal antibody directed to either a glycoprotein, a human transferrin receptor, a human c-erbB-2 proto-oncogene product or a mucin molecule, such as monoclonal antibodies 113F1, 317G5, 454A12, 2G3, 260F9, 520C9, 34F2 and 15D3.

The present invention also relates to a method for treating a patient with cancer or a viral infection by administering to the patient in need of such treatment an antigen fork of the present invention. It is preferred that a cytotoxic agent such as deferoxamine or cisplatin be sequentially or simultaneously administering to the patient.

While the binding elements of the antigen fork need not necessarily be derived from monoclonal antibodies, in a preferred embodiment of the present invention, the antigen fork is a bispecific antibody. Accordingly, in one aspect of the present invention, an antigen fork, preferably a bispecific antibody, capable of binding to a first antigen and a second antigen is provided, wherein the first and second antigens are capable of being simultaneously expressed on the surface of at least one cell type. In a preferred embodiment of this invention, the first and second antigens differ in at least one cellular functional quality, for example, enzymatic activity, endocytic rate, endocytic route, signal transduction, cellular membrane transport, cell surface mobility, and turnover rate. In a particularly preferred embodiment of this invention, the first antigen is a transferrin receptor and the second antigen has a different endocytic rate than the transferrin receptor.

Another aspect of the present invention relates to a method for inhibiting the growth of cells, for example, cancer cells or virus-infected cells. Such inhibition is achieved by contacting the target cells with an antigen fork of the present invention. Preferably, the target cells are also placed in contact with a cytostatic, cytotoxic or anti-viral agent, sequentially or simultaneously.

In another embodiment of the present invention, a method is provided for the treatment of a patient with cancer or other diseases by inhibiting the growth of the cancer or the affected cells. The method consists of administering a therapeutically effective amount of an antigen fork to the patient. The therapeutically effective amount may be determined by techniques conventional in the art based upon the effects observed herein.

The antigen fork administered to the patient may be administered in conjunction with a conventional chemotherapeutic agent used for the treatment of cancer, for example, deferoxamine or cisplatin, or an antiviral, cytotoxic or cytostatic agent. These agents may be administered sequentially or simultaneously.

The present invention, thus, also relates to the use of an antigen fork for treating a patient with cancer, including but not limited to breast cancer, colorectal cancer, erythroleukemia, sarcoma carcinoma, squamous carcinoma, testicular cancer, ovarian cancer and bladder cancer, by administering to the patient in need of such treatment a therapeutically effective amount of an antigen fork of the present invention. The antigen fork of the present invention treats cancer by inhibiting tumor cell growth when placed in contact with the tumor.

The invention described herein draws on previously published work and pending patent applications. By way of example, such work consists of scientific papers, patents or pending patent applications. All of these publications and applications, cited previously or below are hereby incorporated by reference. Although any similar or equivalent methods and materials may be employed in the practice or testing of the present invention, the preferred methods and materials are now described.

The invention also relates to a method of producing antigen forks. The method has the following steps: (a) contacting a homogeneous culture of cells with a first antibody, the first antibody having a binding site capable of recognizing and binding to a first antigen present on the surface of the cells under conditions allowing the first antibody to bind to the cells; (b) contacting a homogeneous culture of cells with a second antibody, the second antibody having a binding site capable of recognizing and binding to a second antigen present on the surface of the cells under conditions allowing the second antibody to bind to the cells, the first and second antibodies having at least one common epitope; (c) contacting the first and second antibodies with a third antibody, the third antibody capable of recognizing and binding the at least one common epitope under conditions allowing the third antibody to bind to the first and second antibodies; determining whether the the treatment of cells according to steps (a) through (c) results in a decrease in the viability of the cells; constructing the antigen fork using a molecule comprising the binding site from the first antibody and a molecule comprising the binding site from the second antibody when treatment of cells according to steps (a) through (c) results in a decrease in the viability of the cells. It has been found that few combinations of antibodies produce active antigen forks and generation of heteroconjugates by chemical cross-linking is time-consuming. By performing the method of the invention, those skilled in the art will be able to select pairs of antibodies for the production of antigen forks that will be strong candidates for use in the production of active antigen forks. The decrease in the viability of the cells may be measured by any means. The decrease may be measured, for example, by absorbance or by cell sorters and expressed as a percent relative to cells which have not been treated by the method of the invention. The decrease in viability may be a 25% to 100% increase, and the decrease in viability may be 50%.

The present invention may be better understood in light of the following definitions incorporated herein.

Definitions

As used herein, the term "antibody" refers to polyclonal antibodies, monoclonal antibodies, humanized antibodies, single-chain antibodies, and fragments thereof such as Fab, F(ab')2, Fv, and other antibody fragments which retain the antigen binding function of the parent antibody.

As used herein, the term "monoclonal antibody" refers to an antibody of uniform light and heavy chain composition that may be produced by a single hybridoma, hybrid hybridoma or trioma clone or by recombinant technology. The term "monoclonal antibody" is not limited to a particular species or source of the antibody, nor is it intended to be limited by the manner in which it is made. Rather, "monoclonal antibody" encompasses whole immunoglobulins as well as fragments such as Fab, F(ab')2, Fv, and other antibody fragments that retain the antigen binding function of the parent monoclonal antibody. Recombinant forms of these antibodies or fragments may be produced in any expression system conventional in the art, such as prokaryotic, as in E. coli, or eukaryotic, as in yeast, insect or mammalian cells.

Monoclonal antibodies of any mammalian species can be used in this invention, including but not limited to human, mice, rats, rabbits, goats, sheep, bovine, porcine and equine or combinations thereof. Antibodies of murine or rat origin are preferred in view of the availability of murine or rat cell lines for use in making the required hybrid cell lines and hybridomas to produce the monoclonal antibodies.

As used herein, the term "humanized antibody" means that at least a portion of the framework regions of an immunoglobulin is derived from human immunoglobulin sequences.

As used herein, the term "single chain antibody" refers to an antibody prepared by combining the binding domains (both heavy and light chains) of an antibody with a linking moiety that preserves the binding function. This forms, in essence, a radically abbreviated antibody, having only that part of the variable domain necessary for binding to the antigen. Single chain antibodies can be prepared as described in U.S. Pat. No. 4,946,778 to Ladner et al.

As used herein, the term "bispecific antibody" refers to any antibody that has binding specificity for two different antigens, whether naturally occurring or synthetically made in vitro. Bispecific antibodies include molecules formed by chemically conjugating two different antibodies. B. Karpovsky, et al. (1984) *J. Exp. Med.* 160(6):1686–1701; M. Brennan, et al., *Science* (1985) 229:(1708):81–83. Alternatively, bispecific antibodies may be produced from a "hybrid hybridoma," a cell fusion of two monoclonal antibody-producing cells, as shown, for example, in U.S. Pat. No. 4,474,893 to Reading; C. L. Reading, in HYBRIDOMAS AND CELLULAR IMMORTALITY, B. H. Tom et al., eds., 1984, (New York: Plenum Press), p. 235; U. D. Staerz et al., *Proc. Natl. Acad. Sci.* (1986) 83:1453–1457; A. Lanzavecchia et al., *Eur. J. Immunol.* (1987) 17:105–111; D. B. Ring et al., in BREAST EPITHELIAL ANTIGENS: MOLECULAR BIOLOGY TO CLINICAL APPLICATIONS, R. Ceriani, ed., 1991, (New York: Plenum Press), pp. 91–104.

As used herein, the term "cellular functional quality" refers to a quality of a cell surface antigen relating to its normal function in cellular activity. Examples of cellular functional qualities include, but are not limited to endocytic rate, endocytic route, signal transduction, cellular membrane transport, cell surface mobility, turnover rate and enzymatic activity.

As used herein, the term "cytostatic" means preventing cell proliferation, while "cytotoxic" means causing cell death. Agents that diminish cell proliferation below control levels, but do not cause the initial cell count to decrease, are generally termed cytostatic. Agents that reduce original cell count are generally termed cytotoxic.

The Antigen Fork

The present invention relates to antigen forks, which are molecules that contain binding elements to two different antigens capable of being simultaneously expressed on the surface of at least one target cell type. It is preferred that the antigen fork be a bispecific antibody. However, the binding capabilities of the antigen fork may be formed from components that are not related to antibody binding sites.

Other useful binding elements include, but are not limited to ligand or receptor subunits, and peptides and other small molecules having binding capabilities to cell surfaces. Thus, the antigen forks contemplated by the invention include molecules that are formed by linking any two binding elements, including antibodies, peptides, small molecules, polypeptides, cell adhesion molecules, one member of a ligand/receptor binding pair, or specifically binding portions thereof.

In one embodiment of the present invention, the two binding elements may be a fusion protein, one portion of which constitutes the first binding element and another portion of which constitutes the second binding element.

The binding elements herein include, for example, any naturally occurring peptides or polypeptides such as bombesin, vasopressin, heregulin, urokinase, growth factors, colony stimulating factors (e.g., MCSF), c-fms, cytokines, and ICAM-1. Such binding elements may be produced synthetically or by recombinant techniques conventional in the art based upon known chemical composition such as amino acid sequence or DNA or mRNA sequence.

Antibody Preparation

Bispecific antibody versions of the antigen forks of the invention may be prepared in a two-step method. First, monoclonal antibodies specific for each cell surface antigen to be bound by the antigen fork are prepared. Then, monoclonal antibodies specific for each of the cell surface antigens to be bound by the antigen fork, or hybridomas that produce these monoclonal antibodies, are used to prepare a bispecific antibody. The resulting bispecific antibody possesses the binding specificities to cell surface antigens of both of the antibodies used to construct the bispecific antibody. Monoclonal antibodies that may be used to prepare the antigen forks of the present invention include the specific antibodies disclosed herein as well as antibodies now known or developed in the future.

A. Monoclonal Antibodies

Monoclonal antibodies are prepared by techniques conventional in the art, such as the method of Kohler and Milstein, Nature (1975) 256:495–96, or a modification thereof. Typically, an animal, such as a mouse or rat, is immunized as described in Kohler and Milstein, Nature (1975) 256:495–96. However, rather than bleeding the animal to extract serum, the spleen (and optionally several large lymph nodes) are removed and dissociated into single cells.

If desired, the nonspecifically adherent cells may be removed and the remaining spleen cells screened by applying a cell suspension thereof to a plate or well coated with a protein antigen. B-cells in the spleen cell population expressing membrane-bound immunoglobulin specific for the antigen bind to the plate. The plate is rinsed to remove cells that are not bound to the plate. The resulting bound B-cells, or, in the alternative, all dissociated spleen cells, are induced, for example with PEG, to fuse with drug-resistant myeloma cells to form hybridomas. The resulting hybridomas are cultured in a selective medium, for example, hypoxanthine, aminopterin, thymidine medium, "HAT", that selects for the presence of a fused B cell and myeloma cell. The resulting hybridomas are plated by limiting dilution, and are assayed for the production of antibodies which bind specifically to the desired immunizing antigen, in this case a cell-surface antigen. The hybridomas are also assayed for the production of antibodies which bind to unrelated antigens.

Alternatively, known hybridomas that secrete a desired monoclonal antibody ("MAb") may be used, for example, those deposited at American Tissue Culture Collection in Rockville, Md. or other known sources.

The selected MAb-secreting hybridomas may, if necessary, be subcloned by, for example, plating at a limiting dilution in order to obtain subclones that exhibit stable monoclonal antibody secretion. Subclones that secrete antibody may be identified by the same assays used to identify the original clones. Selected MAb-secreting clones or subclones are then cultured either in vitro, for example, in tissue culture, fermentors, or hollow fiber reactors, or in vivo, for example, as ascites in mice.

B. Bispecific Antibodies

Bispecific antibodies are generally obtained in one of two ways: (1) generation by chemical linkage; or (2) production by engineered cell lines. Chemical linkage involves the linking of either two entire monoclonal or polyclonal antibodies, or antigen-specific fragments thereof (B. Karpovsky et al., *J. Exp. Med.* (1984) 160:1686–1701; U. D. Staerz et al., *Nature* (1985) 314:628–631; M. J. Glennie et al., *J. Immunol.* (1987) 139:2367–2375). Two such entities having different specificities are linked using a chemical crosslinking agent such as SPDP (N-succinimidyl 3-(2-pyridyldithio)-propionate) or other crosslinking agents conventional in the art. Alternatively, each antibody may be digested to produce F(ab')2 fragments, which may then be reduced to produce individual Fab' fragments. One Fab' fragment may then be derivatized with a reagent such as o-phenylene dimaleimide, and this derivatized Fab' fragment may then be reacted with the second Fab' fragment of different specificity to regenerate a linkage at the hinge region and create a bispecific F(ab')2 fragment. Whether whole parental antibody molecules or Fab' fragments are linked, it is advantageous to modify one antibody before reacting it with the second antibody, since this type of asymmetric reaction sequence maximizes the formation of heterodimers and eliminates or minimizes formation of homodimers that are not bispecific. In any case, it may be necessary to purify resulting bispecific antibodies from unreacted parental antibodies, homodimers and larger oligomers. This may be accomplished by standard chromatographic techniques such as ion exchange, size exclusion or affinity chromatography.

Alternatively, two cell lines that produce different antibodies may be fused to generate a hybrid cell line that produces bispecific antibodies. C. L. Reading, in HYBRIDOMAS AND CELLULAR IMMORTALITY, B. H. Tom et al., eds., 1984, (New York: Plenum Press), p. 235; U. D. Staerz et al., *Proc. Natl. Acad. Sci.* (1986) 83:1453–1457; A. Lanzavecchia et al., *Eur. J. Immunol.* (1987) 17:105–111; D. B. Ring et al., in BREAST EPITHELIAL ANTIGENS: MOLECULAR BIOLOGY TO CLINICAL APPLICATIONS, R. Ceriani, ed., 1991, (New York: Plenum Press), pp. 91–104). If the two cell lines that are fused are originally hybridomas, the resulting hybrid is a "hybrid hybridoma". If one fusion partner is a hybridoma and the other is a B cell or myeloma, the resulting hybrid is a "trioma." If both fusion partners are B cells or myelomas, the resulting hybrid is a "hybridoma."

A hybrid hybridoma or other hybrid cell line that produces a bispecific antibody will generally also produce both parental antibodies. In some cases, the light chain of each parental antibody will preferentially associate with its corresponding heavy chain, so that only bispecific and parental antibodies are formed in significant amounts. In other cases, one or both of the light chains will associate indiscriminately with either of the parental heavy chains, leading to the formation of additional immunoglobulin species containing inactive binding elements formed by mispaired light and heavy chains. In general, it will be necessary to purify the desired active bispecific antibody from parental antibodies or inactive immunoglobulins. This may be accomplished by standard chromatographic techniques such as ion exchange, size exclusion, hydrophobic interaction or affinity chromatography.

It is also possible to produce bispecific antibodies in various host cell types, for example, bacterial, yeast, insect or mammalian, by transfection of host cells with appropriate vectors, or by infection of host cells with appropriate viruses containing immunoglobulin light and heavy chain genes or engineered genes coding for modified or single chain antibody binding elements. In particular, the genes for two single chain antibody binding elements may be connected by an appropriate linker to generate a single gene coding for a single chain bispecific antibody, which may then be produced in an appropriate cellular expression system. J. S. Huston et al, in BISPECIFIC ANTIBODIES AND TARGETED CELLULAR CYTOTOXICITY: PROCEEDINGS OF THE SECOND INTL. CONFERENCE, J. L. Romet-Lemonne et al., eds., 1991, pp. 201–206.

Compositions and Formulations

The antigen forks of this invention are administered at a concentration that is therapeutically effective to kill or halt growth of the desired targeted cells. To accomplish this goal, the antigen forks are placed in contact with the targeted cells. In a preferred embodiment, the antigen forks are administered intravenously where they can travel in vivo to the targeted cells. Methods to accomplish this administration are conventional and are known to those of ordinary skill in the art.

Before administration of an antigen fork to a patient, formulants may be added to the antigen fork. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono-, di-, or polysaccharides, or water soluble glucans. Saccharides or glucans that can be used include, but are not limited to, fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. Sucrose is most preferred. These sugars or sugar alcohols mentioned above may be used individually or in combination. There is no fixed limit to the amount used as long as the sugar or sugar alcohol is soluble in the aqueous preparation. Preferably, the sugar or sugar alcohol concentration is between 1.0 and 7.0 w/v %, more preferably between 2.0 and 6.0 w/v %. Preferably amino acids include levorotary (L) forms of carnitine; arginine, and betaine; however, other amino acids may be added. Preferred polymers include polyvinylpyrrolidone (PVP) with an average molecular weight between 2,000 and 3,000 and polyethylene glycol (PEG) with an average molecular weight between 3,000 and 5,000. It is also preferred to use a buffer in the composition to minimize pH changes in the solution before lyophilization or after reconstitution. Almost any physiological buffer may be used. However, citrate, phosphate, succinate, and glutamate buffers or mixtures thereof are preferred. The most preferred buffer is a citrate buffer. Preferably, the buffer concentration is between about 0.01 to 0.3 molar. Surfactants that can be added to the formulation are shown in European Patent Application Nos. 270,799 and 268,110.

Additionally, an antigen fork can be chemically modified by covalent conjugation to a polymer, for example, to increase its circulating half-life. Preferred polymers, and methods to attach them to peptides, are shown in U.S. Pat. Nos. 4,766,106; 4,179,337; 4,495,285; and 4,609,546, which are all hereby incorporated by reference in their entireties. Preferred polymers are polyoxyethylated polyols and polyethylene glycol (PEG). PEG is soluble in water at room temperature and has the general formula: R(O—CH$_2$—CH$_2$)$_n$—O—R where R can be hydrogen, or a protective group such as an alkyl or alkanol group. Preferably, the protective group has between 1 and 8 carbons; more preferably it is methyl. The symbol n is a positive integer, preferably between 2 and 1,000, more preferably between 2 and 500. It is preferred that PEG have an average molecular weight of between 1000 and 40,000, more preferably between 2000 and 20,000, most preferably between 3,000 and 12,000. Preferably, PEG has at least one hydroxy group, more preferably it has a terminal hydroxy group. It is this hydroxy group which is preferably activated to react with a free amino group on the inhibitor. However, it will be understood that the type and amount of the reactive groups may be varied to achieve a covalently conjugated PEG/antigen fork of the present invention.

Water soluble polyoxyethylated polyols are also useful in the present invention. They include polyoxyethylated sorbitol, polyoxyethylated glucose, polyoxyethylated glycerol (POG), etc. POG is preferred, in part because the glycerol backbone of POG is the same as the backbone occurring naturally in, for example, animals and humans in mono-, di- and triglycerides. Therefore, this branching will not necessarily be seen as a foreign agent in the body. POG has a preferred molecular weight in the same range as PEG. The general structure of POG is shown in Knauf et al., *J. Biol. Chem.* (1988) 263:15064–15070, and a discussion of POG/polypeptide conjugates is found in U.S. Pat. No. 4,766,106, both of which are hereby incorporated by reference in their entireties.

After the liquid pharmaceutical composition is prepared, it is preferably lyophilized to prevent degradation and to preserve sterility. Methods for lyophilizing liquid compositions are known to those of ordinary skill in the art. Thus, prior to use, the composition may be reconstituted with a sterile diluent, for example, Ringer's solution, distilled water, or sterile saline, which may include additional ingredients. Upon reconstitution, the composition is preferably administered to subjects using those methods that are known to those skilled in the art.

In preferred embodiments of this invention, cytotoxic or cytostatic agents are co-administered with the antigen fork. Examples of such agents include numerous cytotoxic drugs that are used in cancer chemotherapy such as antimetabolites, for example, 5-fluorouracil, methotrexate, DNA crosslinking agents, e.g., cisplatin, DNA intercalators, e.g., doxorubicin, agents that disrupt the cytoskeleton or cell cycle, e.g., vinblastine, colchicine, and iron chelators, e.g., deferoxamine and cardioxane. Cytotoxic and cytostatic agents also include antiviral agents such as AZT, DDI, DDC and ribavarin. Preferred agents are deferoxamine and cisplatin.

Frequently, such drugs are highly toxic to normal cells as well as cancer cells, and the resulting side effects limit their use in therapy. Combinations of cytotoxic drugs often have synergistic effects and lower the concentrations of drug needed to kill tumor cells, which may reduce side effects to normal tissues if different normal tissues are affected by the drugs that are combined. Similarly, an antigen fork that selectively inhibits tumor versus normal cells may increase the sensitivity of the tumor cells to a cytotoxic drug, allowing that drug to be used at a lower concentration that will cause less toxicity to normal tissues.

Administration to Affected Individuals

As stated above, the antigen forks of the present invention are useful for inhibiting tumor cell growth and for treating human patients with cancers, such as adenocarcinomas. These cancer cells are characterized by expressing two different cell surface antigens to which the antigen fork has separate binding elements. A preferred means for delivering the antigen forks to the target cells is intravenous administration. Generally, antigen forks are given at a dose between 1 µg/kg and 20 mg/kg, more preferably between 20 µg/kg and 10 mg/kg, most preferably between 1 and 7 mg/kg. Administration may be as a bolus dose, to increase circulating levels by 10–20 fold and for 4–6 hours after the bolus dose. Continuous infusion may also be used after the bolus dose. If so, the antigen forks may be infused at a dose between 5 and 20 µg/kg/min, more preferably between 7 and 15 µg/kg/min.

The antigen forks of the invention may be given in combination with other cytotoxic or cytostatic agents. For example, the following may be administered in combination with the antigen forks of the invention. Deferoxamine is given in a dose between 10 µg/kg and 20 mg/kg as deferoxamine mesylate, preferably between 1 and 10 mg/kg; or infused continuously at a dose of between 10 and 250 µg/kg/minute. Cisplatin is given in the following doses: 20 mg/m$^2$ i.v. daily for 5 days to treat metastatic testicular cancer; 100 mg/m$^2$ i.v. once every 4 weeks to treat metastatic ovarian cancer; 50–70 mg/m$^2$ i.v. once every 3–4 weeks to treat advanced bladder cancer.

While the present invention provides specific antigen forks and specific cells which may be treated by these antigen forks, the present invention also generally teaches one of ordinary skill how to prepare antigen forks as well as how to screen the antigen forks for cell growth inhibiting activity. In view of this teaching, additional antigen forks not specifically disclosed can be prepared and screened for activity by those of ordinary skill without undue experimentation.

The present invention will now be illustrated by reference to the following examples which set forth particularly advantageous embodiments. However, it should be noted that these embodiments are illustrative and are not to be construed as restricting the invention in any way.

EXAMPLE 1

Binding of Monoclonal Antibodies to Cell Lines

Nine monoclonal antibodies, listed in Table 1, or a subclone thereof, were selected as potential precursors or parental antibodies to the antigen forks of this invention. These antibodies were selected because of their ability to selectively bind to a cell surface antigen known to be present on the surface of at least one cancer cell type. Selection of other antibodies that bind to an antigen found on the surface of a cancer cell is within the level of ordinary skill in the art.

TABLE 1

| Antigen Fork Component Antibodies | |
|---|---|
| 2G3 | Murine IgG1 recognizing a high molecular weight mucin; relatively poor endocytosis. |
| 34F2, 317G5, 650E2 | Murine IgG1 recognizing a 42 kd glycoprotein particularly prevalent in colorectal tumors; moderately rapid endocytosis. |
| 113F1 | Murine IgG3 recognizing a carbohydrate determinant on a poorly characterized glycoprotein complex; moderately rapid endocytosis. |
| 260F9 | Murine IgG1 recognizing a 55 kilodalton tumor associated glycoprotein; moderately rapid endocytosis. |
| 454A12 | Murine IgG1 recognizing human transferrin receptor; extremely rapid and efficient endocytosis. |
| 520C9 | Murine IgG1 recognizing human c-erbB-2 proto-oncogene product; moderately rapid endocytosis. |
| 15D3 | Murine IgG1 recognizing human P-glycoprotein (multidrug resistance protein); endocytosis not known. |

Frankel, et al. (1985) "Tissue distribution of breast cancer associated antigens defined by monoclonal antibodies" *J. Biol. Resp. Modif.* 4:273–286.

The ability of some of the antibodies listed in Table 1 to bind to various cancer cell lines was tested using the following live cell indirect immunofluorescent assay protocol. This protocol may also be used to routinely screen for other antibodies which may be used in the fabrication of an antigen fork.

Protocol 4 to $8 \times 10^4$ cells for each cell line to be tested were incubated overnight in growth medium consisting of Iscove's modified Dulbecco's medium+10% heat inactivated fetal bovine serum+2 mM glutamine in each chamber of an eight-chambered slide (Lab-Tek). Cells were washed with phosphate buffered saline (PBS) containing $Ca^{+2}$, $Mg^{+2}$ and 1% bovine serum albumin (BSA) and incubated for 30 minutes at 4° C. with 40 µg/ml purified monoclonal antibody. Cells were washed again and incubated for 30 minutes at 4° C. with 20 µg/ml fluorescein-labeled goat F(ab')2 anti-mouse IgG (Zymed). After three washes, cells were fixed in 1.5% formaldehyde in PBS containing $Ca^{+2}$ and $Mg^{+2}$, and the chamber and gasket were removed. The slide was air-dried and mounted with Aqua-Mount (Scientific Products) and examined under fluorescent microscopy.

Antibody binding was also assessed by flow cytometry, again using an indirect immunofluorescence technique. $1 \times 10^6$ cells were washed with PBS containing 1% bovine serum albumin (PBS/BSA) and incubated for 30 min at 4° C. in PBS/BSA containing the first antibody at a final dilution of 20 µg/ml. After washing three times in PBS/BSA, the cells were incubated with FITC-conjugated $F(ab')_2$ fragment of goat anti-(mouse IgG Fc) (Jackson Immuno Research) for another 30 min at 4° C. The last wash contained 50 µg/ml propidium iodide to stain dead cells. Samples were analyzed on a Coulter EPICS V cell sorter. Dead cells and cellular debris were eliminated based on their forward angle light scatter and red fluorescence. At least 20,000 live cells were scored for each sample and the intensity of green fluorescence was measured on a logarithmic scale.

Results of both binding assays are shown in Table 2.

TABLE 2

| Cell line binding of antigen fork component antibodies. | | | | | | | |
|---|---|---|---|---|---|---|---|
| Cell Line | Assay | 2G3 | 113F1 | 260F9 | 317G5 | 454A12 | 520C9 |
| HBL-100 | LCI[1] | ± | + | 0 | 0 | ± | 0 |
|  | FC[2] | + | + | ± | 0 | + | 0 |
| HT29 | LCI | 0 | + | + | ++ | + | ± |
|  | FC | 0 | 0 | 0 | ++ | + | ± |
| SK-BR-3 | LCI | ++ | ++ | ++ | ++ | + | ++ |
|  | FC | + | ++ | ++ | ++ | + | ++ |
| SK-OV-3 | FC | ± | 0 | + | + | + | ++ |
| SW948 | FC | 0 | ++ | 0 | ++ | + | ± |

[1]LCI = live cell indirect immunofluorescence assay in eight-chambered slides
[2]FC = flow cytometry In general, there was a good correlation between the two assays, except that HT29 cells scored negative for 113F1 and 260F9 binding by flow cytometry, but weakly positive by immunofluorescence on slides. This discrepancy may reflect "cropping" caused by channel selection during flow cytometry; i.e., the lowest fluorescent channel scored may have been too high to show weakly positive staining.

EXAMPLE 2

Generation of Antigen Fork Heteroconjugates

Antigen fork heteroconjugates of whole antibodies ("whole AHC forks") may be produced by derivatizing two monoclonal antibodies of different antigenic specificity with SPDP, deblocking one derivatized antibody with DTT, reacting it with the second derivatized antibody in a directed coupling, and separating uncoupled monomeric immunoglobulin from whole AHC forks by HPLC sizing, according to the following protocols:

A. SPDP Derivatization

The two antibodies to be coupled (antibodies "A" and "B") were separately concentrated to 10–20 mg/ml using a Centricon 100 apparatus (Amicon), and dialyzed into coupling buffer (100 mM $KPO_4$, 100 mM NaCl, pH 7.5). Each antibody was stirred for 3 hrs at room temperature with a six-fold molar excess of SPDP (N-succinimidyl 3-(2-pyridyldithio)propionate; Pierce) pre-dissolved at 6.25 mg/ml in dimethyl sulfoxide ("DMSO") before adding to the antibody solution. Excess SPDP was removed by chromatography of the antibody solution over PD10 columns (Pharmacia). Antibody A was chromatographed in acetate buffer (100 mM sodium acetate, 100 mM NaCl, pH 4.5) and antibody B in PBS (20 mM $NaPO_4$, 150 mM NaCl, 1 mM EDTA, 0.02% $NaN_3$, pH 7.2). In either case, fractions were monitored by absorbance at 280 nm and protein-containing fractions were pooled.

B. Coupling

Derivatized antibody A in acetate buffer was brought to 40 mM DTT (Sigma) by the addition of 24 mg/ml dithiothreitol (DTT) in acetate buffer, and stirred 30 min at room temperature. Derivatized antibody A was then chromatographed on a PD10 column in PBS to remove excess DTT, and peak fractions were again pooled based on absorbance at 280 nm. Derivatized antibody A prepared in this manner was then immediately combined with derivatized antibody B, as prepared above, in a 1:1 molar ratio. Coupling was allowed to proceed for 4 hours at room temperature. At the end of this incubation, the reaction was stopped and excess free thiol groups were blocked by addition of 100 mg/ml iodoacetamide, specifically, 1 mg iodoacetamide to a reaction containing 10 mg of each antibody.

C. Purification

The coupling reaction mixture was centrifuged for 30 sec at 12,000 rpm in an Eppendorf Microfuge, applied to a Bio-Sil TSK400 HPLC column equilibrated in PBS, and eluted at room temperature with PBS at a flow rate of 0.7 ml/min, collecting 0.375 ml fractions and monitoring absorbance at 280 nm. Fractions were analyzed by nonreduced SDS PAGE on 4–15% gradient Phast gels (Pharmacia). Fractions containing monomeric immunoglobulin were discarded, and fractions containing dimers and low oligomers were pooled for further use.

D. Heteroconjugate Formation

All 15 possible heterologous whole AHC forks derived from monoclonal antibodies 2G3, 113F1, 260F9, 317G5, 454A12 and 520C9, as well as the whole AHC fork 15D3-454A12 were synthesized by the method of Examples 2A-C above.

EXAMPLE 3

Generation of Monovalent Antigen Forks

The antigen forks synthesized in Example 2D above are whole AHC forks constructed from whole IgG molecules, and therefore contain at least two binding elements of each antigenic specificity. In contrast, the bispecific antibodies produced by a hybrid hybridoma are single immunoglobulin molecules containing only one copy of each binding site. Because they are based on whole antibody molecules, whole AHC forks have a higher total valency and can cause both homologous and heterologous crosslinking of surface antigens on target cells, while bispecific forks made by hybrid hybridomas should only be able to cause heterologous crosslinking. Homologous crosslinking refers to crosslinking between the same type of antigen. Heterologous crosslinking refers to crosslinking between different types of antigens.

It was of interest to determine whether antigen forks containing only one copy of each binding site were still able to inhibit cell growth. Such "monovalent" forks can be made not only by hybrid hybridomas, but also by directed linking of antibody Fab or Fab' fragments.

In order to test the activity of a monovalent version of the active 317G5-454A12 fork, each component antibody was convened to F(ab')2 fragments by pepsin digestion. The F(ab')2 fragments were reduced to Fab' fragments, and sequentially reacted with o-phenylene dimaleimide (o-PDM) to generate F(ab')2 heterodimers or monovalent antigen fork heterodimers ("MAFHDs").

A. F(ab')2 Fragment Production

Antibodies were concentrated to 8 mg/ml and dialyzed to 50 mM sodium titrate (pH 5). Immobilized pepsin (Pierce) was added at a 1:50 (w/w) pepsin to antibody ratio, and the mixture was brought to pH 3.25 using 1M citric acid. The digestion mixture was rotated for 2 hrs at 37° C., centrifuged 5 min at 2000×g, and the supernatant removed from the immobilized pepsin. The supernatant was immediately brought to pH 7 by the addition of 1 M tris-HCl, pH 8, and then dialyzed to PBS. The dialysate was applied to an AcA44 gel filtration column and eluted with PBS. Fractions were analyzed by nonreduced SDS PAGE (Phastgel, Pharmacia) and fractions containing pure F(ab')2 were pooled for further use.

B. Fab' Fragment Preparation

The two F(ab')2 fragments to be coupled were separately concentrated to 10 mg/ml using a Centricon 30 apparatus (Amicon), and dialyzed into 200 mM tris-HCl buffer, 10 mM EDTA, pH 8.0. Each F(ab')2 fragment was reduced to Fab' fragments by the addition of 2-mercaptoethanol (Sigma) to 20 mM for 30 min at 30° C. Both reduced Fab' samples were chilled to 4° C. and kept at that temperature through the remainder of the coupling and purification process. Excess mercaptoethanol was removed by chromatography on PD10 columns (Pharmacia) equilibrated in 50 mM sodium acetate, 0.5 mM EDTA, pH 5.3. Fractions were monitored by absorbance at 280 nm and protein-containing fractions were pooled.

C. Coupling

A half volume of 12 mM o-PDM dissolved in chilled dimethylformamide (Sigma) was added to one of the two Fab' fragment preparations. After 30 min, the derivatized Fab' was separated from unreacted o-PDM on a PD10 column in pH 5.3 acetate buffer as above, and immediately combined at 1 to 1.3 molar ratio with the other Fab' fragment and concentrated to approximately 5 mg/ml on a Centricon 30 apparatus. After incubation for 18 hrs, the reaction mixture was adjusted to pH 8.0 using 1M tris-HCl, pH 8.0, reduced with 2-mercaptoethanol at a final concentration of 20 mM for 30 min at 30° C., and alkylated with 20 mM iodoacetamide. This reduction and alkylation step eliminates any Fab' dimers formed by hinge thiol re-oxidation versus o-PDM linkage.

D. Purification

The reaction mixture was centrifuged for 30 sec at 12,000 rpm in an Eppendorf Microfuge, applied to a Bio-Sil TSK400 HPLC column equilibrated in 0.2 M tris-HCl, 10 mM EDTA, pH 8.0, and eluted at room temperature at a flow rate of 0.7 ml/min, collecting 0.375 ml fractions and monitoring absorbance at 280 nm Fractions were analyzed by nonreduced SDS PAGE on 8–25% gradient Phast gels (Pharmacia). Fractions containing monomeric Fab' were discarded, and fractions containing dimers were pooled for further use.

E. Monovalent Antigen Fork Heterodimer (MAFHD) Formation

The 317G5 Fab'-454A12 Fab' MAFHD was prepared by the procedure of Example 3A-D above.

EXAMPLE 4

Cell Growth Inhibition by Bispecific vs. Monospecific Antibodies

The ability of monoclonal and antigen fork bispecific antibodies to inhibit the growth of various target cancer cell lines was studied using the following assay. 5,000 to 10,000 target cells in 100 gl growth medium were seeded in triplicate in 96-well flat-bottom tissue culture plates, and incubated overnight at 37° C. in 5% $CO_2$. Serial two-fold dilutions of antibodies were made in the wells leaving 100 µl final volume per well, and the plates were incubated for 3 to 6 days.

An MTT (3-(4,5-dimethylthiazol-2-yl)-2,5-diphenyl tetrazolium bromide) assay kit (CellTiter 96, #G4100, Promega) was used to evaluate the number of viable cells remaining in the wells. 15 µl of dye solution was added per well and the plate was incubated for 4 hrs at 37° C. in 5% $CO_2$ followed by addition of 100 µl solubilization solution. Plates were read for absorbance at 570/630 nm on an ELISA plate reader after all blue crystals had dissolved (typically 1–5 days at room temperature in a moist chamber).

HBL100, a non-tumorigenic human mammary cell line, was used as a negative control because it is negative or only weakly positive for expression of the antigens recognized by the antibodies tested. HT29 and SK-Br-3 are, respectively, human colorectal and breast cancer cell lines. In all cases, varying concentrations of sodium azide were used as a control cytotoxic agent and all three cell lines were killed by this agent.

Figure 1B:
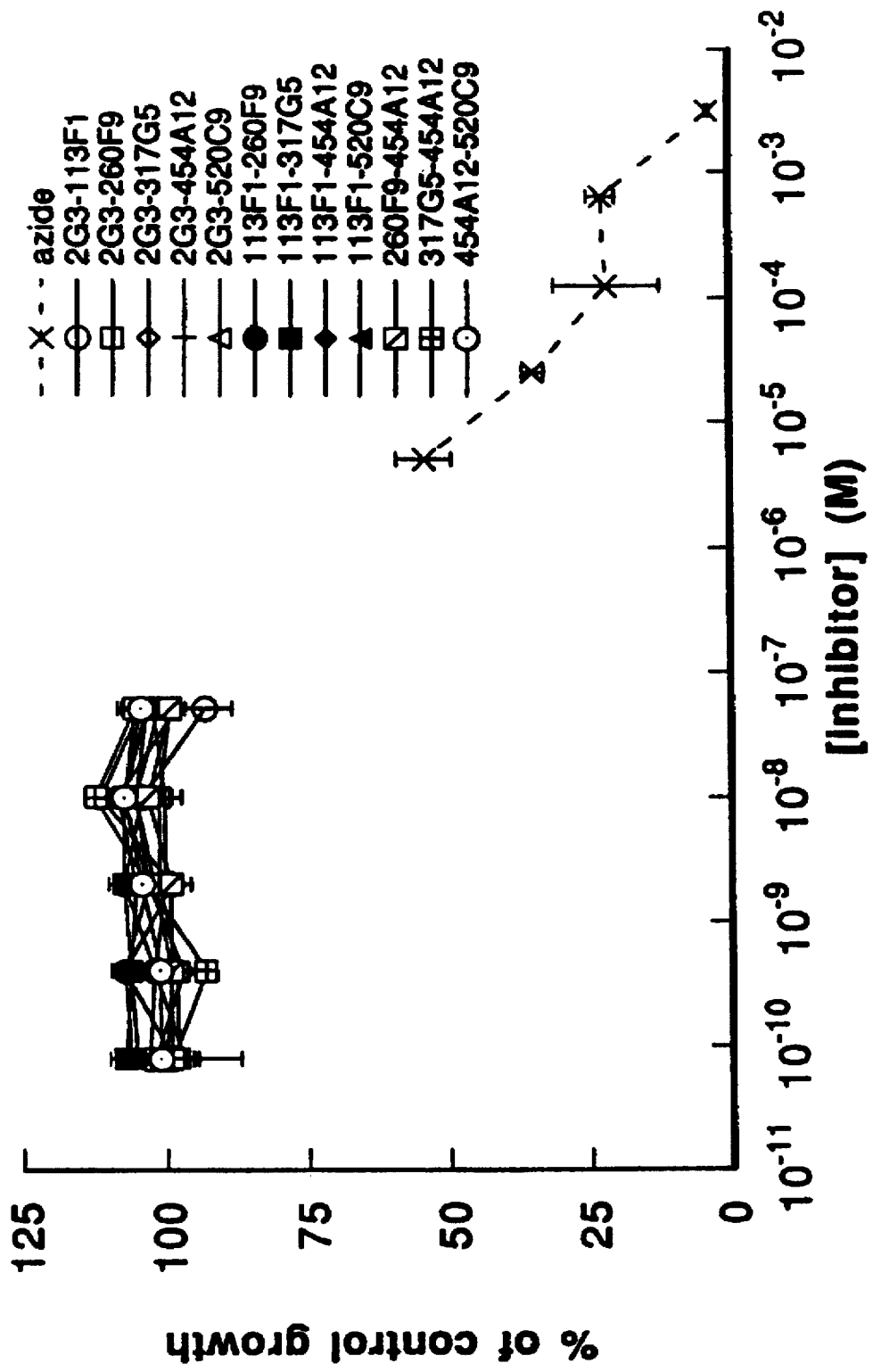
Figure 1C:
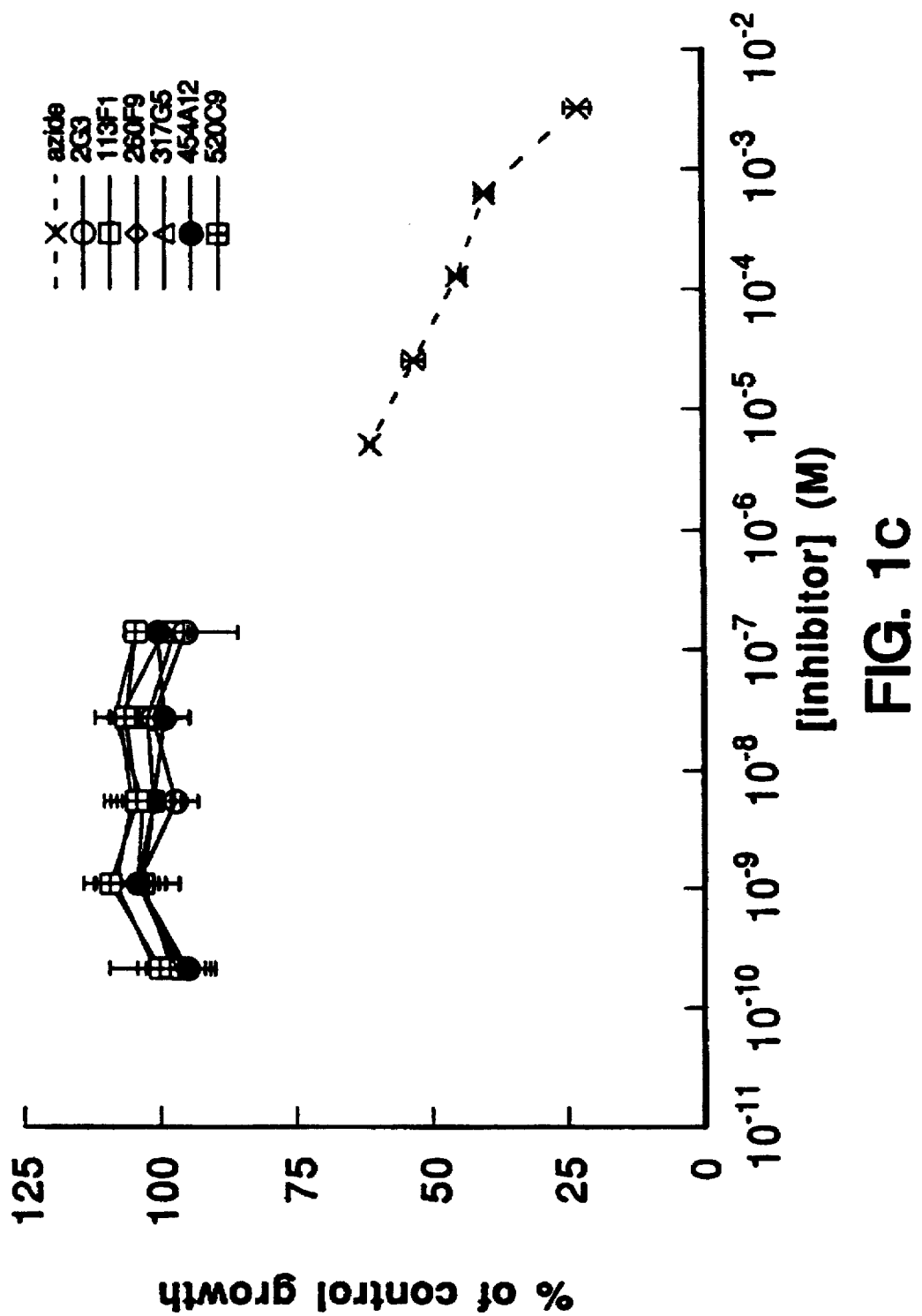
Figure 1D:
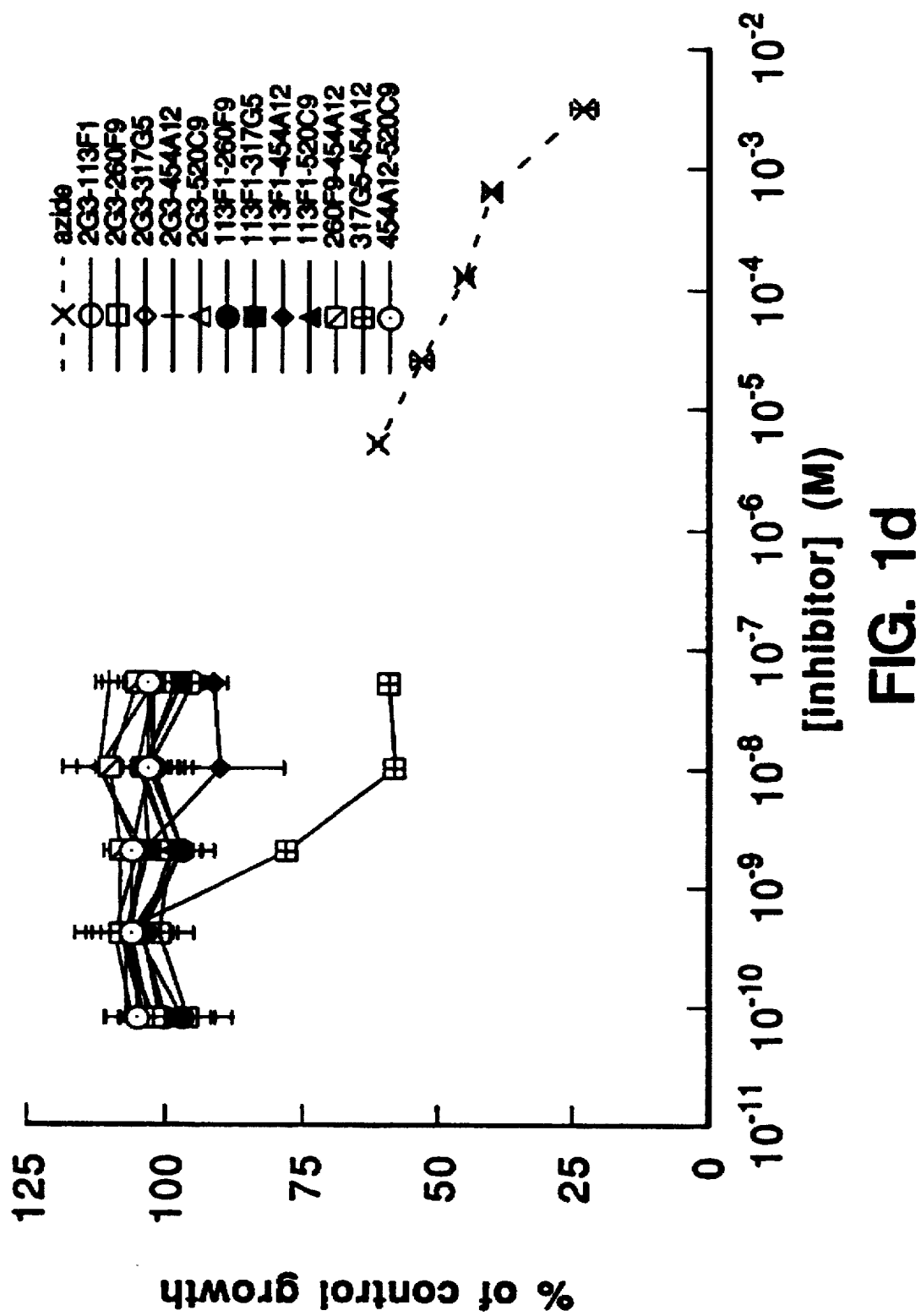
Figure 1E:
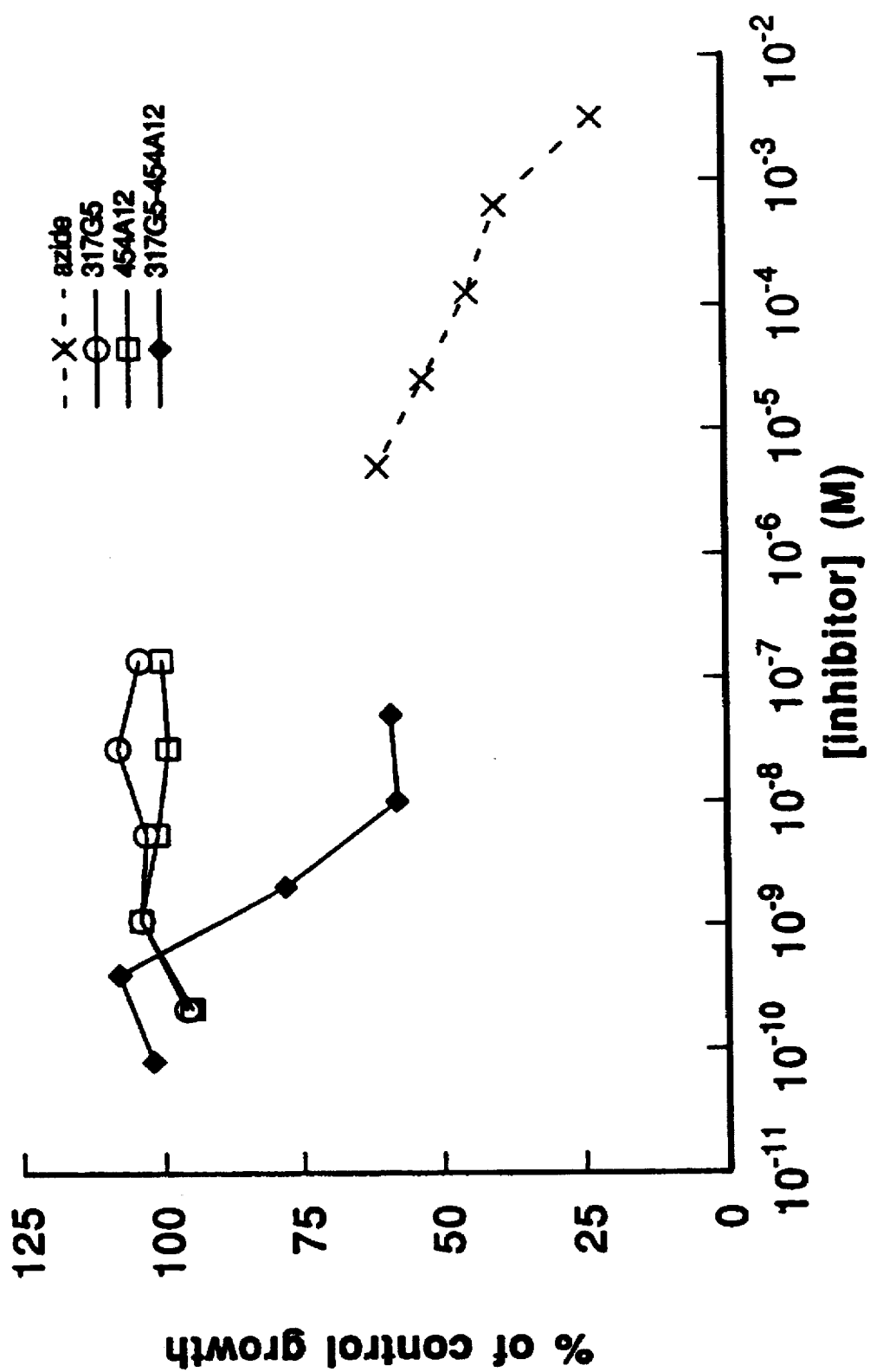
Figure 1F:
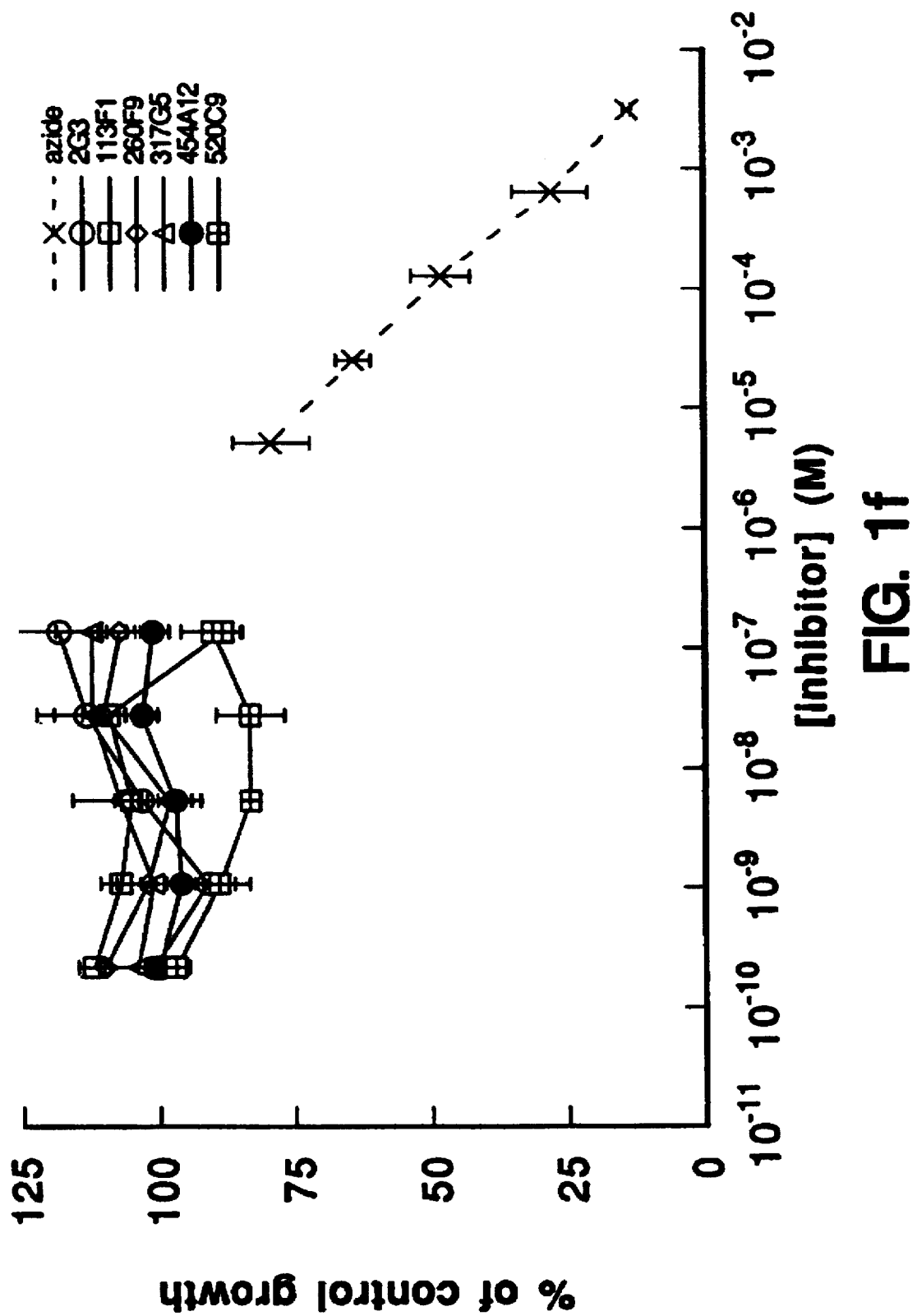

FIGS. 1a, c, and f show the effects of various concentrations of monoclonal antibodies on the growth of breast or colorectal cell lines, while FIGS. 1b, d and g show similar results for the designated whole AHC forks synthesized from those antibodies as in Example 2. FIGS. 1e and h show the results for the most active whole AHC forks in comparison with their component monospecific antibodies.

While the unconjugated antibodies had little effect on inhibition of cell growth, several of the whole AHC forks, e.g. 317G5-454A12 on HT29 cells and 113F1-454A12 and 454A12-520C9 on SK-Br-3 cells, caused over 50% growth inhibition at fork concentrations of about $10^{-9}M$ to $10^{-7}M$, about 0.4 to 40 µg/ml, assuming an average molecular weight of approximately 400,000 for the whole AHC forks. None of the antibodies or forks significantly affected growth of the negative control HBL100 cells.

Results from additional MTT assays are summarized in Table 3, which also includes data from experiments on the SW948 colorectal and SK-OV-3 ovarian cancer cell lines. Results representing more than 30% inhibition of cell growth are highlighted. The three whole AHC forks mentioned above remained the most consistently active. The 113F1-454A12 fork caused more than 30% growth inhibition in 7 of 7 experiments with SK-BR-3, 2 of 2 experiments with SW948 and 1 of 2 experiments with SK-OV-3. The 317G5-454A12 fork caused more than 30% inhibition in 5 of 6 assays with HT-29 and 2 of 2 assays with SW948, while the 454A12-520C9 fork gave more than 30% inhibition in 6 of 7 tests with SK-Br-3 and 1 of 2 tests with SK-OV-3. Certain other whole AHC forks showed lower or less frequent levels of activity against the SK-BR-3 cell line, e.g., 2G3-113F1, 2G3-454A12, 113F1-260F9, 113F1-317G5, 113F1-520C9, 260F9-454A12 and 317G5-520C9.

TABLE 3

Growth of Cell Lines in the Presence of Antigen Forks

| Cell Line | Assay # | Days | nM Fork | G1 | G2 | G3 | G4 | G5 | 12 | 13 | 14 | 15 | 23 | 24 | 25 | 34 | 35 | 45 |
|---|---|---|---|---|---|---|---|---|---|---|---|---|---|---|---|---|---|---|
| HBL-100 | F3 | 3 | 50 | | | | 100 | | | | 88 | | | 87 | | 98 | | 94 |
| | F4 | 3 | 50 | 102 | 126 | 99 | 82 | 88 | | | 87 | | | 75 | | 91 | | 99 |
| | F5 | 5 | 50 | 98 | 103 | 100 | 103 | 101 | 100 | 99 | 93 | 103 | 98 | 98 | 103 | | | |
| | F6 | 3 | 50 | 105 | 107 | 109 | 111 | 95 | 98 | 104 | 87 | 97 | | 110 | | 92 | | 94 |
| | F7 | 6 | 50 | 92 | 106 | 98 | 104 | 95 | 111 | 101 | 93 | 101 | | 101 | | 103 | | 112 |
| | F8a | 6 | 50 | 82 | | | 91 | 94 | 97 | 99 | 89 | 99 | 97 | 106 | 108 | 100 | 99 | 95 |
| | F8b | 6 | 50 | | | | | | 99 | 95 | | 96 | | | | | | |
| SK-BR-3 | F1 | 3 | 62.5 | | | | 997 | | | | <u>66</u> | | | 81 | | 87 | | 68 |
| | F2 | 3.75 | 50 | | | | 99 | | | | <u>68</u> | | | 96 | | 101 | | <u>78</u> |
| | F3 | 3 | 50 | | | | 93 | | | | <u>57</u> | | | 92 | | 116 | | <u>65</u> |
| | F4 | 3 | 50 | 88 | 93 | 105 | 100 | 99 | 94 | 75 | <u>46</u> | 77 | | 86 | | 94 | | <u>58</u> |
| | F5 | 5 | 50 | 77 | 101 | 100 | 94 | 96 | 94 | 75 | <u>46</u> | 77 | | 86 | | 94 | | <u>58</u> |
| | F6 | 3 | 50 | <u>67</u> | 107 | 103 | 108 | 103 | 76 | 82 | <u>62</u> | 82 | | 103 | | 93 | | <u>65</u> |
| | F7 | 6 | 50 | <u>62</u> | 100 | 99 | <u>65</u> | 74 | 74 | 76 | <u>25</u> | 73 | | <u>64</u> | | 80 | | <u>31</u> |
| | F8a | 6 | 50 | <u>64</u> | | | 76 | 84 | 72 | <u>67</u> | <u>25</u> | <u>55</u> | 82 | <u>63</u> | 70 | 82 | <u>64</u> | <u>40</u> |
| | F8b | 6 | 50 | | | | | | 98 | 104 | <u>66</u> | | | | | | | |
| SK-OV-3 | F9 | 6 | 25 | 99 | 100 | 99 | 78 | 84 | 89 | 98 | <u>68</u> | 97 | 90 | 81 | 99 | 81 | 89 | <u>66</u> |
| | F10 | 6 | 50 | | | | 95 | | | | 85 | | | 89 | | 103 | | 85 |
| HT-29 | F3 | 3 | 50 | | | | 102 | | | | 92 | | | 101 | | <u>66</u> | | 100 |
| | F4 | 3 | 50 | 105 | 111 | 105 | 103 | 101 | | | 72 | | | 95 | | <u>64</u> | | 92 |
| | F5 | 5 | 50 | 97 | 107 | 113 | 101 | 95 | 105 | 100 | 84 | 106 | | 93 | | <u>48</u> | | 104 |
| | F6 | 3 | 50 | 101 | 103 | 94 | 102 | 104 | 100 | 97 | 89 | 102 | | 100 | | 81 | | 87 |
| | F7 | 6 | 50 | 94 | 99 | 103 | 110 | 107 | 106 | 91 | 91 | 105 | | 100 | | <u>57</u> | | 106 |
| | F8a | 6 | 50 | 103 | | | 103 | 96 | 98 | 109 | 102 | 103 | 106 | 014 | 114 | <u>52</u> | 114 | 110 |
| | F8b | 6 | 50 | | | | | | 106 | 104 | | 102 | | | | | | |

TABLE 3-continued

Growth of Cell Lines in the Presence of Antigen Forks

| Cell Line | Assay # | Days | nM Fork | G1 | G2 | G3 | G4 | G5 | 12 | 13 | 14 | 15 | 23 | 24 | 25 | 34 | 35 | 45 |
|---|---|---|---|---|---|---|---|---|---|---|---|---|---|---|---|---|---|---|
| SW948 | P9 | 6 | 25 | 103 | 101 | 96 | 107 | 109 | 107 | 102 | 54 | 106 | 96 | 104 | 102 | 40 | 102 | 101 |
|  | P10 | 6 | 25 |  |  |  |  |  |  |  | 36 |  |  |  |  | 43 |  |  |

Results are shown as percent of control growth in the absecne of any fork or antibody treatment. Fork names are abbreviated as two letter codes in which G stands for 2G3, 1 for 113F1, 2 for 260P9, 3 for 317G5, 4 for 454A12 and 5 for 520C9; e.g., "34" stands for 317G5-454A12 fork.

EXAMPLE 5

Cytotoxicity of 317G5-454A12 Fork in Combination with Deferoxamine

Whole AHC antigen fork 317G5-454A12 was selected to study its effect on the growth of various target cancer cells when administered in conjunction with deferoxamine (DFO). The study was conducted using the assay described in Example 4 with the following difference: 25 µl of fork and 25 µl of deferoxamine at appropriate dilution were added to each well.

Figure 2B:
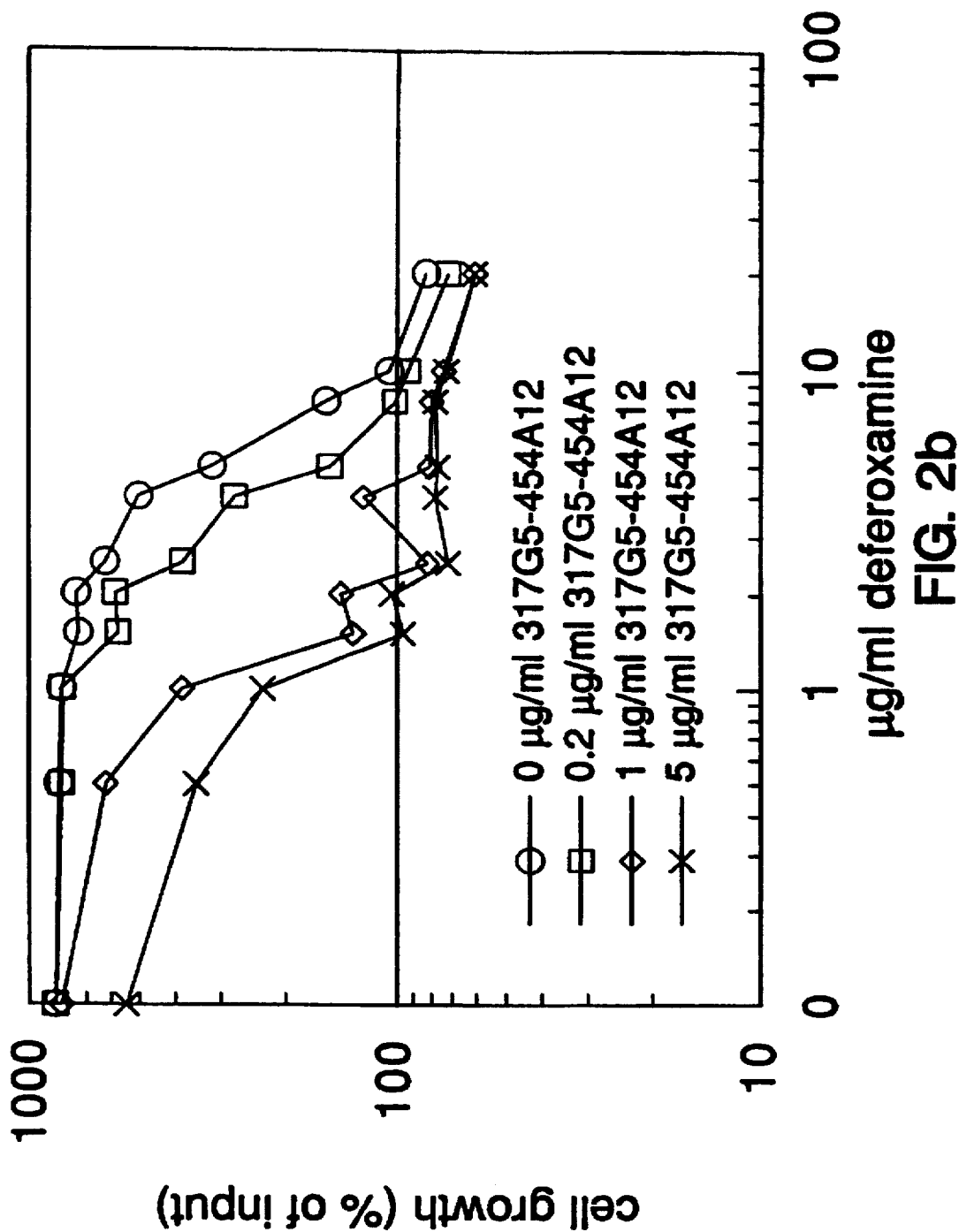
Figure 3:
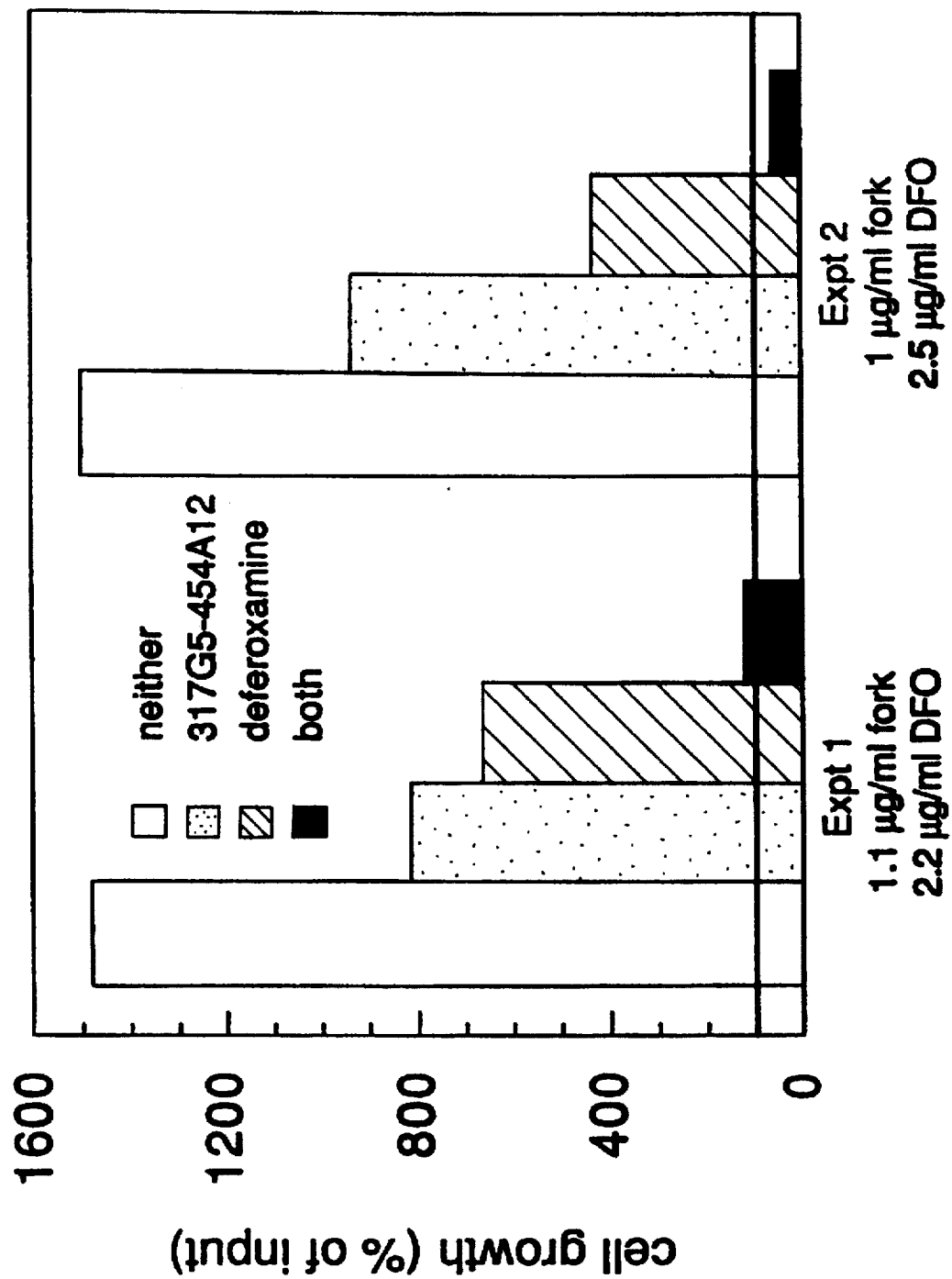
FIG. 3 shows the growth inhibitory effects of antigen fork 317G5-454A12 and deferoxamine, alone and together, on human colorectal cancer cell line HT29.

FIGS. 2a and 2b show the effects of various concentrations of the 317G5-454A12 whole AHC fork and deferoxamine on the growth of human colorectal cancer cell line SW948. Presence of the fork at 1 or 5 µg/ml caused a five-fold reduction in the amount of DFO needed to produce a given inhibitory effect. Conversely, DFO at 1.5 µg/ml or higher caused a ten-fold or greater reduction in the amount of fork necessary for a given inhibitory effect. FIG. 3 shows similar results for human colorectal cancer cell line HT29, and also shows in experiment 2 that the combined effect of DFO and antibody was cytotoxic rather than cytostatic, since the day 6 cell count was less than the input cell count.

Figure 4:
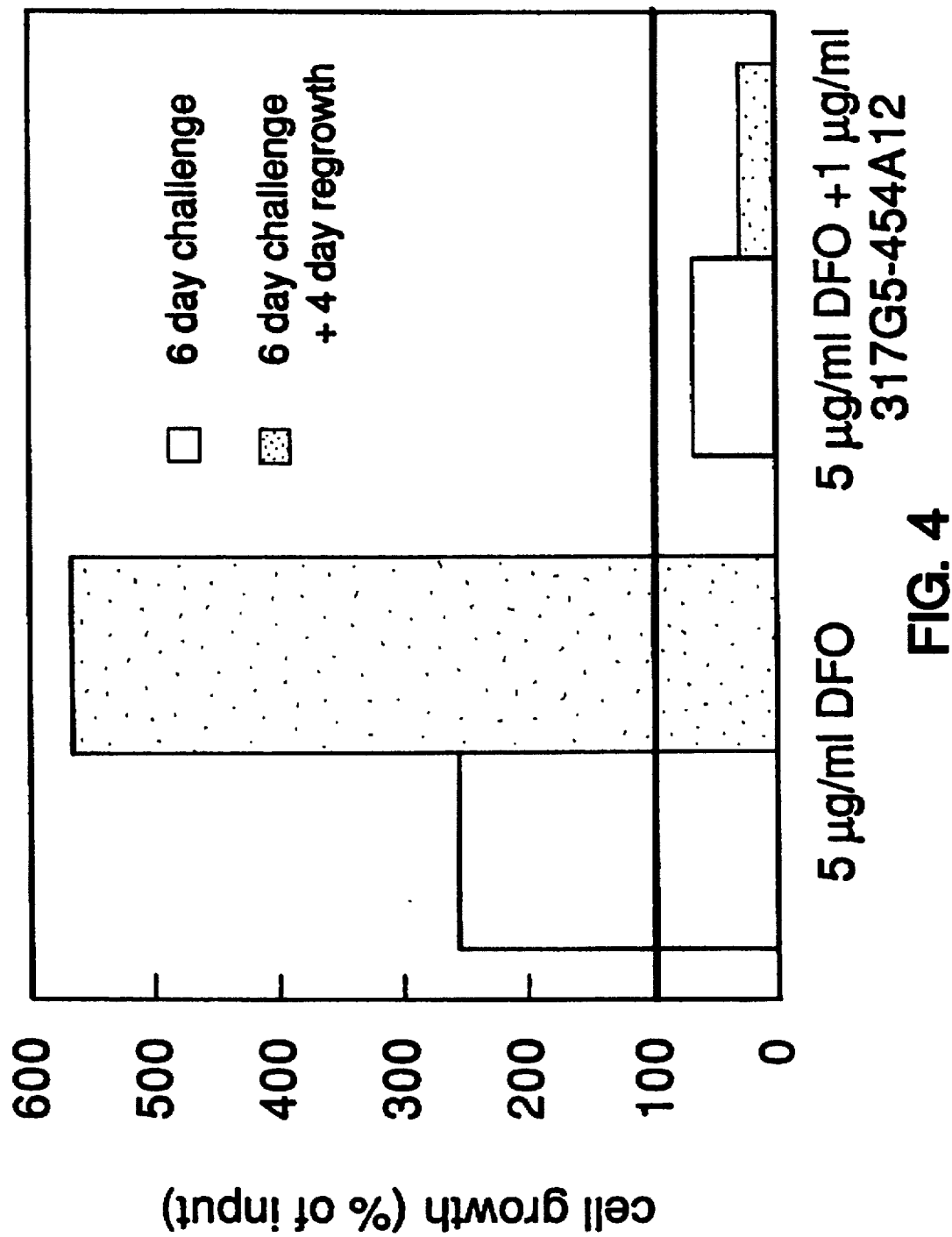
FIG. 4 shows the capability of SW948 colorectal cancer cells for regrowth after treatment with 5 μg/ml deferoxamine, or after treatment with 5 μg/ml deferoxamine and 1 μg/ml of antigen fork 317G5-454A12.

To check on cell viability, assays similar to the above were run in duplicate, and after 6 days, the second plate was aspirated, 150 µl fresh growth medium was added to the wells, and the plate was incubated in the absence of DFO and whole AHC fork for 4 more days. FIG. 4 demonstrates that viable cells were still present after 6 days in 5 µg/ml DFO, as evidenced by significant regrowth after 4 days. In contrast, there was no regrowth, and in fact cell counts continued to fall 4 days after treatment with 5 µg/ml DFO plus 1 µg/ml fork. This indicates that the combination of antigen fork plus deferoxamine was cytotoxic, and led to killing of the targeted tumor cells.

EXAMPLE 6

Cytotoxicity of 317G5 Fab'-454A12 Fab' MAFHD

The monovalent antigen fork heterodimer (MAFHD) version of the 317G5-454A12 whole AHC fork was created by chemical linkage of antibody Fab' fragments, as described in Example 3 above. Hereinafter, the whole AHC fork 317G5-454A12 will be referred to as the "34 fork" and the 317G5 Fab'-454A12 Fab' MAFHD will be referred to as the "3'4' fork".

Figure 5A:
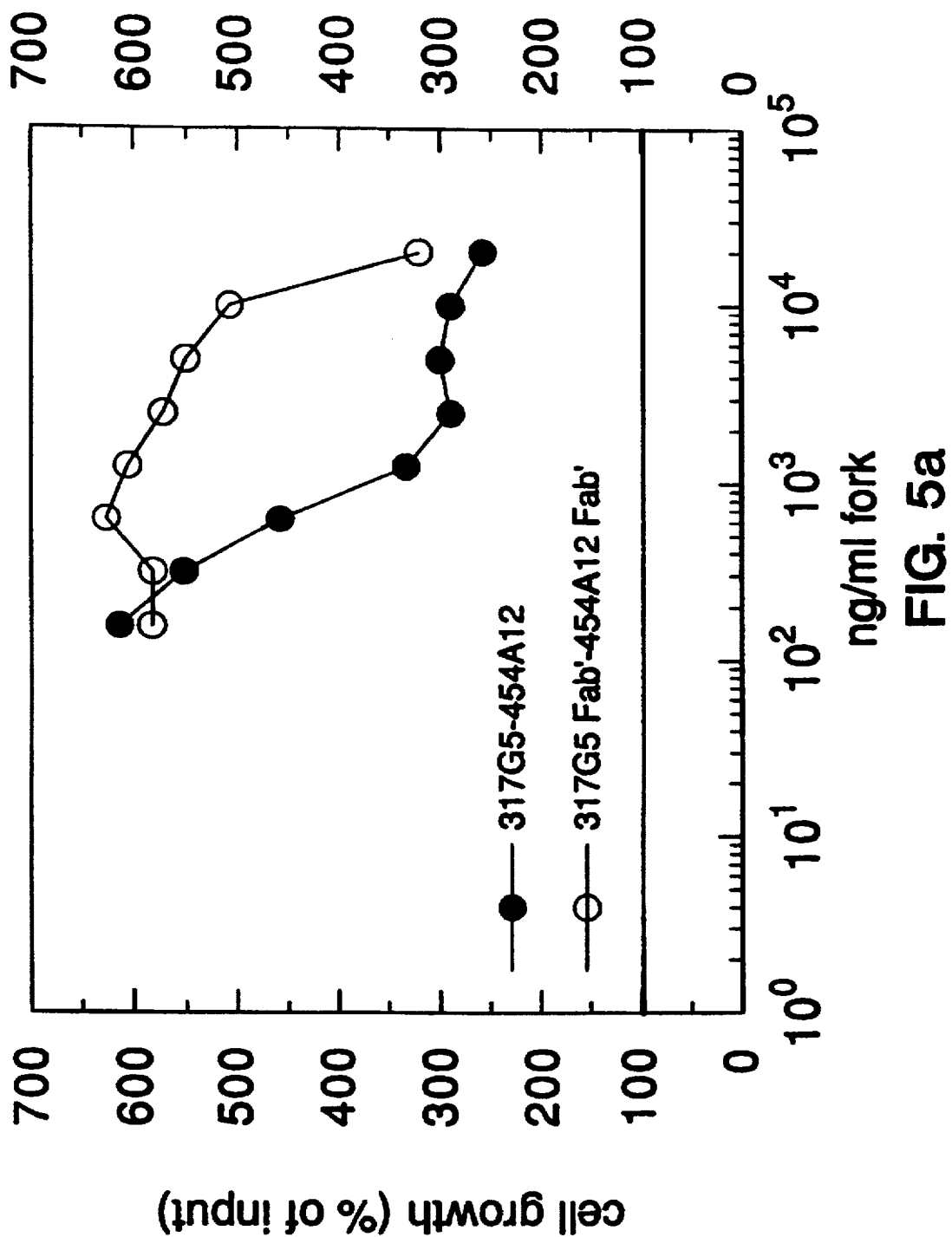
FIGS. 5a and 5b compare the growth inhibitory effect of the chemically relinked bispecific F(ab')2 fragment 317G5 Fab'-454A12 Fab' to that of 317G5-454A12 whole antibody heteroconjugate forks on SW948 cells alone (FIG. 5a) or with deferoxamine (FIG. 5b).
Figure 5B:
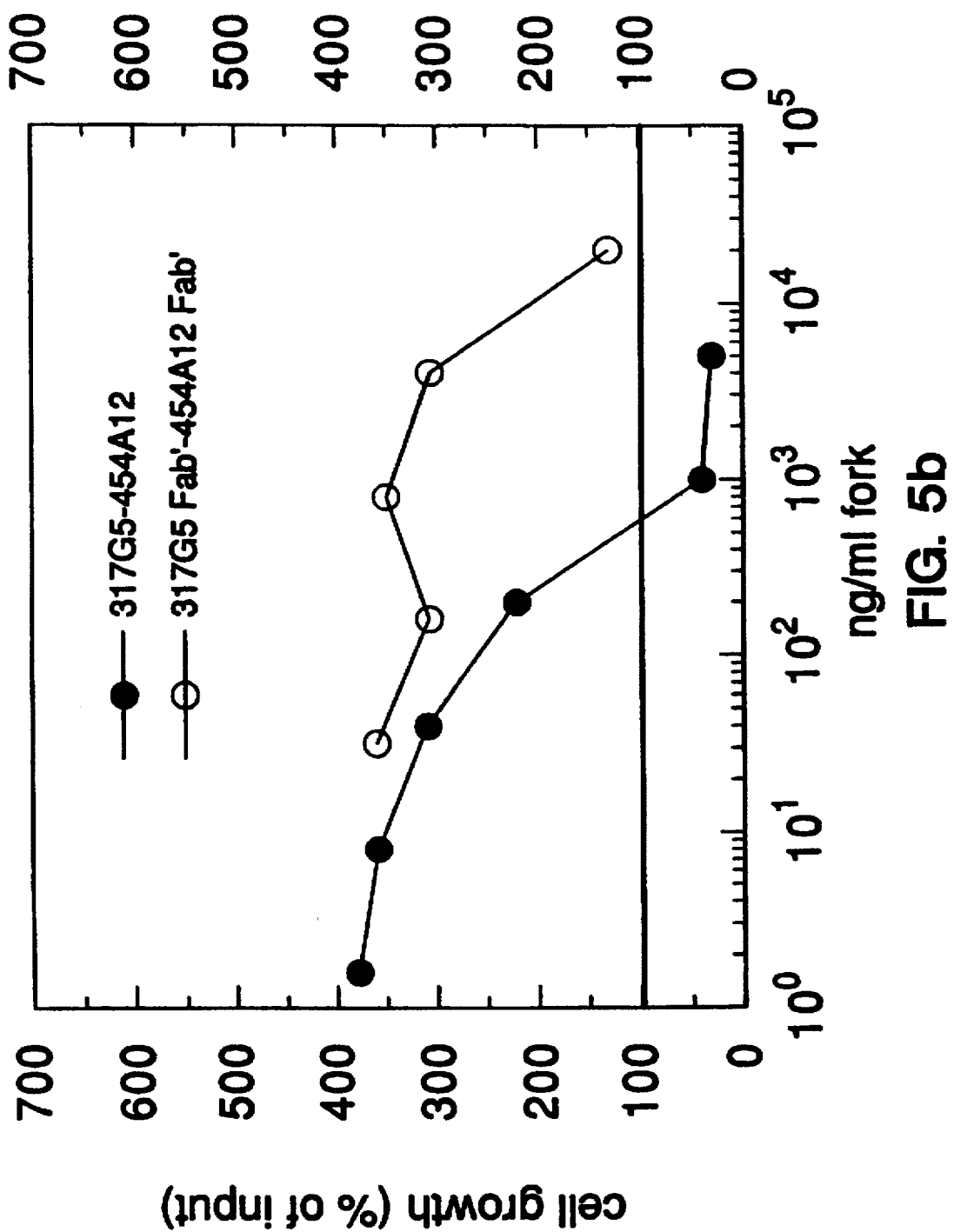

The 34 and 3'4' forks were tested for growth inhibitory effects on SW948 and HT29 colorectal cancer cells using MTT assays similar to those described in Examples 4 and 5. FIG. 5a shows that both the 34 and 3'4' forks inhibited growth of SW948 cells, although the whole antibody fork worked at about a 20 fold lower concentration than the monovalent fork. FIG. 5b shows that either fork in combination with deferoxamine inhibited the growth of SW948 cells, although the monovalent 3'4' fork required about a 50 fold higher concentration to produce the same inhibitory effect.

These experiments provide important indications that monovalent antigen forks can inhibit cell growth. It is suspected that the 3'4' fork preparation was relatively impure; furthermore, since the components of the 3'4' fork were monovalent, there is a greater chance for them to have been inactivated during crosslinking. Thus, the lower observed potency of the monovalent 3'4' fork preparation may represent a real effect resulting from decreased valency of each antibody binding site in the fork construct, or instead may be only an apparent effect caused by a nonhomogeneous, partially active preparation.

Figure 7A:
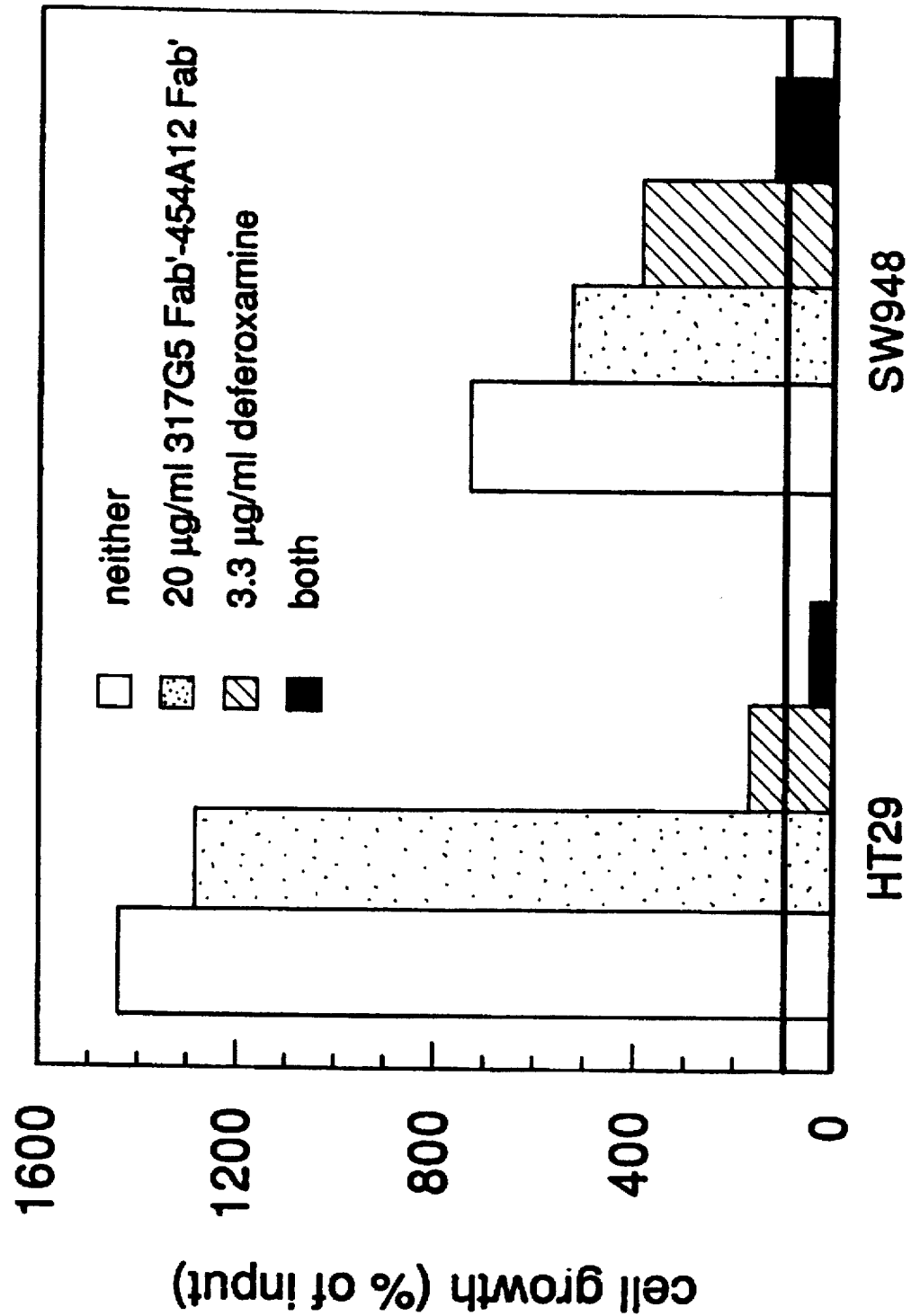

FIG. 6 shows that the combination of the monovalent 3'4' fork and deferoxamine was cytotoxic to both the HT29 and the SW948 colorectal cancer cell lines. FIGS. 7a and 7b compare the effects of monovalent 3'4' fork and deferoxamine, alone or combined, on the same two cell lines. The combination of antigen fork plus drug was cytotoxic in 3 of 4 cases and strongly cytostatic in the other case. The results presented in this example indicate that monovalent forks may be useful agents for suppressing tumor cell growth and suggest the investigation of biologically produced or genetically engineered monovalent forks. (See Examples 10–12).

EXAMPLE 7

Inhibition of SW948 Cells by 113F1-454A12 Whole AHC Fork and DFO

Figure 8:
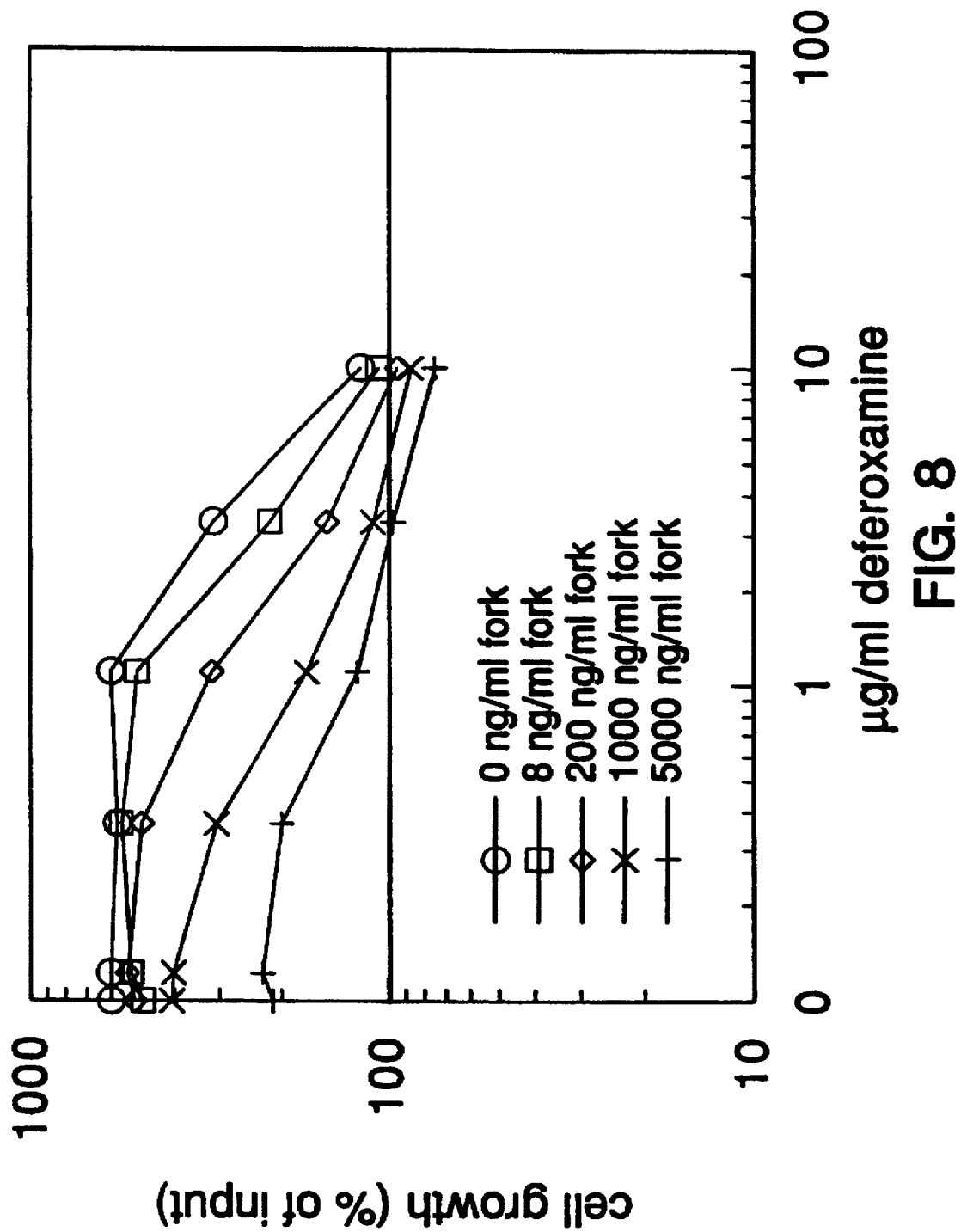
FIGS. 8 and 9 show the effects of whole AHC fork 113F1-454A12 plus deferoxamine on SW948 cells.
Figure 9:
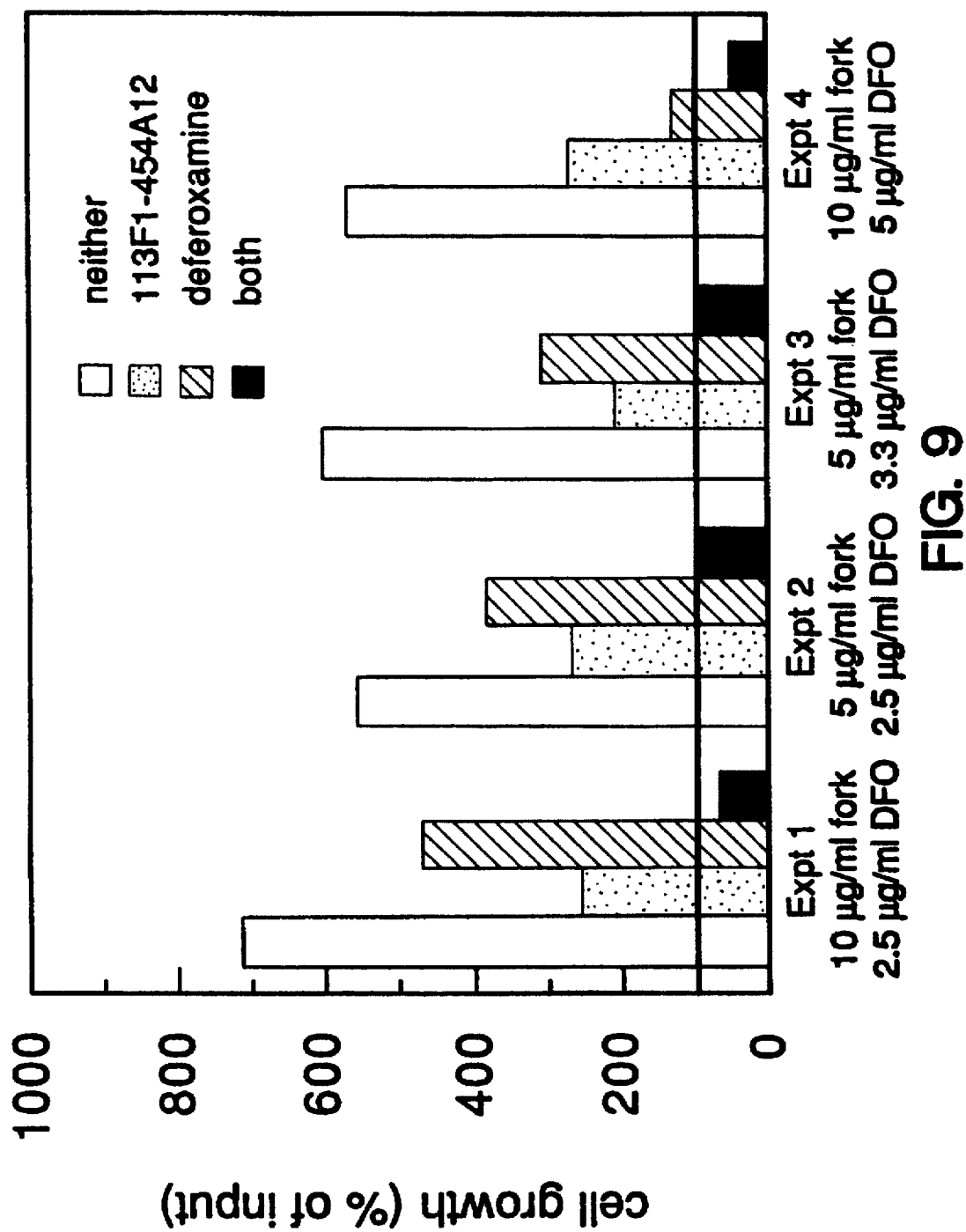

The 113F1-454A12 whole AHC fork that was found to be active in Example 4 (see FIGS. 1g and 1h) was further tested in MTT assays in combination with deferoxamine. FIG. 8 shows that 1 or 5 µg/ml of 113F1-454A12 whole AHC fork substantially reduced the dose of deferoxamine required for a given growth inhibitory effect on SW948 colerectal cancer cells. Cytotoxic effects were observed with 1 or 5 µg/ml of fork plus 10 µg/ml deferoxamine. FIG. 9 shows combination experiments for 113F1-454A12 fork and deferoxamine on SW948 cells; the combination was cytotoxic in two cases and either cytotoxic or cytostatic in two other cases.

EXAMPLE 8

Inhibition of MDR Cell Line Growth by 15D3-454A12 Whole AHC Fork and DFO

Figure 10:
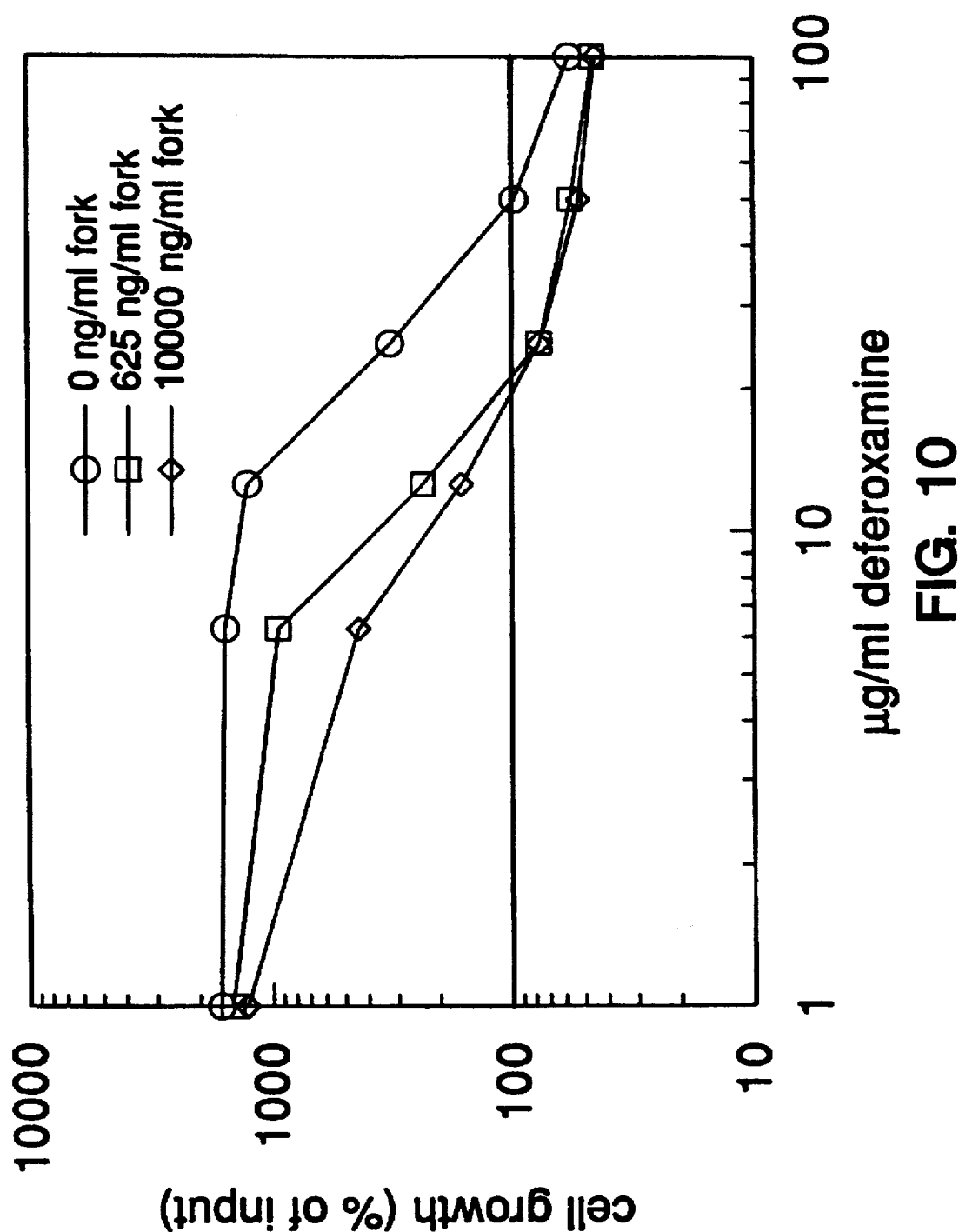
FIG. 10 shows the growth inhibitory effects of whole AHC fork 15D3-454A12 toward adriamycin-resistant erythroleukemia cell line K562-R7, with or without deferoxamine.
Figure 11:
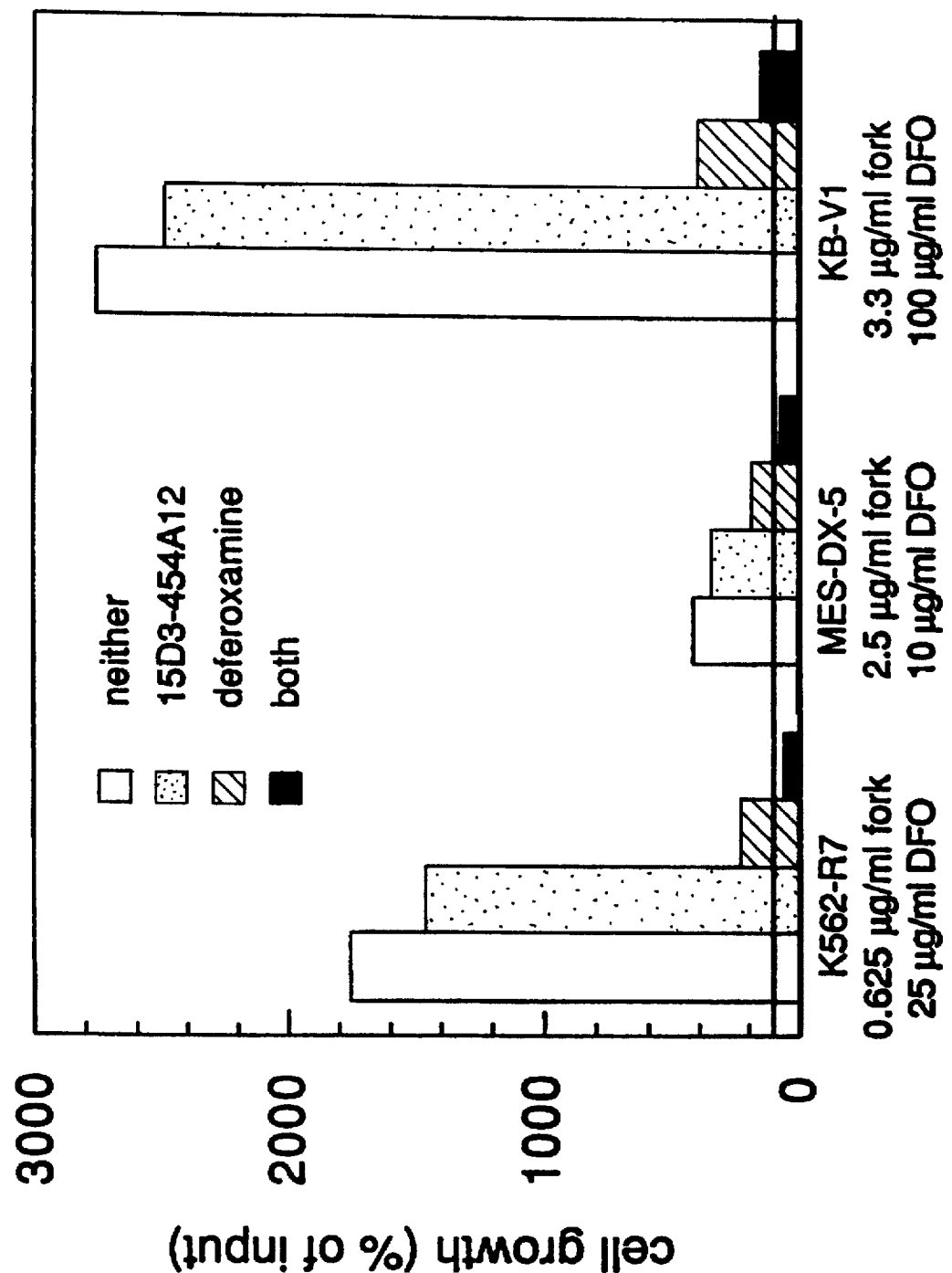
FIG. 11 compares the growth inhibitory effects of whole AHC fork 15D3-454A12, with or without deferoxamine, on three multiple-drug-resistant cell lines: K562-R7, sarcoma cell line MES-DX-5, and squamous carcinoma cell line KB-V1.

The 15D3-454A12 fork recognizes P-glycoprotein, an antigen over-expressed on multidrug resistant (MDR) tumor cells, and human transferrin receptor. This whole AHC fork inhibits the growth of MDR cells. FIG. 10 shows that 0.625 or 10 µg/ml of 15D3-454A12 whole AHC fork reduced by about two fold the dose of deferoxamine required for a given growth inhibitory effect on K562-R7 erythroleukemia cells, which have been selected for amplified P-glycoprotein expression. FIG. 11 compares combinations of 15D3-454A12 fork and deferoxamine on three MDR cell lines; the combination was cytotoxic for K562-R7 erythroleukemia cells and MES-DX-5 sarcoma cells and strongly cytostatic for KB-V1 squamous carcinema cells.

EXAMPLE 9

Inhibition of SK-Br-3 Cells by 454A12-520C9 Fork and Cisplatin

Figure 1G:
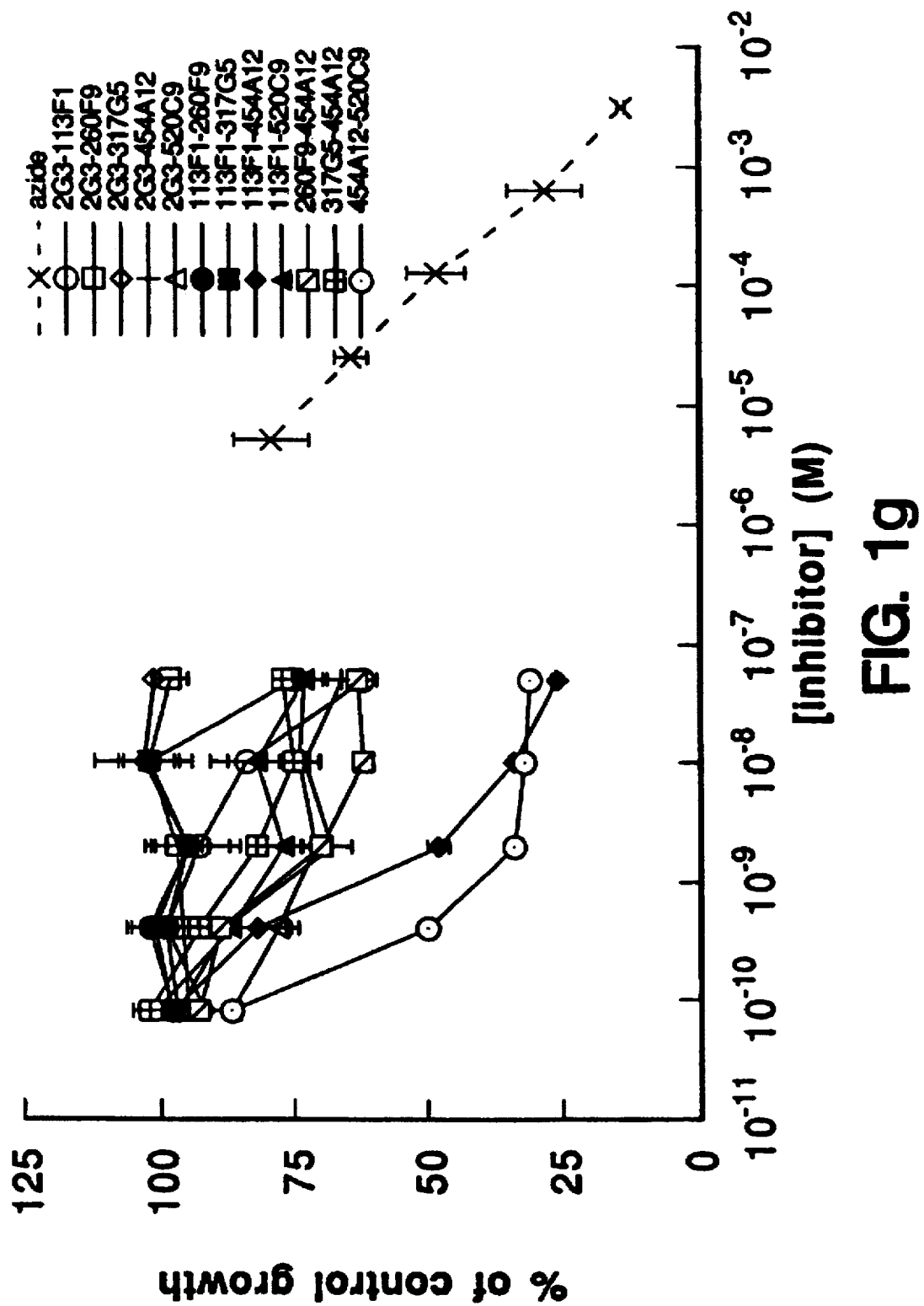
Figure 1H:
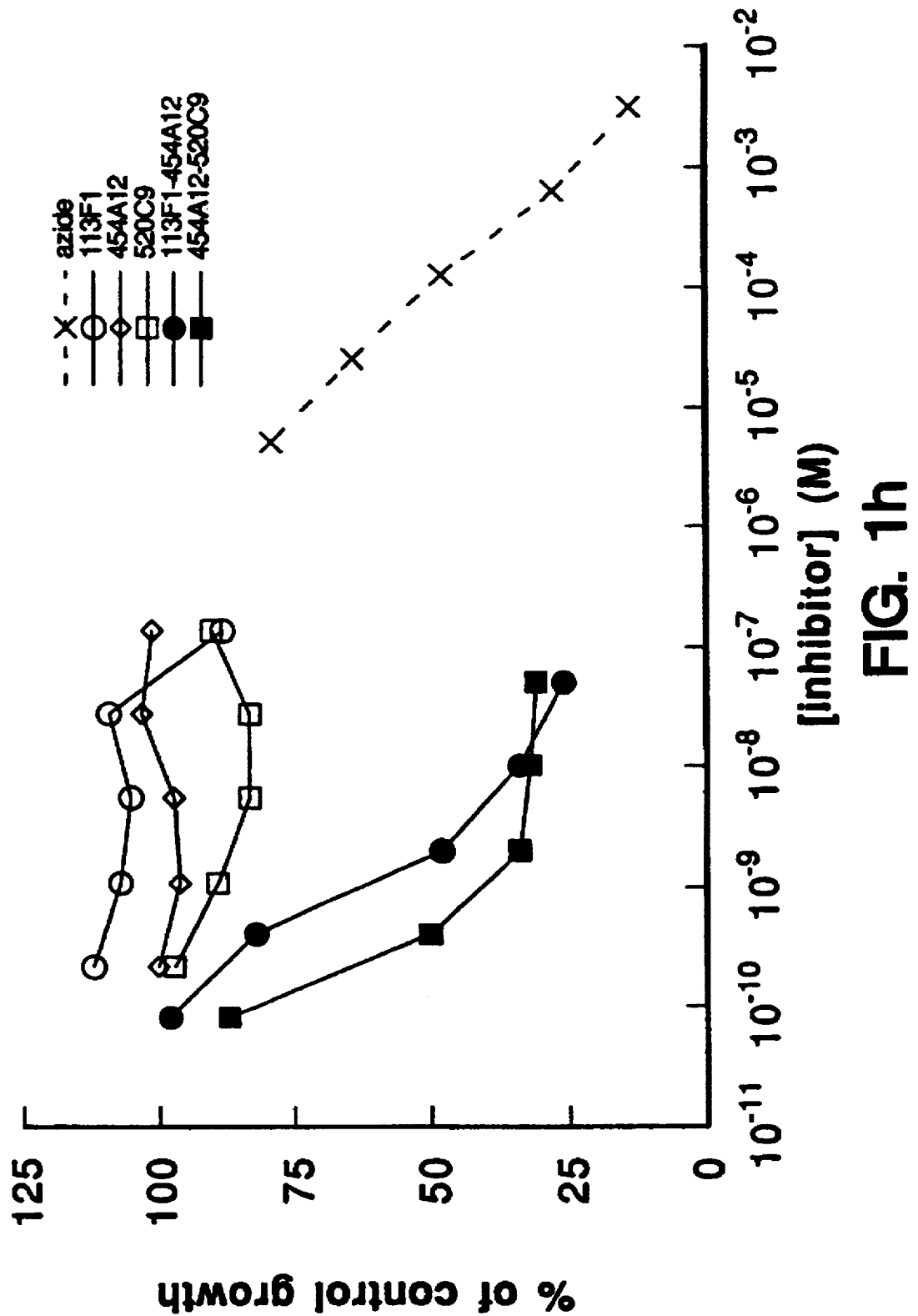
Figure 12:
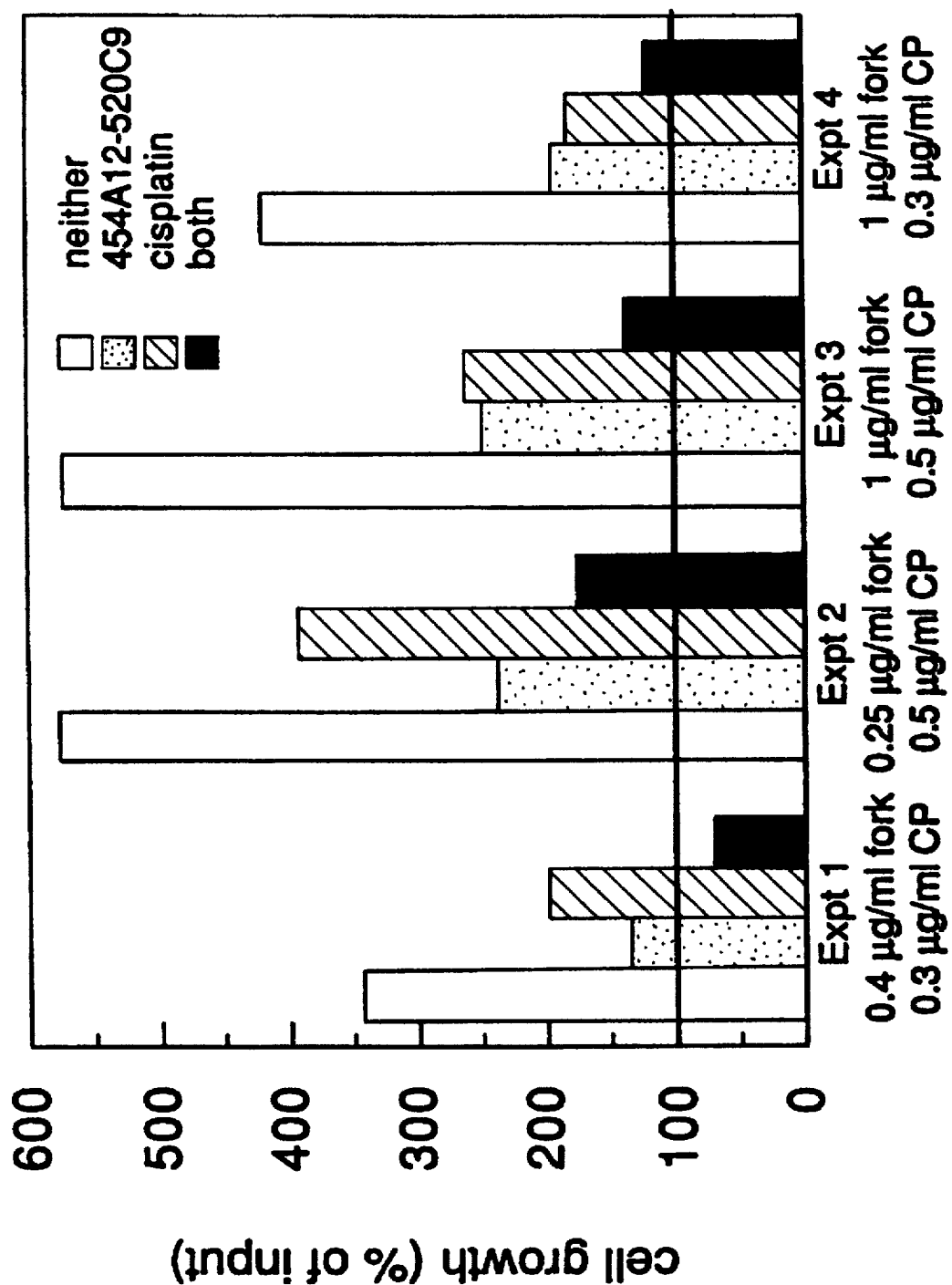
FIG. 12 shows the growth inhibitory effects of 454A12-520C9 bispecific antibody with or without cisplatin on SK-Br-3 cells in four different experiments.

The 454A12-520C9 whole AHC fork that was found to be active in FIGS. 1g and 1h of Example 4 was further tested in MTT assays in combination with cisplatin. FIG. 12 shows combination experiments for 454A12-520C9 fork and cisplatin on SK-Br-3 cells; the combination was cytotoxic in one case and strongly cytostatic in three other cases.

EXAMPLE 10

Production of Hybrid Hybridomas that Secrete Antigen Forks

A. Preparation of hybridoma cells

Hybrid hybridomas that produce the antigen forks of the present invention can be produced in the following exemplified manner. Four days prior to fusion, 34F2 and 454A12 hybridoma cells were each split 1:50 in fresh growth medium (Iscove's modified Dulbecco's medium+2 mM glutamine+OPI+10–15% fetal bovine serum), resulting in a density of about 20,000 cells/ml. All cell culture in this and the following steps was carried out at 37° C. in 5% $CO_2$ incubators. Cells were approximately 90% viable on the day of fusion. Fifty million cells of each hybridoma were spun down in a desktop centrifuge and resuspended in 10 mls growth medium containing labeling agent. 34F2 hybridoma cells were labeled for 20 min at room temperature in 4 µg/ml hydroethidine (Molecular Probes). 454A12 hybridoma cells were labeled for 10 min at 37° C. in 0.4 µg/ml rhodamine 123 and 10µM verapamil (both from Sigma). After labeling, each cell population was rinsed twice with 10 mls HBSS— (Hank's balanced salt solution without calcium or magnesium) containing 10 µM verapamil and resuspended in 10 mls HBSS-+(HBSS without calcium but with magnesium) plus 10 µM verapamil. The labeled cell populations were then mixed 1:1 and centrifuged for 4 min, 200×g at room temperature in a 50 ml polypropylene tube.

B. Fusion

All parts of the fusion procedure were carried out at 37° C. Mixed labeled cells were resuspended in 50 µl HBSS-+ plus 10 µM verapamil. One milliliter of 50% polyethylene glycol (PEG) 1450 (Baker, lot #152514) in HBSS+10 µM verapamil was added slowly over the course of 1 min, allowing PEG to run down the side of the tube and gently mixing the cells using the pipet tip. The cells were gently stirred for another 1 min, and then 2 mls of HBSS-+ containing 5% DMSO and 20 µM verapamil were added with gentle mixing over 2 min. Another 7 mls HBSS-+with 20 µM verapamil were then added, followed by 25 mls growth medium containing 10% FCS, and the cells were incubated 4 hrs at 37° C., standing upright in a 50 ml tube.

C. Cell Sorting and Cloning

All but 4 mls of supernatant was aspirated from above the settled cells, and the cells were then resuspended at about 5 million cells/ml and sorted on an EPICS V cell sorter (Coulter), exciting with a 488 nm argon ion laser. Green (rhodamine 123) fluorescence was analyzed using a 525 nm bandpass filter, and red (ethidium) fluorescence using a 610 nm long pass filter. Approximately 1000 cells with simultaneous high red and green fluorescence were collected and incubated overnight in 5 mls growth medium in a one well of a six well tissue culture plate. On the following day, the cells were plated at approximately 1 cell/well in 96 well flat bottom microtiter plates containing 100 µl/well growth medium and grown for 8 days. Sixty-two of 1056 wells showed growing clones, which were transferred into new wells in a single flat bottom 96 well plate with 200 µl/well fresh growth medium and grown for another 4 days. Clone supernatants were then tested for the ability to compete with binding of probes recognizing the same antigens as the parental antibodies.

D. Probe Blocking Assays

To measure competition for human transferrin receptor binding, 96 well round bottom PVC microtiter plates were coated with 50 µl/well antigen (SK-BR-3 cells lysed at 10 million cells/ml in 20 mM tris, 100 mM NaCl, 0.5% NP-40, stored at −70° C., and diluted for use 1:50 in 50 mM $NaHCO_3$, pH 9.5) and dried overnight in a 37° C. dry incubator. Alternatively, to measure competition for binding to the 42 Kd glycoprotein recognized by antibodies 34F2, 317G5 and 650E2, flat bottom polystyrene 96 well tissue culture plates were seeded with 50,000 SW948 cells/well in 200 µl growth medium+50 µg/ml gentamycin and grown overnight before use.

After rinsing the plates three times with 200 µl/well PBS/1% BSA, clone supernatants were added at 50 µl/well. An additional 50 µl/well of growth medium containing HRP-conjugated antibody probe was then added, and the plates were incubated 60 min at room temperature. 454A12-HRP probe was used at 0.1 µg/ml on SK-BR-3 extract coated plates; 317G5-HRP probe at 4 µg/ml or 650E2 probe at 112g/ml were used on plates of SW948 cells. After incubation, the plates were rinsed four times with 200 µl/well PBS, developed for 15 min with 100 µl/well TMB substrate solution (19 mls of 10 mM sodium acetate, 10 mM sodium EDTA, pH 5.0 plus 1 ml of 2 mg/ml tetramethylbenzidine in ethanol plus 9.1 µl of 3% hydrogen peroxide), quenched with 100 µl/well 0.8M sulfuric acid, and read on a Dynatech plate reader at 450 nm with 630 nm subtraction.

Clones whose supernatants blocked binding of both the 454A12 probe (transferrin receptor target) and the 317G5 or 650E2 probe (42 kilodalton glycoprotein target) were further tested for the ability to block growth of SW948 human colorectal cancer cells in an MTT growth assay.

E. MTT Assay

Five thousand SW948 cells in 100 µl growth medium were seeded in triplicate in 96-well flat-bottom tissue culture plates, and incubated overnight. Serial two-fold dilutions of clone supernatants (⅛ to ¹⁄₉₆ final dilution) or of controls were added to the wells (25 µl volume), followed by 25 µof medium containing deferoxamine so as to achieve final deferoxamine concentrations of 1.25 or 2.5 µg/ml. Plates were incubated for 7 days. An MTT (3-(4,5-dimethylthiazol-2-yl)-2,5-diphenyl tetrazolium bromide) assay kit (CellTiter 96, #G4100, Promega) was used to evaluate the number of viable cells remaining in the wells. 15 µl of dye solution was added per well and the plate was incubated for 4 hrs at 37° C. in 5% $CO_2$ followed by addition of 100 µsolubilization solution. Plates were read for absorbance at 570/630 nm on an ELISA plate reader after all blue crystals had dissolved (typically 1–5 days at room temperature in a moist chamber).

F. Screening of Hybrid Hybridoma Clones

One of 68 clones from 34F2/454A12 fusion TS37 produced supernatants that competed in both probe-blocking assays, and that also inhibited growth of SW948 cells in the MTT assay. Clone 4A3 was subcloned at 0.5 cells/well, and 136/192 or 71% of the resulting subclones were active in both probe blocking assays. Subclone 4A3c2E3 was confirmed to inhibit SW948 growth by MTT assay, and was again subcloned at 0.5 cell/well. Eighty-six out of 95 second stage subclones or 91% showed double probe blocking, and second stage subclone TS37-4A3c2E3c1 A10 was selected based on strong activity in both probe-blocking and SW948 growth inhibition assays.

EXAMPLE 11

Purification of a Hybrid Hybridoma-Derived Bispecific Antigen Fork

A. Preparation of Mouse Ascites Fluid

Hybrid hybridoma cells (fusion TS37, clone 4A3c3E3c1A10) were sent to Harlan BioSciences, Inc. (Indianapolis, Ind.) for ascites production in Balb/c mice. Twenty-five mice were tapped repeatedly, yielding 156 ml of ascites fluid. The ascites fluid was centrifuged 30 min at 50,000×g, separated from the upper lipid layer and pellet, diluted to 450 ml with PBS, and filtered through a Corning 0.22 micron cellulose acetate filter.

B. Affinity Purification 25 ml of diluted, filtered ascites fluid was run through a column containing 5 ml bed volume of Pharmacia Protein G Sepharose 4 Fast Flow. The column was washed with 30 ml PBS and immunoglobulins were eluted with 10 ml 0.5M ammonium acetate, pH 3. The eluate was immediately neutralized with 1M tris base and dialysed to 50 mM sodium acetate, pH 5.5.

C. Cation Exchange Chromatography

Figure 13:
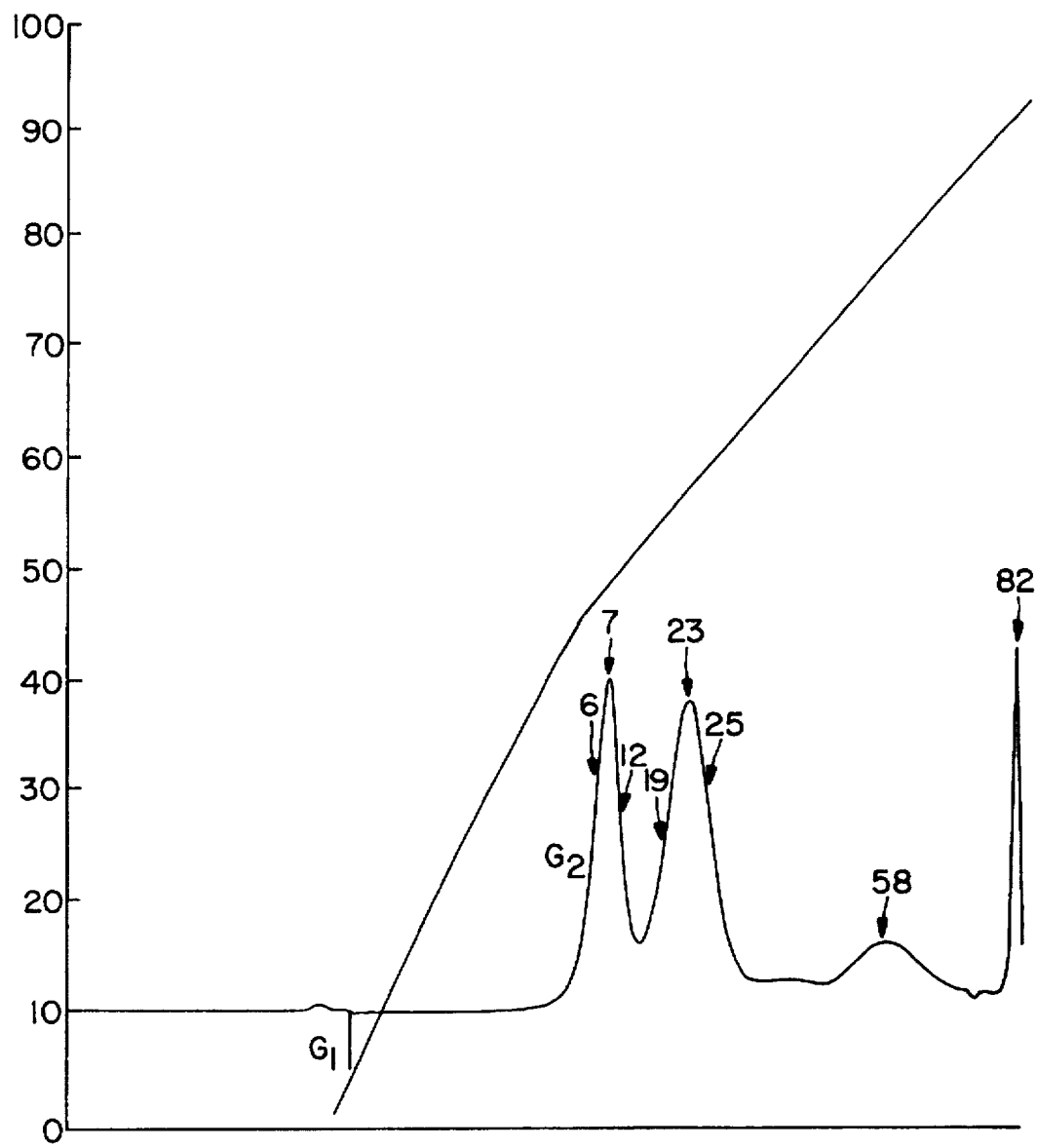
FIG. 13 shows the UV trace of eluted immunoglobulin peaks obtained by S sepharose chromatography of bispecific and parental antibodies produced by hybrid hybridoma clone TS37-4A3c2E3c1A10, derived in fusion TS37 of parental hybridomas 34F2 and 454A12.
Figure 14:
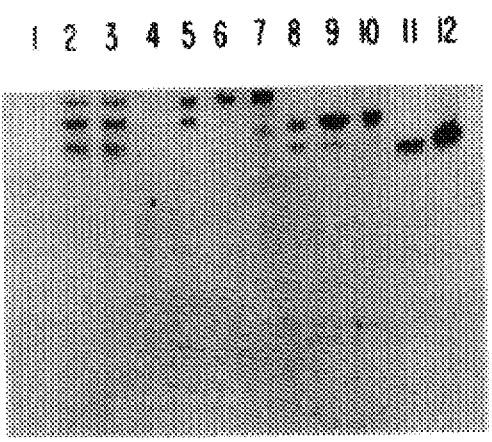
FIG. 14 shows polyacrylamide gel electrophoresis (PAGE) of selected fractions from S sepharose purification of clone TS37-4A3c2E3c1A10, bispecific antibody, concentrated on Amicon Centricon C-30 concentrators and run on a Pharmacia 8–25% acrylamide gradient PhastGel under native conditions.

The dialysate was filtered through a 0.2 micron Acrodisc 13 filter (Gelman Sciences), and a 5 ml aliquot was run at 1 ml/min through a 1×40 cm column containing Pharmacia S Sepharose Fast Flow medium. The column was then washed with 40 ml of 50 mM sodium acetate pH 5.5 (buffer A) at 2 ml/min. Immunoglobulins were eluted with a gradient between buffer A and 20 mM sodium phosphate pH 7.6 (buffer B) at 2 ml/min, as follows: 0–45% buffer B over 45 min, then 45–100% buffer B over 90 min. At 85% buffer B, the second part of the gradient was stopped and 5 ml of 1M sodium phosphate pH 7 was injected to remove any tightly bound protein. FIG. 13 shows the UV trace of eluted immunoglobulin peaks. Selected peak fractions were concentrated on Amicon Centricon C-30 concentrators, and concentrated fractions were analyzed by polyacrylamide gel electrophoresis (PAGE) on a Pharmacia 8–25% acrylamide gradient PhastGel under native conditions (FIG. 14). The first major peak on S Sepharose eluted at the % B expected for parental antibody 34F2 and contained mostly immunoglobulin with a native PAGE mobility of parental antibody 34F2. The third major peak eluted at the % B expected for parental antibody 454A12 and contained almost entirely immunoglobulin with the mobility of parental antibody 454A12. The second major peak eluted at an intermediate % B and contained mostly immunoglobulin with an intermediate mobility, as expected for an antigen fork containing one 34F2 binding site and one 454A12 binding site.

D. MTT Assay

Figure 15:
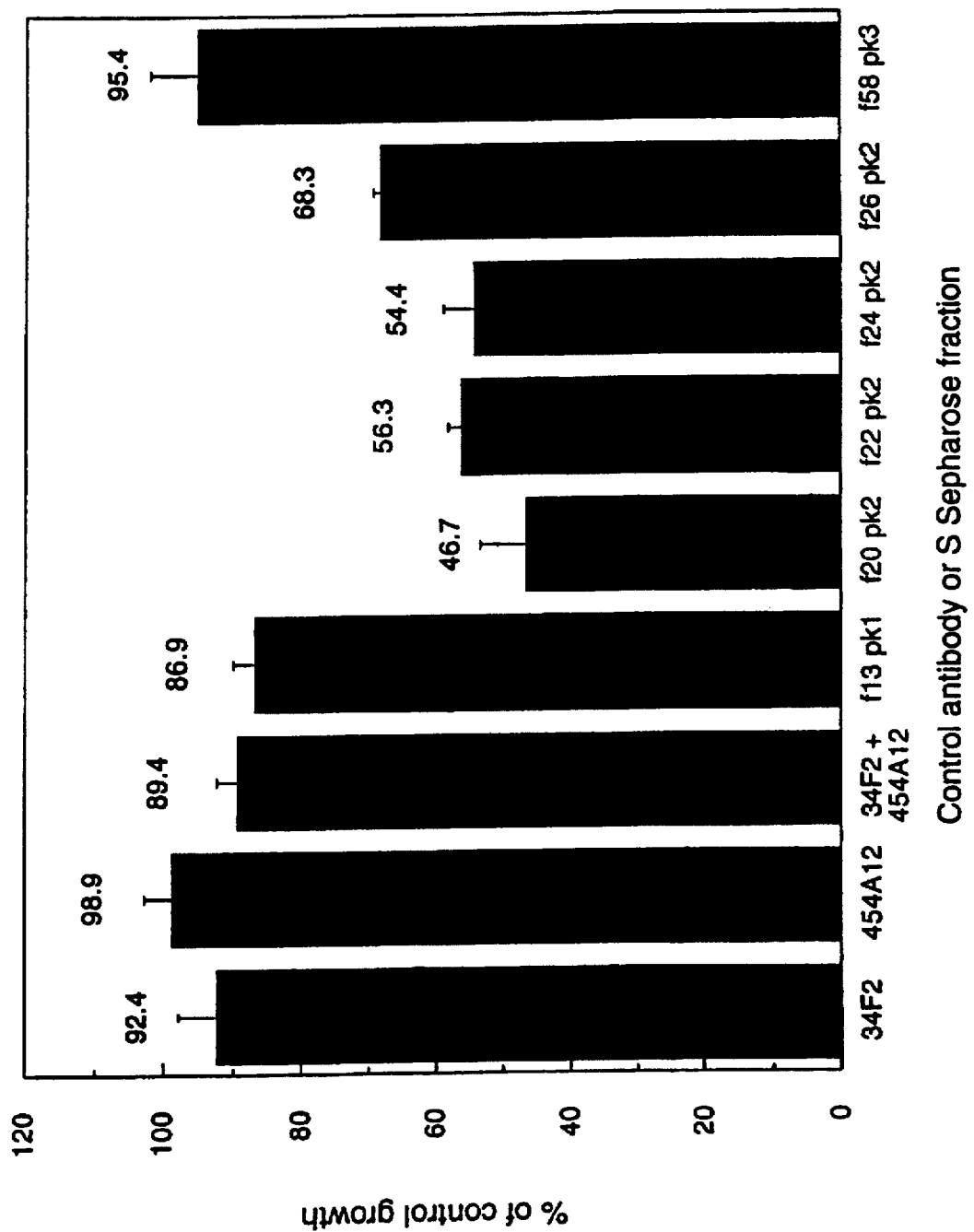
FIG. 15 compares inhibition of SW948 cell growth by selected fractions from the S sepharose purification of clone TS37-4A3c2E3c1A10 bispecific antibody with inhibition by parental antibodies 34F2 and 454A12, alone or combined.
Figure 16A:
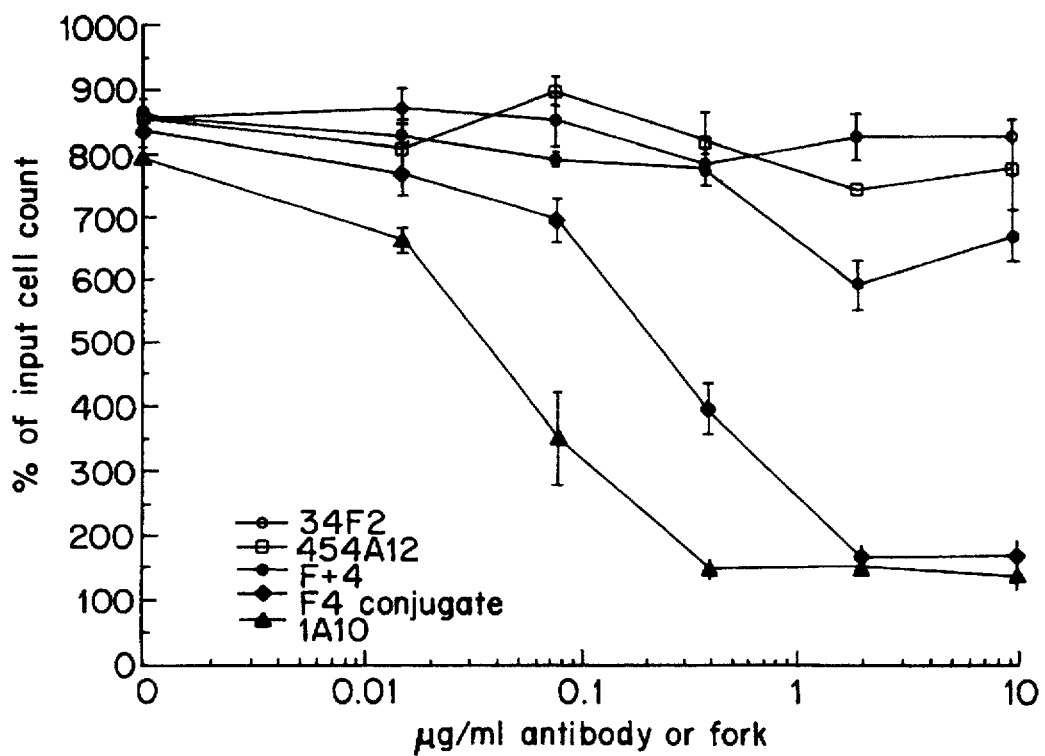
FIG. 16 shows the effects of parental antibodies 34F2 and 454A12, their equimolar combination, their SPDP-linked antigen fork heteroconjugate, and purified 1A10 antigen fork produced by clone TS37-4A3c2E3c1A10 on the growth of four different human cell lines in 1.25 μg/ml deferoxamine.
Figure 16B:
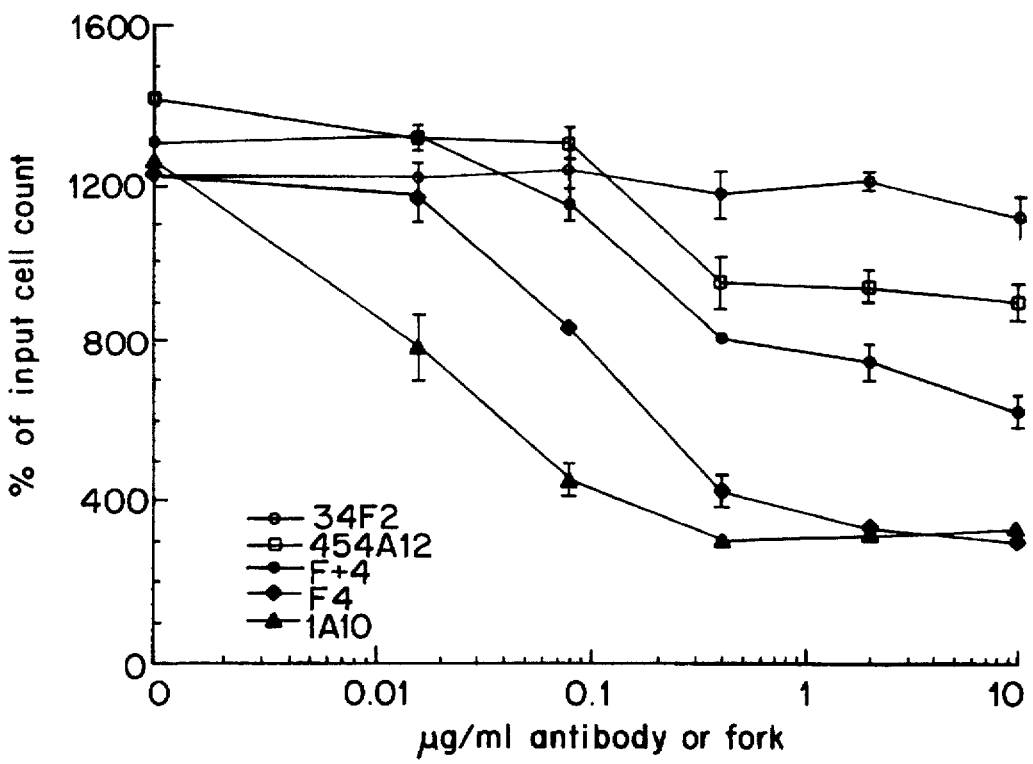
Figure 16C:
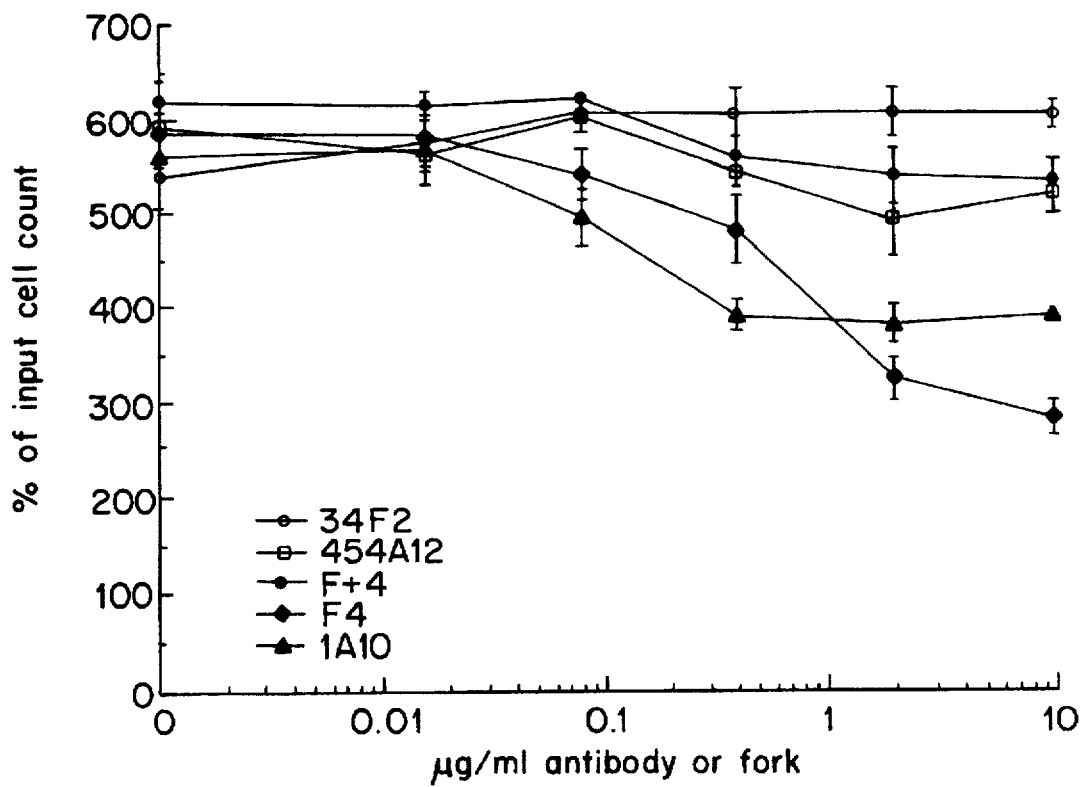
Figure 16D:
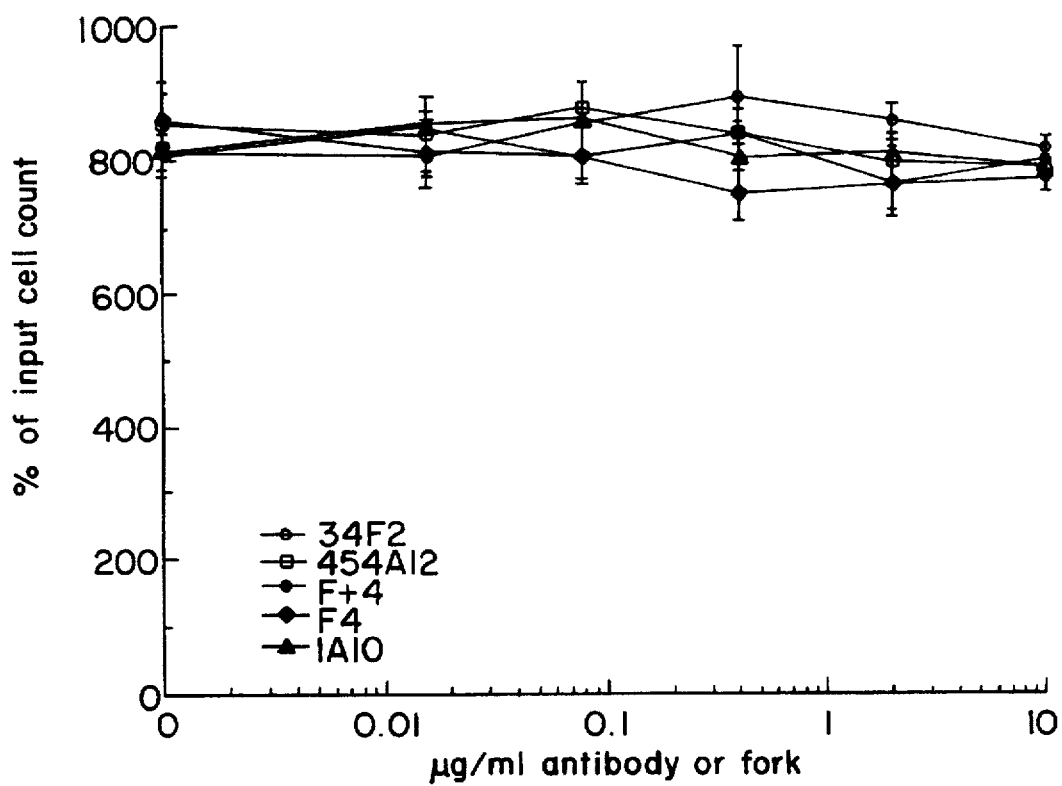
Figure 17A:
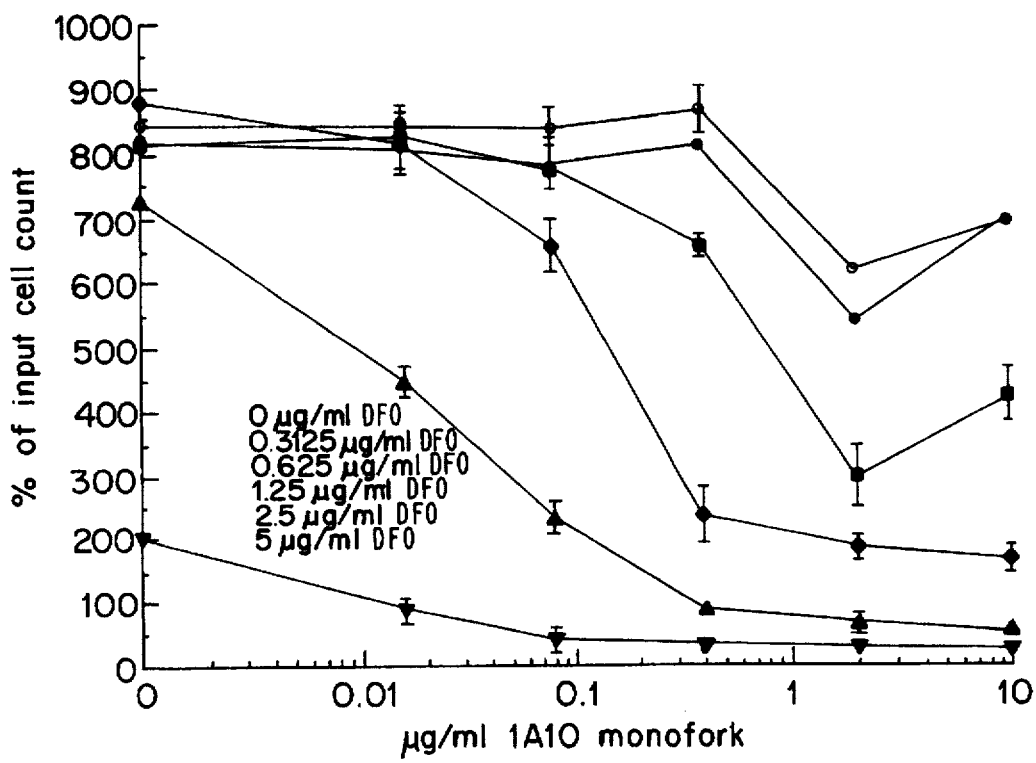
FIG. 17 shows results from testing purified 1A10 antigen fork for synergy with deferoxamine in MTT growth assays with the SW948 and HT29 human colorectal cancer cell lines.
Figure 17B:
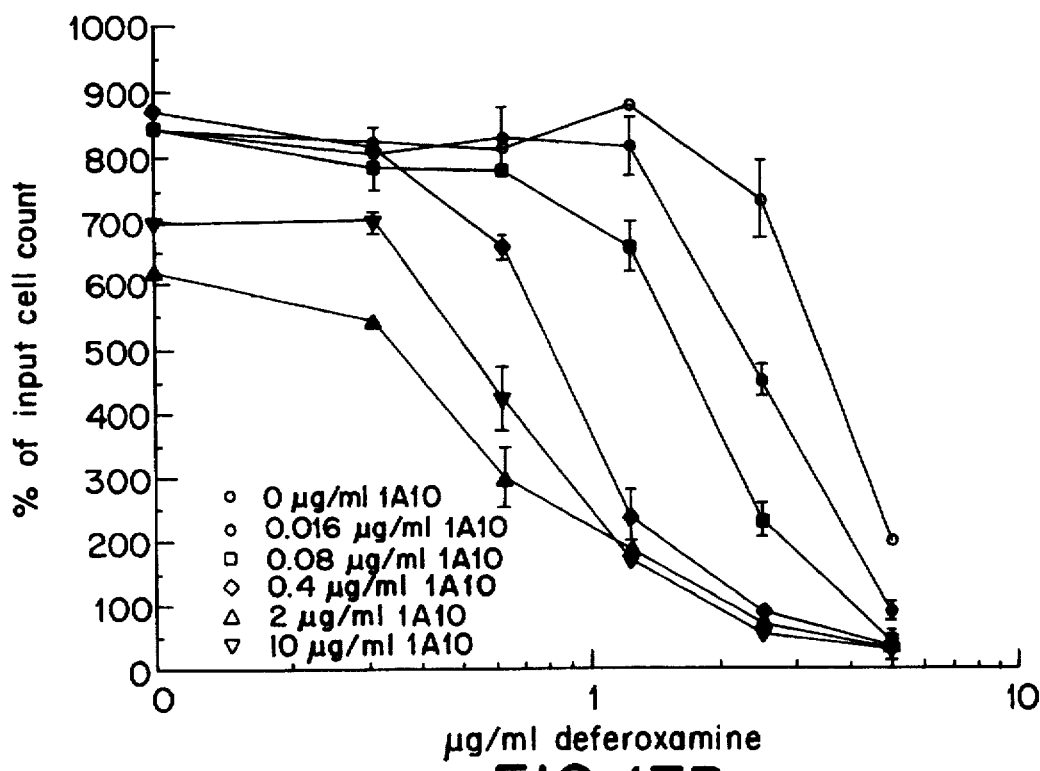
Figure 17C:
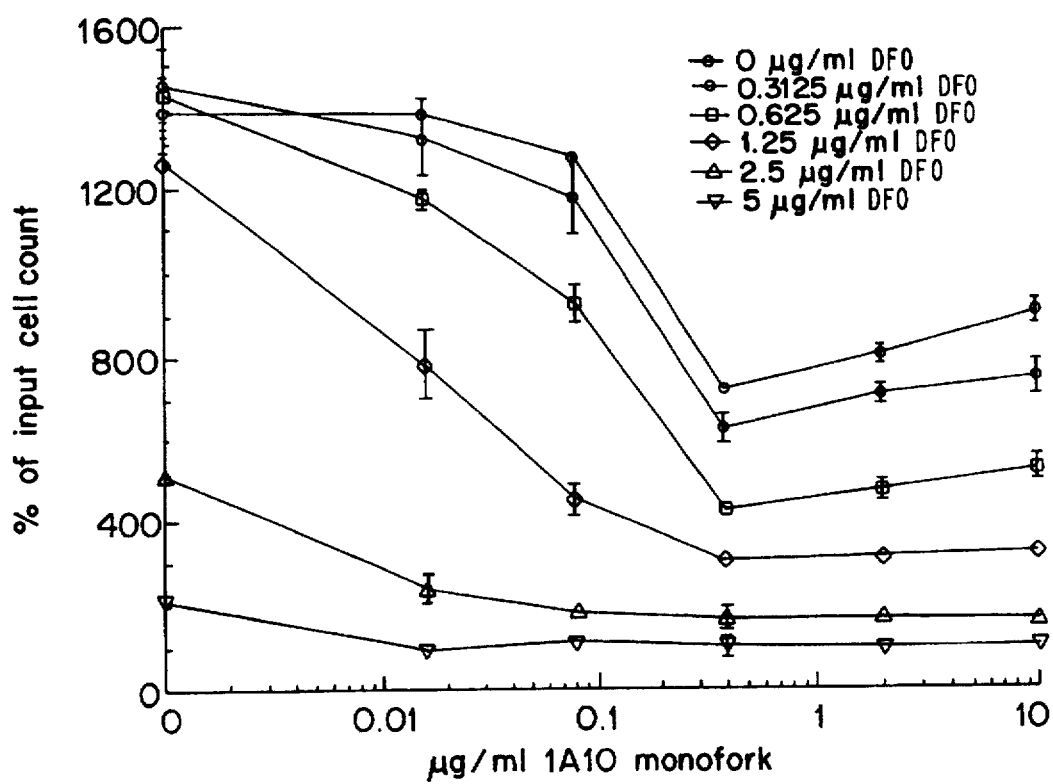
Figure 17D:
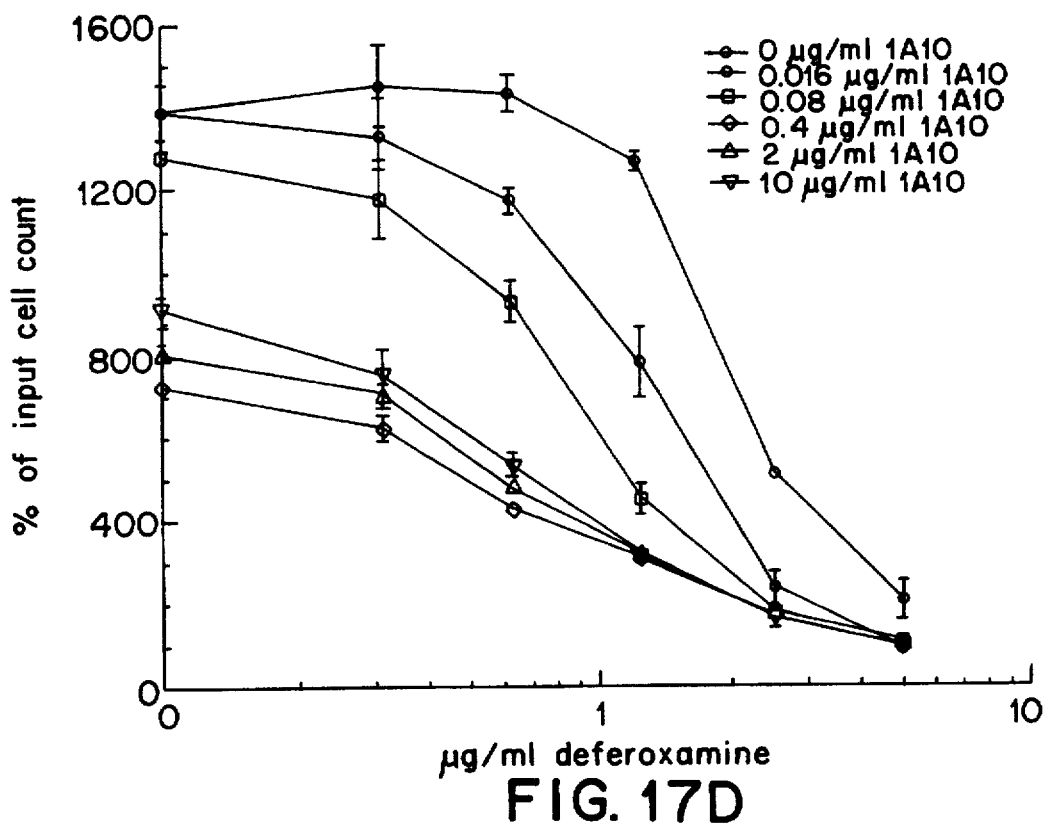

Five thousand SW948 cells in 100 µl growth medium were seeded in triplicate in 96-well flat-bottom tissue culture plates, and incubated overnight. Serial three-fold dilutions of S Sepharose fractions or of control antibodies or SPDP-conjugated antigen fork heteroconjugates were added to the wells in 50 µl volume, and plates were incubated for 7 days. An MTT assay kit was used to evaluate the number of viable cells remaining in the wells, as described in the previous example. FIG. 15 compares inhibition of SW948 cell growth by selected S Sepharose fractions with inhibition by parental antibodies 34F2 and 454A12 alone or combined. The parental antibodies, their combination, and fractions from the first and third S Sepharose peaks did not strongly inhibit growth (1.1% to 13.1% inhibition compared to cell growth in the absence of any antibody). On the other hand, S Sepharose fractions from the second peak caused significantly greater inhibition (31.7% to 53.3%). Since S Sepharose peak 2 elutes between the two parental antibody peaks, contains mostly an immunoglobulin species with the intermediate native PAGE mobility expected for an antigen fork and contains the growth inhibitory activity expected for that antigen fork, it is believed that the major immunoglobulin species in peak 2 represents the desired 34F2-454A12 hybrid hybridoma-derived monovalent bispecific antigen fork which was named 1A10.

EXAMPLE 12

Inhibition of Cancer Cell Growth by Purified 1A10 Monovalent Antigen Fork

A. 1A10 Monovalent Antigen Fork Purification

1A10 monovalent antigen fork was purified from mouse ascites as described in the preceding example. Fractions from the second S Sepharose peak containing antigen fork were pooled and concentrated, yielding a preparation estimated to contain approximately 90% pure antigen fork and approximately 10% parental antibody 454A12.

B. MTT Assays

MTT assays of cell growth were performed as described in the preceding examples. SW948, HT29 and HBL100 cells were seeded at 5000 per well, and SKBR3 cells at 10,000 per well.

C. Cell Growth Inhibition by 1A10 Monovalent Antigen Fork Versus Controls

FIG. 16 shows the effects of parental antibodies 34F2 and 454A12, their equimolar combination, their SPDP-linked antigen fork heteroconjugate, or purified 1A10 monovalent antigen fork on the growth of four different human cell lines in 1.25 µg/ml deferoxamine. For the two colorectal cancer lines (SW948, panel A and HT29, panel B), parental antibody 34F2 caused little growth inhibition at concentrations up to 10 µg/ml. Parental antibody 454A12 and the combination of 34F2 and 454A12 at concentrations of 0.4 to 10 µg/ml caused moderate growth inhibition, but 34F2-454A12 antigen fork heteroconjugate caused stronger inhibition, with half maximal inhibition occurring at approximately 0.2 µg/ml for SW948 cells and 0.1 µg/ml for HT29 cells. For both cell lines, purified 1A10 monovalent antigen fork inhibited growth at lower concentrations than 34F2-454A12 heteroconjugate; half maximal inhibition by 1A10 monovalent antigen fork occurred at approximately 0.06 µg/ml for SW948 and 0.02 µg/ml for HT29.

Both SW948 and HT29 cells are highly sensitive to the effects of antigen forks directed to the 42 kilodalton antigen recognized by 34F2 and 317G5 and to human transferrin receptor recognized by 454A12. It is noteworthy that these cells are more sensitive to 1A10 monovalent antigen fork than to the conjugate of its parental antibodies. Since the conjugate is constructed from bivalent antibodies and contains some antibody trimers and tetramers along with heterodimers, it has a higher valency of each binding site than 1A10 monovalent antigen fork, which has only a single copy of each binding site per molecule. Higher valency tends to confer higher avidity, and conversely, 1A10 monovalent antigen fork might be expected to bind less avidly than 34F2-454A12 conjugate (and therefore might be less active in inhibiting cell growth). The observation that 1A10 monovalent antigen fork inhibits growth more effectively than 34F2-454A12 conjugate suggests that the antigen fork is intrinsically more potent; a possible explanation is that the 42 kd antigen and transferrin receptor binding elements of the 1A10 monovalent antigen fork are held in a more rigid relative conformation than those in an antibody heteroconjugate held together by flexible SPDP linkages. 1A10 binding may cause closer and more sterically-constrained hetero-crosslinking of tumor cell surface antigens, with correspondingly greater effects on their associated functions.

In contrast to SW948 and HT29, the SKBR3 breast cancer cell line (panel C) is considerably less sensitive to growth inhibition by 34F2-454A12 and 317G5-454A12, presumably because it expresses a lower level of 42 kilodalton antigen. At 0.08 and 0.4 μg/ml, 1A10 monovalent antigen fork inhibited the growth of SKBR3 cells more than did 34F2-454A12 conjugate, but at 2 and 10 μg/ml, the reverse was true. The fourth cell line tested, nontumorigenic mammary epithelial line HBL100, lacks significant expression of the 42 kd antigen. As expected, its growth was not significantly inhibited by 1A10 monovalent antigen fork, 34F2-454A12 conjugate or their parental antibodies (panel D).

D. Cell Growth Inhibition by Purified 1A10 Monovalent Antigen Fork and Deferoxamine Since 317G5-454A12 antigen fork heteroconjugate had shown significant synergy with the iron chelating drug deferoxamine in inhibiting tumor cell growth, and since 1A10 monovalent antigen fork recognizes the same pair of tumor antigens, purified 1A10 monovalent antigen fork was tested for synergy with deferoxamine in MTT growth assays (FIG. 17). Panels A and B show results for human colorectal cancer cell line SW948, and panels C and D show results for human colorectal cancer cell line HT29.

Panels A and C show the effect of different levels of deferoxamine on the inhibitory activity of 1A10. For SW948 cells (panel A), increasing the level of deferoxamine from 0.625 to 2.5 μg/ml caused about a two log (100 fold) decrease in the 1A10 concentration needed to cause half maximal cell growth inhibition. For HT29 cells (panel C), increasing the level of deferoxamine from 0.625 to 2.5 μg/ml caused about a one log (10 fold) decrease in the 1A10 concentration needed to cause half maximal cell growth inhibition. Panels B and show the effects of different concentrations of 1A10 antigen fork on the inhibitory activity of deleroxamine. For both cell lines, 2 or 10 μg/ml 1A10 caused a slightly less than ten fold drop in the concentration of deferoxamine needed for a given inhibitory effect.

These results extend previous observations of synergy between deferoxamine and antigen fork heteroconjugates that target the 42 kd and transferrin receptor tumor antigens. 1A10 monovalent antigen fork increases the sensitivity of tumor cells that express both antigens to deferoxamine, and deferoxamine increases their sensitivity to 1A10.

E. Regrowth Experiments

Figure 18A:
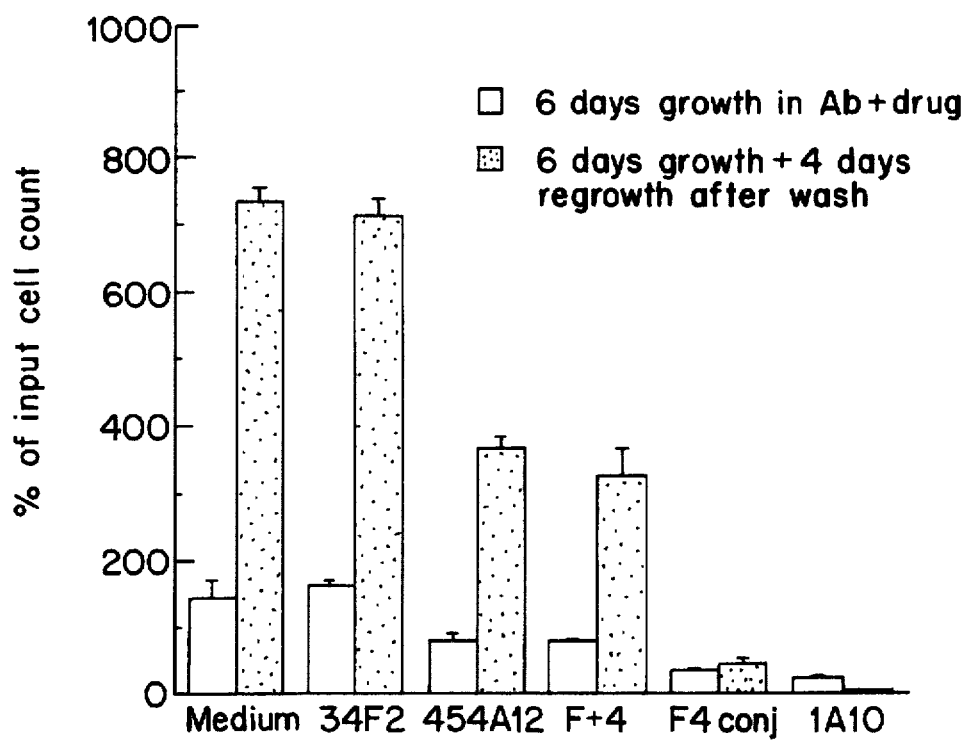
FIG. 18 shows results of regrowth experiments for human colorectal cancer cell lines SW948 and HT29 treated with purified 1A10 antigen fork or control antibodies in the presence of 5 μg/ml deferoxamine.
Figure 18B:
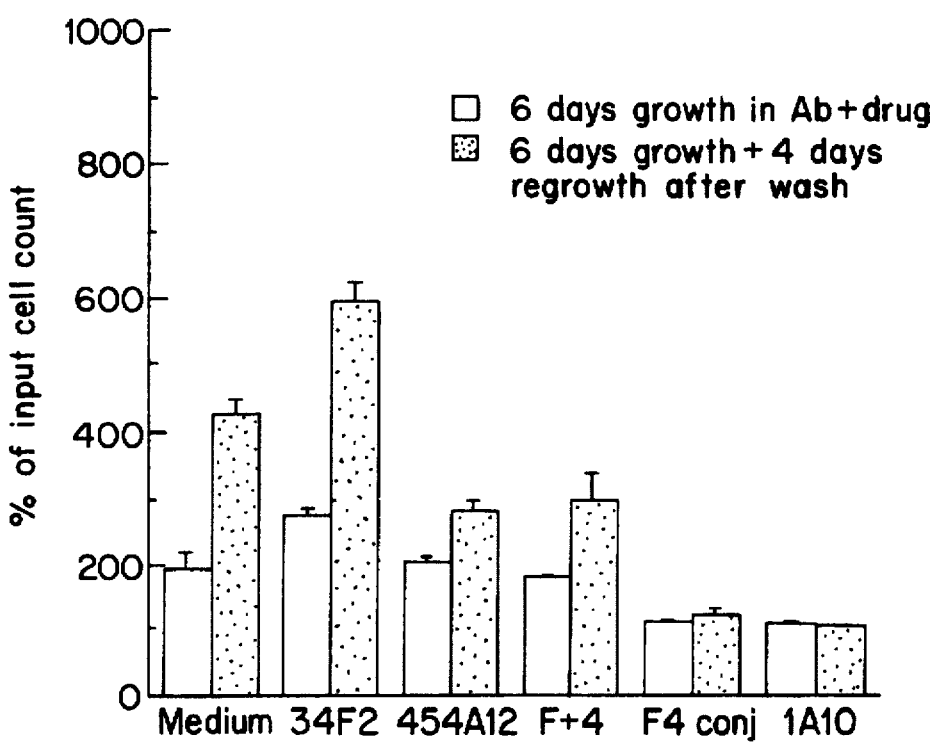

To determine whether the combination of 1A10 monovalent antigen fork and deferoxamine could kill tumor cells (as well as inhibiting their growth), tumor cells were incubated for 6 days in a combination of antigen fork and drug, and then washed and incubated another 4 days in fresh growth medium to see whether surviving tumor cells were able to regrow. FIG. 18 shows results for human colorectal cancer cell lines SW948 (panel A) and HT29 (panel B). In both cases, 1A10 was used at 1 μg/ml and deferoxamine at 5 μg/ml.

Panel A shows that substantial regrowth occurred when SW948 cells were incubated 6 days in deferoxamine alone or deferoxamine+parental antibody 34F2, removed from antibody and drug, and incubated another 4 days in fresh medium. About half as much regrowth occurred when the cells were incubated in deferoxamine+parental antibody 454A12 or deferoxamine+both parental antibodies. In contrast, very little regrowth occurred when cells were incubated in deferoxamine+34F2-454A12 conjugate and none at all when cells were treated with deferoxamine+ 1A10.

Panel B shows similar results with HT29 cells. Parental antibody 454A12 or the combination of both parental antibodies allows less regrowth than deferoxamine alone or deferoxamine+34F2, but 34F2-454A12 conjugate or 1A10 monovalent antigen fork allow essentially no regrowth.

These results indicate that the combination of 1A10 monovalent antigen fork plus deferoxamine can kill, rather than merely inhibiting tumor cells, and that 1A10 is as effective in this regard as the chemically linked heteroconjugate of its parental antibodies.

EXAMPLE 13

Production, purification and inhibition of cancer cell growth by TS44-1A2c1C11c1D1

Fusion TS44 was done with hybridomas 454A12c3G1c82F1 (passage 51) and 741F8c1C10c2B9 (passage 25) according to procedures similar to Example 10. Four days prior to fusion, 741F8 and 454A12 hybridoma cells were each split 1:50 in fresh growth medium (Iscove's modified Dulbecco's medium+2 mM glutamine+OPI+ 10–15% fetal bovine serum), resulting in a density of about 20,000 cells/ml. All cell culture in this and the following steps was carded out at 37° C. in 5% $CO_2$ incubators. Cells were approximately 90% viable on the day of fusion. Fifty million cells of each hybridoma were spun down in a desktop centrifuge and resuspended in 10 mls growth medium containing labeling agent. 741F8 hybridoma cells were labeled for 20 min at room temperature in 4 μg/ml hydroethidine (Molecular Probes). 454A12 cells were labeled for 10 min at 37° C. in 0.3 μg/ml rhodamine 123 and 10 μM verapamil (both from Sigma). After labeling, 12 ml of Ficoll Hypaque (Sigma) were underlayer, and the tubes were centrifuged for 20 min, 400×g at room temperature. Cells at the interface were collected and rinsed twice with 10 mls HBSS—(Hanks' balanced salt solution without calcium or magnesium) containing 10 μM verapamil. 741F8 hybridoma cells were further incubated with 100 μg/ml 454A12 MAb for 20 min at room temperature (to block cell surface transferrin receptors, which otherwise cause cell aggregates by binding to surface 454A12 molecules on 454A12 cells). The labeled cell populations were then mixed 1:1 and centrifuged for 1 min, 200×g at room temperature in a 50 ml polypropylene tube.

1 ml of HBSS-+(Hanks' balanced salt solution without calcium but with 2 mM $MgCl_2$) and 50 μl of freshly thawed peanut agglutinin stock (Sigma; 100 μg/ml in HBSS-+) were added to each well of a six well microtiter plate, and incubated for 2 hours at 37° C. prior to use. All parts of the fusion procedure were carried out at 37° C. Mixed labeled cells from above were resuspended at 1e7/ml in HBSS-+plus 10 μM verapamil, and 2 mls of suspended cells were added to each pretreated well. Cells were spun down onto the well bottoms by centrifuging at 400×g for 6 min at room temperature, bringing the speed up slowly. The supernatant was aspirated from the cell monolayer, and 2 mls of 40% polyethylene glycol (PEG 4000; Gibco) in HBSS-+plus 10% DMSO was added down the side of each well. The plate was swirled once or twice and left still for 1 min. 4 mls of HBSS-+containing 5% DMSO and 20 μM verapamil was added to each well with constant swirling over 2 min, followed by adding another 4 mls over 1 min. The wells were aspirated, and 4 mls of the same buffer were added to each well over 2 min. After adding another 5 mls per well of HBSS-+plus 20 μM verapamil, the plate was centrifuged at 400×g for 1 min. The plate was then washed twice with 5 mls of HBSS-+plus verapamil per well. Finally, 5 mls/well of growth medium containing 15% FBS were added, and the cells were incubated for 4 hrs at 37° C.

All but 2 mls of supernatant was aspirated from each well and the cells were then resuspended in about 5 million cells/ml and sorted on an ELITE cell sorter (Coulter), exciting with a 488 nm argon ion laser. Green (rhodamine 123) fluorescence was analyzed using a 525 nm bandpass filter, and red (ethidium) fluorescence was analyzed using a 610 nm long pass filter. Approximately 1000 cells with simultaneous high red and green fluorescence were collected and incubated overnight in 5 mls growth medium in a one well of a six well tissue culture plate. On the following day, the cells were plated at approximately 2 cell/well in 96 well flat bottom microtiter plates containing 100 μl/well growth medium and grown for 8 days. Sixty-two of 1056 wells showed growing clones, which were transferred into new wells in a single flat bottom 96 well plate with 200 μl/well fresh growth medium and grown for another 4 days. Clone supernatants were then tested for the ability to compete with binding of probes recognizing the same antigens as the parental antibodies.

Sixty-four out of 960 clones grew and supernatants from all 64 wells were tested in ELISA for binding to c-erbB2 and in probe blocking assays against MAb 454A12 probe. Supernatants from 8 wells showed both binding activity to c-erbB2 and blocking activity against anti-transferrin receptor MAb 454A12. Supernatants of these 8 clones were then tested in an MTT growth assay on the SKBR3 breast cancer cell line, according to the protocol in Example 10. All 8 clones were able to inhibit growth of SKBR3 cells. All 8 clones were also stained for DNA content as follows.

Figure 30A:
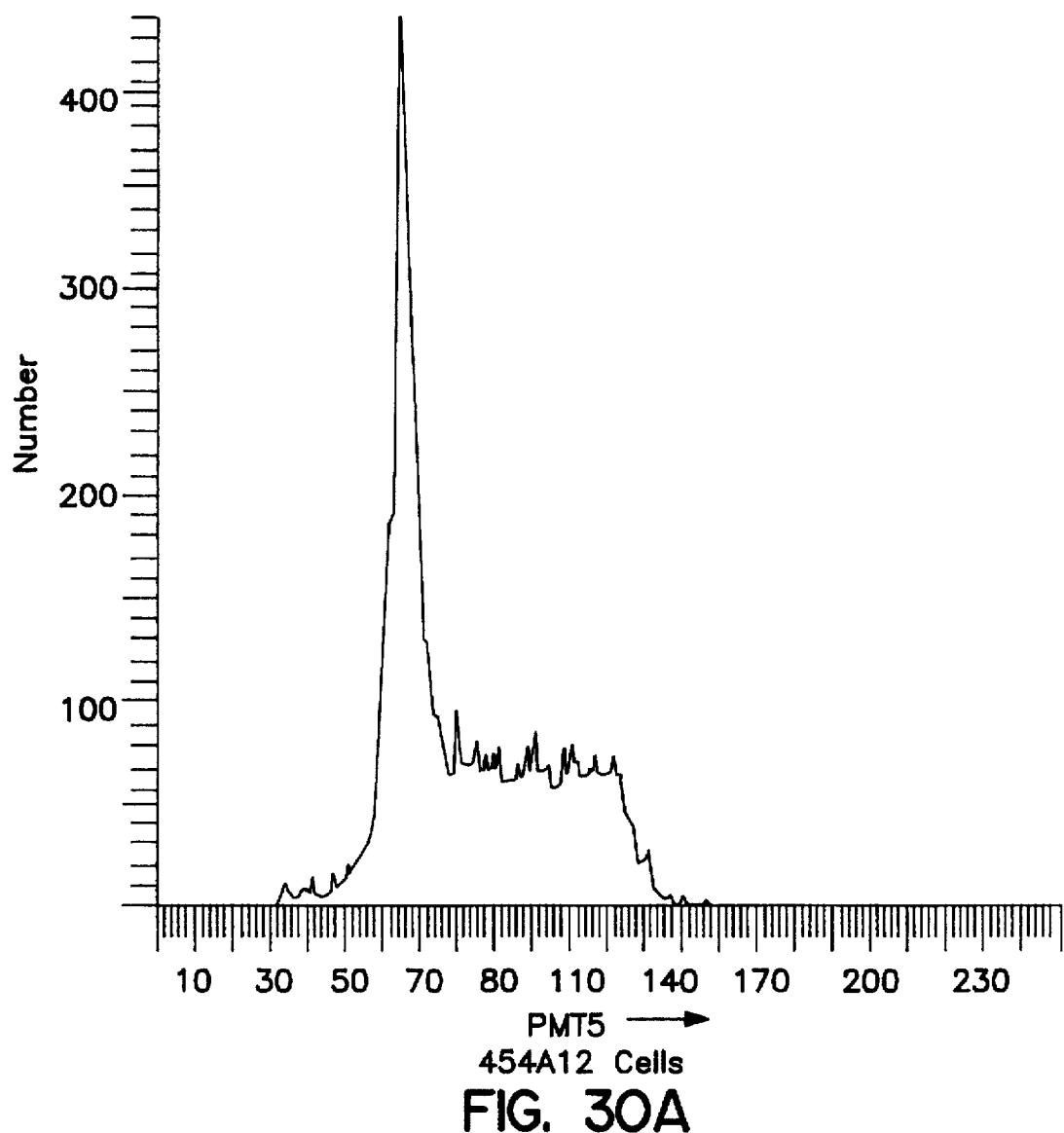
FIG. 30 shows the results of DNA staining of 454A12, 741F8 and 1A2 cells indicating relative amounts of DNA present in the cells.
Figure 30B:
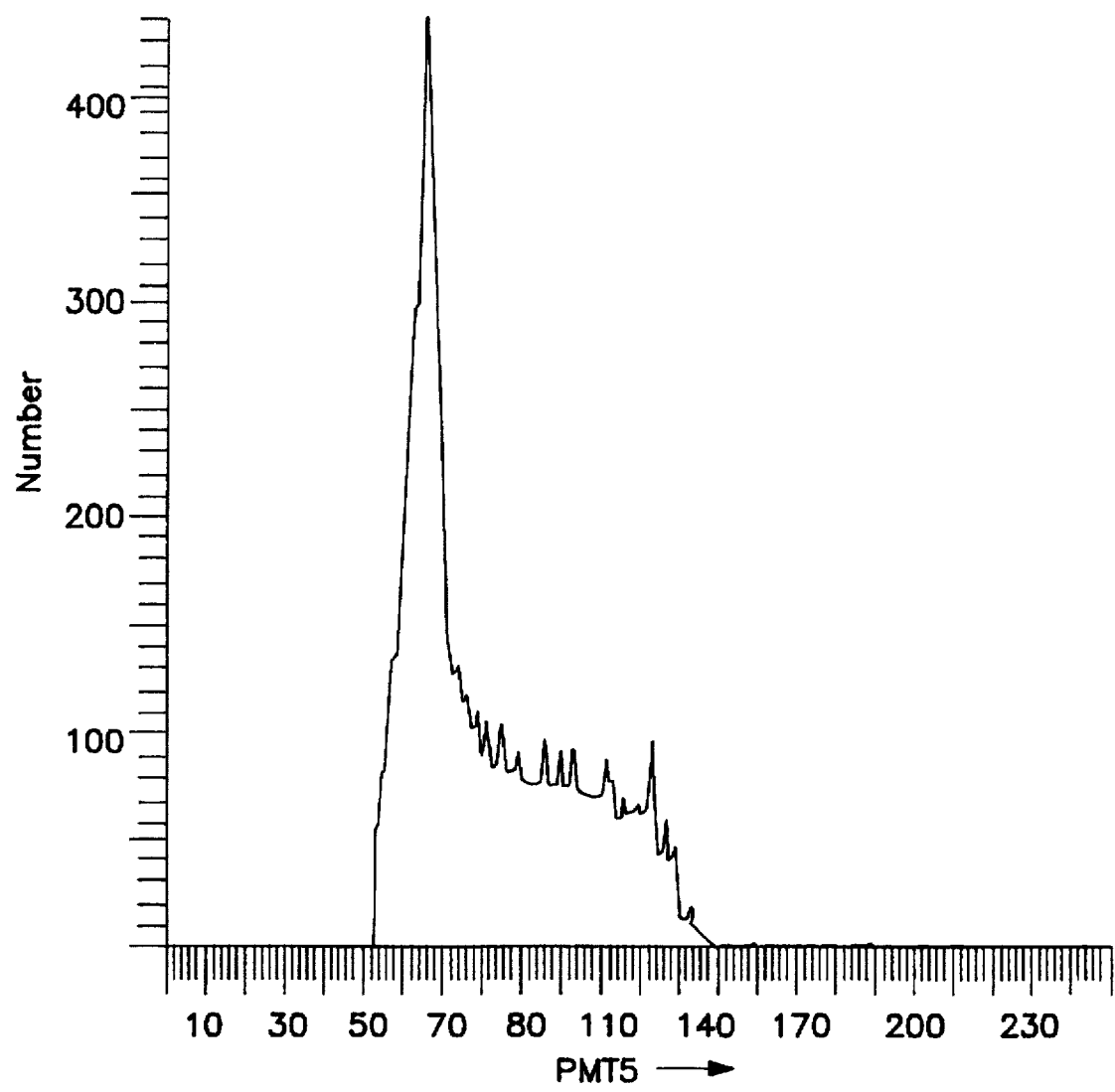
Figure 30C:
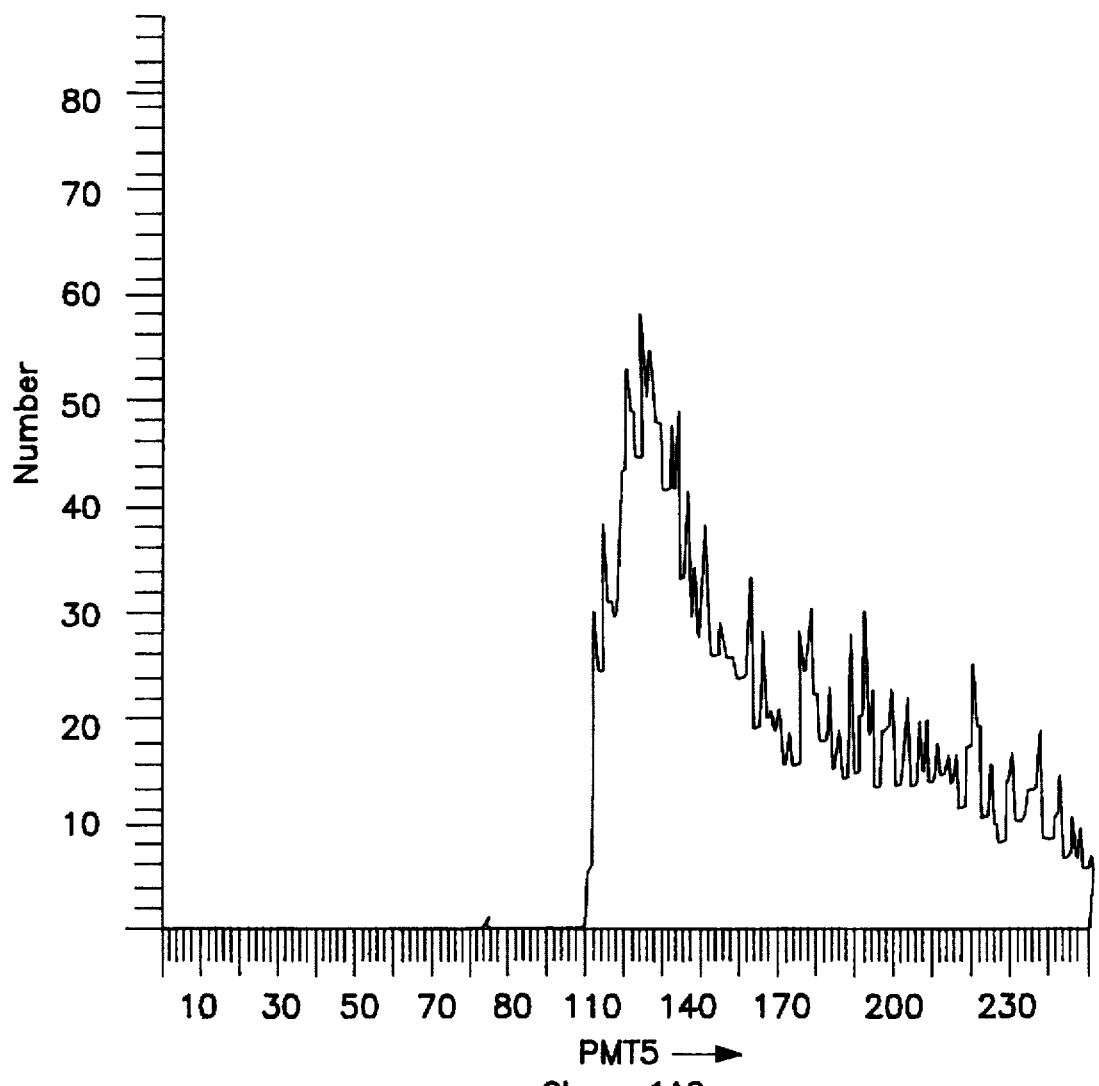

One million cells from each clone were washed twice with PBS without calcium or magnesium. To fix the cells, the pellets were resuspended by vortexing in 0.3 mls ice cold PBS, and 0.7 mls of ice cold methanol was added with additional vortexing. The mixture was spun at 200×g for 4 min and resuspended in 100 μl PBS containing DNase-free RNase A (Qiagen). After incubating at 37° C. for 60 min, the cells were resuspended in PBS containing 50 μg/ml propidium iodide, and incubated at room temperature for at least 30 min in the dark. FIG. 30 shows the DNA staining of 454A12, 741F8 and 1A2. The presumed G1 peak of hybrid hybridoma clone TS44-1A2 was at the position of the presumed G2 peaks of 454A12 and 74 1F8, indicating that the DNA content of 1A2 was close to double the amount of DNA of either parental hybridoma.

One of these clones, TS44-1A2, was subcloned at 0.5 cells per well by limiting dilution, and the resulting subclones were again screened by ability to bind to c-erbB2 and to block 454A12 probe. Twenty-eight out of 192 subclones grew and were tested. 25/28 (89%) showed both binding to c-erbB2 and blocking of 454A12. Six of these subclones were tested in an MTT growth assay and 5/6 subclones inhibited growth of SKBR3 cells. One of these subclones, TS44-1A2c1C11, was again subcloned at 0.5 cells per well. 85/480 wells grew and 69 wells were tested. 66/69 wells (96%) were found to bind c-erbB2 and block 454A12 probe. Ten subsubclones were tested in an MTT assay and 10/10 inhibited growth of SKBR3 cells.

Figure 19:
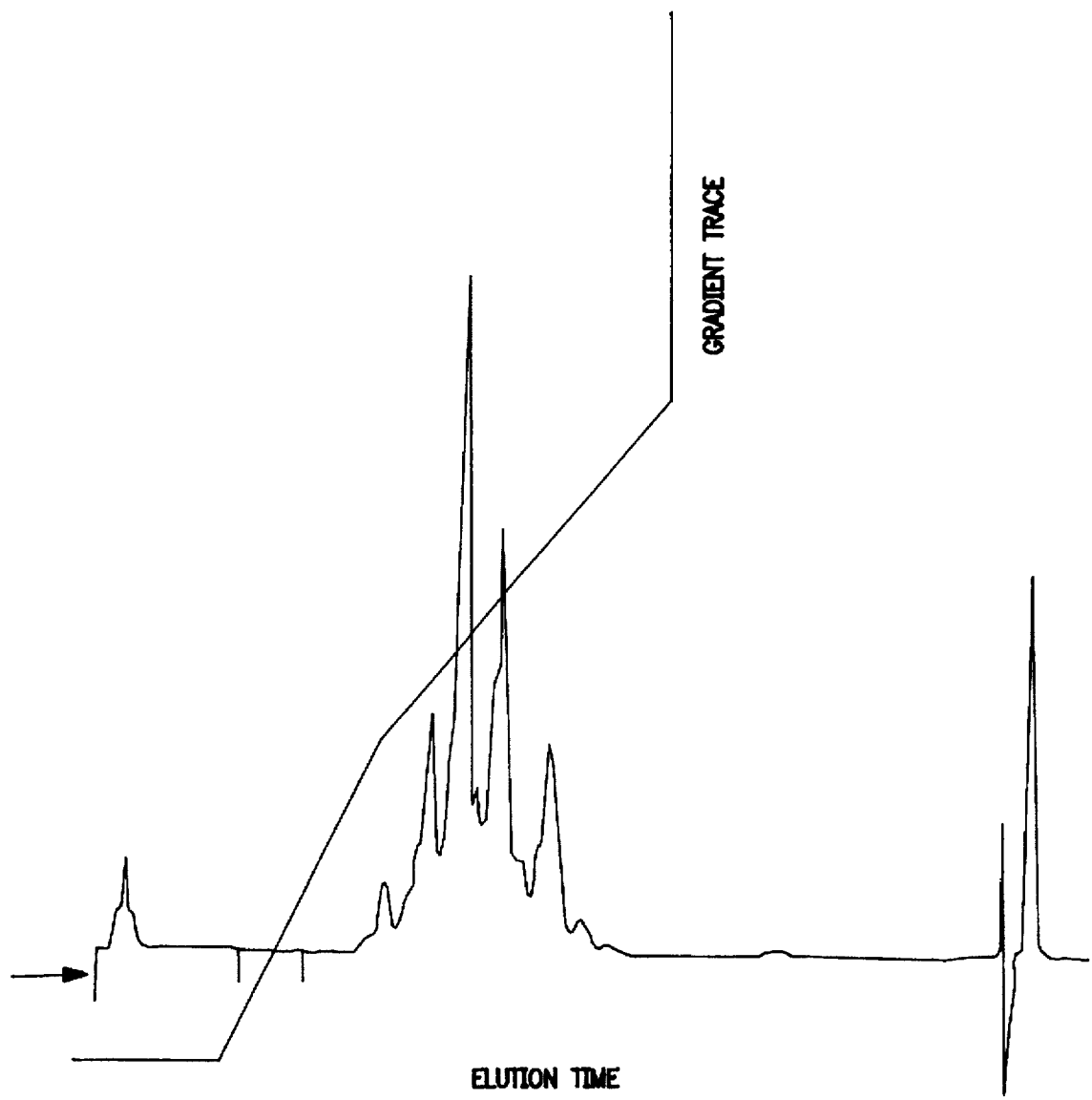
FIG. 19 shows the UV trace of eluted immunoglobulin peaks obtained by S sepharose chromatography of bispecific and parental antibodies produced by hybrid hybridoma clone TS44-1A2c1C11c1D1, derived in fusion of parental hybridomas 454A12 and 741F8.

Subsubclone TS44-1A2c1C 11c1D1 was chosen for ascities fluid production, followed by affinity purification according to the protocol in Examples 11A and B. The eluate from the protein G column was dialyzed, filtered and run over a 4.6 mm×10 cm column containing Rainin PureGel™strong cation exchange medium. The column was then washed with 10 ml of 50 mM sodium acetate pH5.5 (buffer A) at 1 ml/min. Immunoglobulins were eluted with a gradient between buffer A and 20 mM sodium phosphate pH 7.6 (buffer B) at 1 ml/min, as follows: 0–30% buffer B over 15 min, then 30–100% buffer B over 60 min. At 85% buffer B, the second part of the gradient was stopped and 1 ml of 1M sodium chloride pH 7 was injected to remove any tightly bound protein. FIG. 19 shows the UV trace of eluted immunoglobulin peaks.

Figure 20:
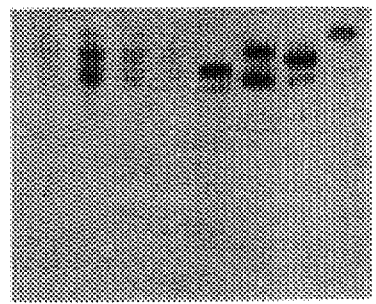
FIG. 20 shows a Pharmacia PhastGel® run under native conditions and containing the fractions shown in FIG. 19.
Figure 21:
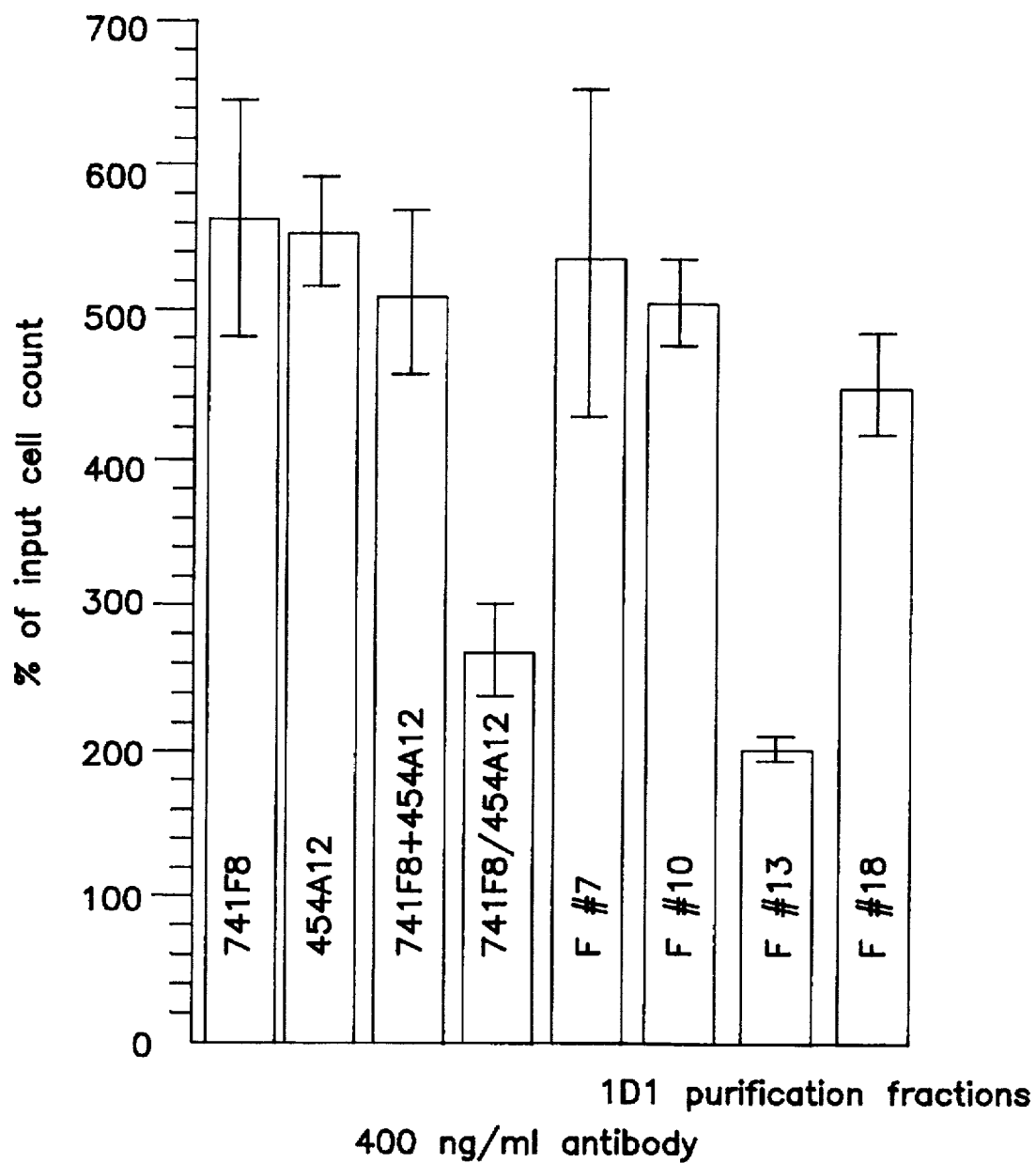
FIG. 21 shows the results of an MTT growth assay using the fractions from FIG. 19, the parental antibodies and heteroconjugates of the parental antibodies.

Fractions representing four major UV trace peaks were concentrated and run on a Pharmacia PhastGel®under native conditions (FIG. 20 ) and were tested in an MTT growth assay (FIG. 21 ). The parental antibodies, their combination, and the fractions from the first, second and fourth peaks did not strongly inhibit growth (446% to 564% of input cell count compared to 531% in the absence of any antibody). On the other hand, the fraction from the third peak caused significantly greater inhibition (198% of input cell count). Growth inhibition by the third peak was actually slightly stronger than by the heteroconjugate 741F8/454A12 (267% of input cell count). From the PAGE mobility and the growth inhibitory activity, it is believed that the major immunoglobulin species in peak 3 represents the desired 741F8/454A12 hybrid hybridoma-derived monovalent bispecific antigen fork, which was named 1D1.

Figure 22:
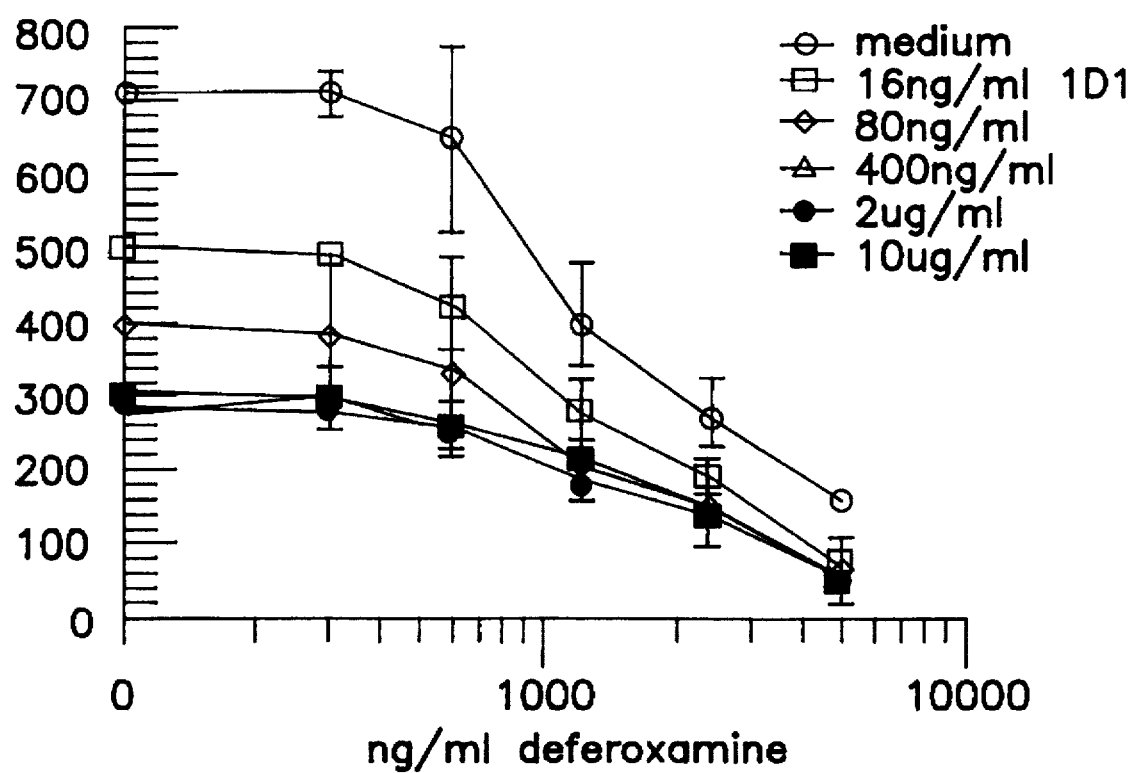
FIGS. 22 and 23 show the effect of 1D1 in combination with various concentrations of deferoxamine on the SKBR3 cell line.
Figure 23:
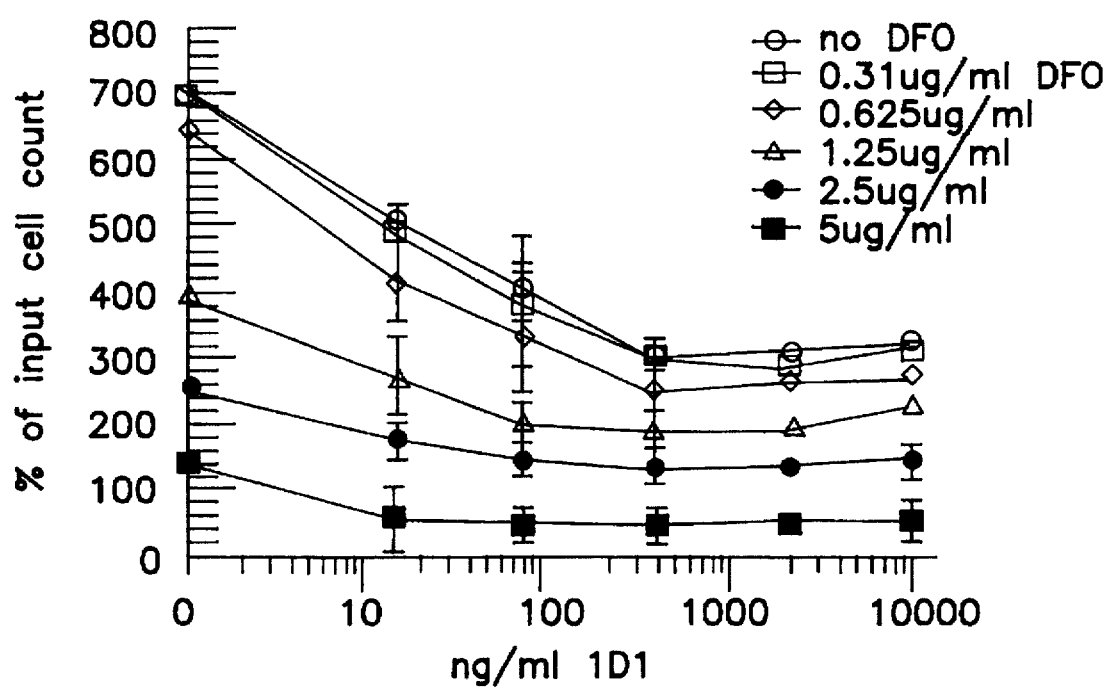
Figure 24:
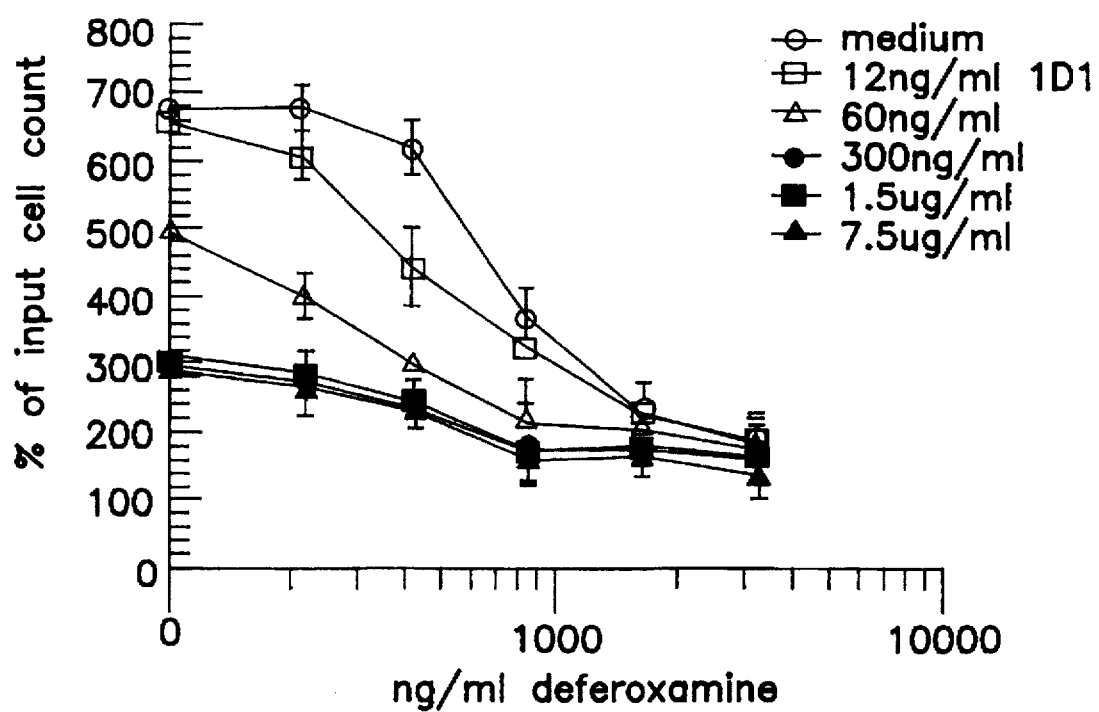
FIGS. 24 and 25 show the effect of 1D1 in combination with various concentrations of deferoxamine on the ovarian cancer cell line SKOV3.
Figure 25:
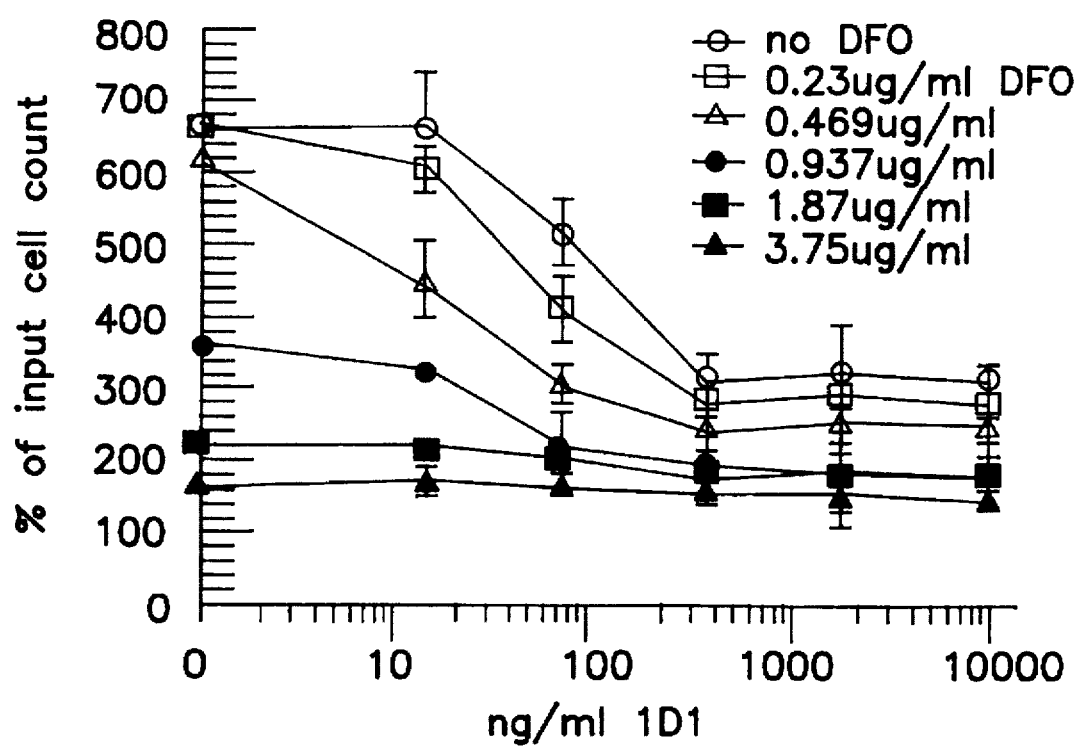
Figure 26:
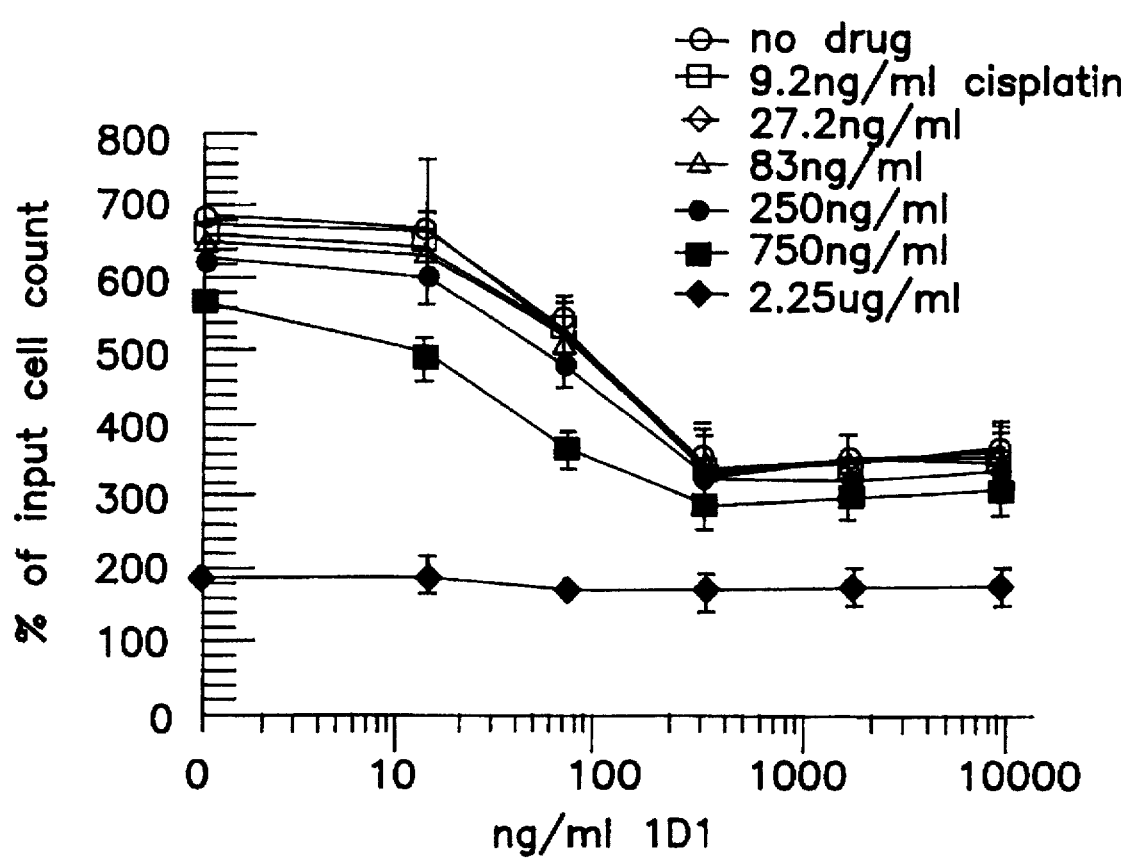
FIG. 26 shows the effect of 1D1 in combination with various concentrations of cisplatin on SKOV3 cells.
Figure 27:
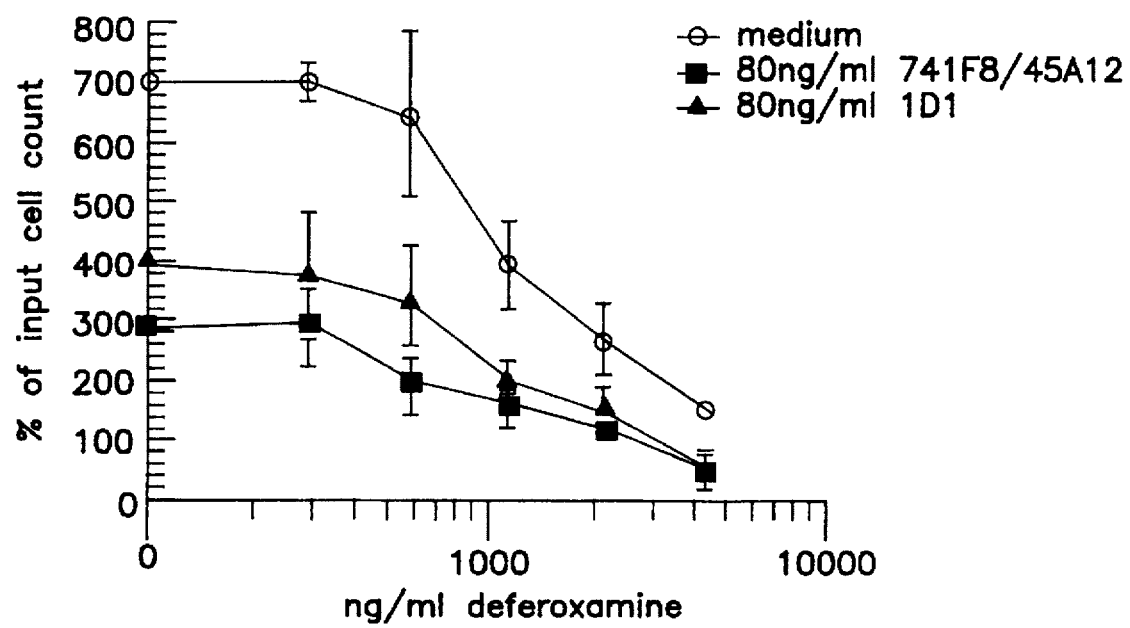
FIGS. 27 and 28 show the growth inibitory activities of 1D1 and heteroconjugate 741F8/454A12 on the SKBR3 and SKOV3 cell lines.
Figure 28:
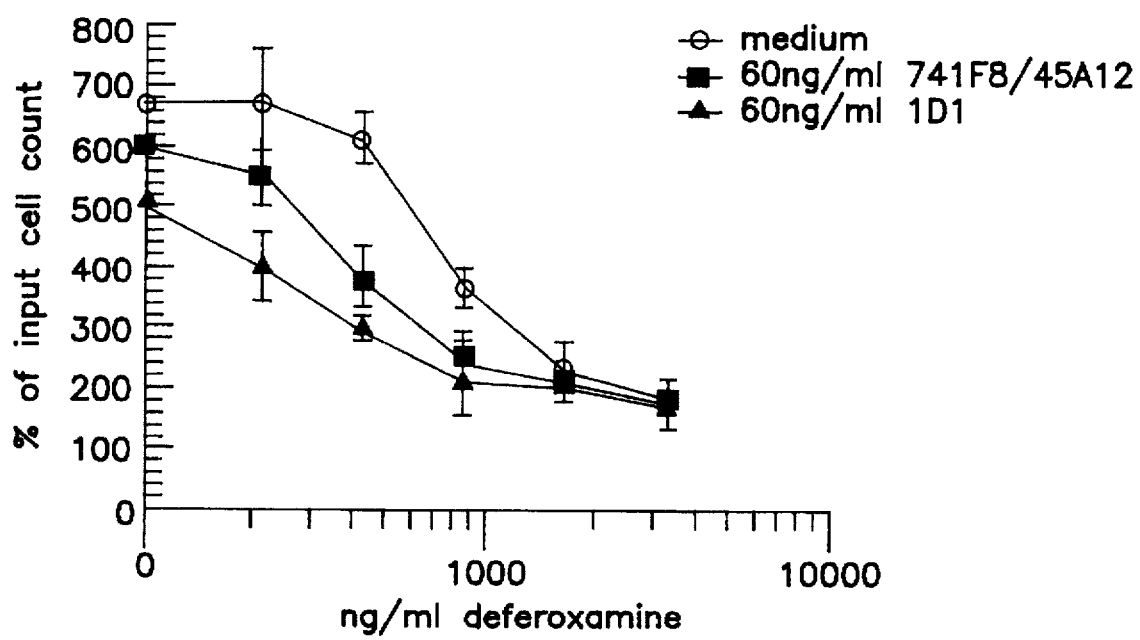
Figure 29:
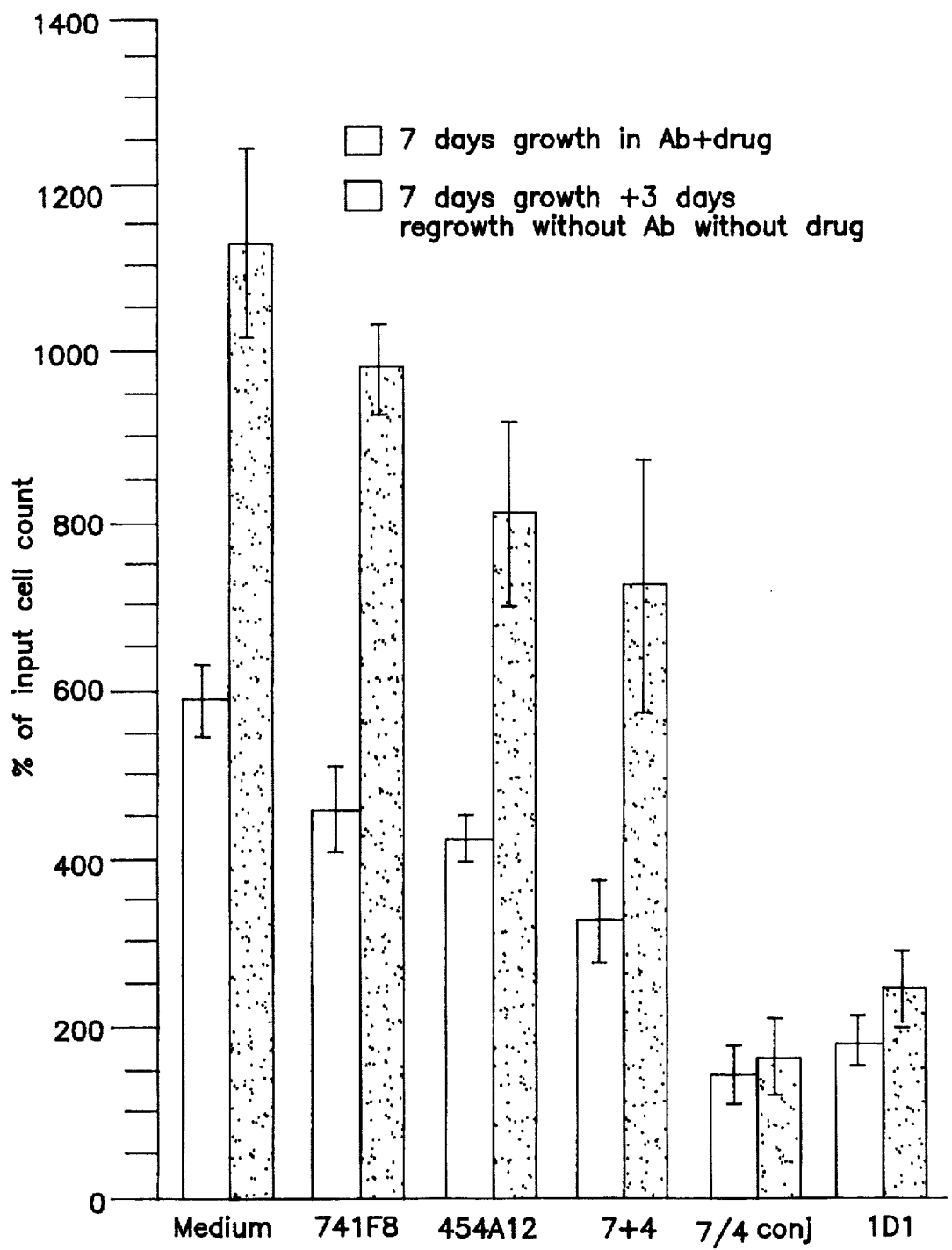
FIG. 29 shows the results of regrowth assays using 1D1 done according to the protocol in Example 12E hereinbelow.

1D1 was further tested on the SKB3B cell line (FIGS. 22 and 23) and on ovarian cancer cell line SKOV3 (FIGS. 24 and 25) in combination with various concentrations of deferoxamine. 1D1 was also tested on SKOV3 cells with various concentrations of cisplatin ( FIG. 26). FIGS. 27 and 28 compare the growth inibitory activities of 1D1 and heteroconjugate 741F8/454A12 on the SKBR3 and SKOV3 cell lines. Regrowth assays using 1D1 were done according to the protocol in Example 12E (FIG. 29).

EXAMPLE 14

Figure 32:
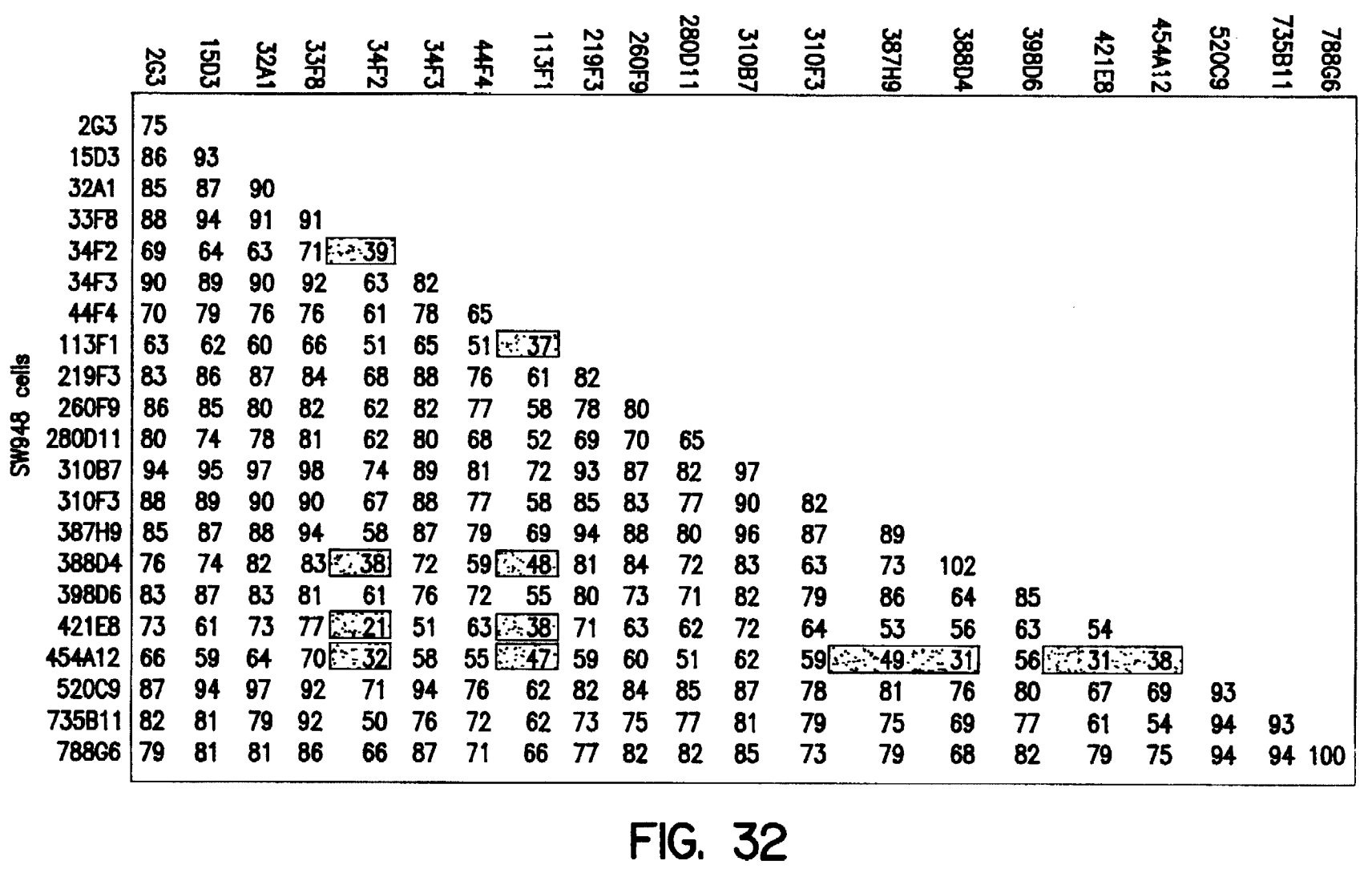

Screening of Monoclonal Antibody Pairs by Cross-Linking with Goat Anti-Mouse IgG Twenty-one monoclonal antibodies were tested in pairs for growth inhibitory activity against breast cancer cell line SKBR3 and colorectal cancer cell line SW948. Cells were seeded at 10,000 cells/well (SKBR3) or 5000 cells/well (SW948) in 50 μl into 96 well tissue culture plates and incubated overnight at 37° C., 5% $CO_2$. Monoclonal antibodies were dialysed free of sodium azide and sterile filtered. Pairs of MAbs were added to the seeded cancer cells in triplicate wells. Each MAb was used at a final concentration of 5 μg/ml. Goat anti-mouse IgG (H+L) was added to each well at a final concentration of 50 μg/ml. The plates were incubated for 7 days at 37° C., 5% $CO_2$. A Promega CellTiter96 MTT assay kit was used to evaluate the number of viable cells in each well, according to the protocol in Example 10E. The results of these assays are shown in FIGS. 31 and 32. FIG. 31 shows the effects of the cross-linked MAb pairs on viability of SKBR3 cells. FIG. 32 shows the effects of the cross-linked MAb pairs on viability of SW948 cells. Results are expressed as % of control cell growth=100%×mean A570 of MAb pair/mean A570 of wells without MAb. The shaded values indicate those values below 50%, one level that could be selected for continued testing of the pair by production of chemical conjugates of the MAbs or by production of bispecific antibodies. The results of these experiments demonstrate that only a very few of the combinations tested effected a reduction below 50%, thus demonstrating the advantage of the method of the present invention.

Deposition of Cultures

The hybridomas used in the above examples to illustrate the method of the present invention were deposited in and accepted by the American Type Culture Collection (ATCC), 12301 Parklawn Drive, Rockville, Md., U.S.A., under the terms of the Budapest Treaty. The deposit dates and the accession numbers are given below:

| Culture | Deposit Date | Accession No. |
| --- | --- | --- |
| 2G3 | 27 January 1984 | ATCC HB 8491 |
| 113F1 | 27 January 1984 | ATCC HB 8490 |
| 260F9-2B7 | 27 January 1984 | ATCC HB 8488 |
| 260F9-1C9 | 27 January 1984 | ATCC HB 8662 |
| 317G5-1D4 | 27 January 1984 | ATCC HB 8485 |
| 317G5-1D3 | 28 December 1984 | ATCC HB 8691 |
| 454A12 | 18 June 1985 | ATCC HB 10804 |
| 520C9 | 8 January 1985 | ATCC HB 8696 |
| 650E2 | 18 June 1985 | ATCC HB 10812 |
| 15D3 | 6 May 1993 | ATCC HB 11342 |
| 741F8-2B9 | 18 June 1985 | ATCC HB 10807 |
| TS44-1A2c1C11c1D1 | 21 September 1994 | ATCC HB 11719 |
| TS37-4A3c2E3c1AT0(34F2) | 07 December 1993 | ATCC HB 11499 |
| 387H9 | 18 June 1985 | ATCC HB 10802 |
| 388D4-5E7 | 04 June 1985 | ATCC HB 10794 |

-continued

| Culture | Deposit Date | Accession No. |
| --- | --- | --- |
| 421E8-4B4 | 04 June 1985 | ATCC HB 10793 |

I claim:

1. A method of producing antigen forks, said method comprising:

a. contacting a homogeneous culture of cells with a first antibody, said first antibody having an antigen binding site capable of recognizing and binding to a first antigen present on the surface of said cells under conditions allowing said first antibody to bind to said cells;

b. contacting said homogeneous culture of cells with a second antibody, said second antibody having an antigen binding site capable of recognizing and binding to a second antigen present on the surface of said cells under conditions allowing said second antibody to bind of said cells, said first and second antibodies having at least one common epitope;

c. contacting said first and second antibodies with a third antibody, said third antibody capable of recognizing and binding said at least one common epitope under conditions allowing said third antibody to bind to said first and second antibodies;

d. determining whether treatment of said cells according to steps (a) through (c) results in a decrease in the viability of said cells;

e. constructing said antigen fork using a molecule comprising said antigen binding site from said first antibody and a molecule comprising said antigen binding site from said second antibody when said treatment of said cells according to steps (a) through (c) results in a decrease in the viability of said cells.

* * * * *